US012057235B2

(12) United States Patent
Ikeshima

(10) Patent No.: US 12,057,235 B2
(45) Date of Patent: Aug. 6, 2024

(54) APPARATUS, SYSTEM, AND METHOD FOR PROVIDING INFORMATION RELATED TO INFECTIOUS DISEASE, VIA VOICE RECOGNITION DEVICE

(71) Applicant: Panasonic Intellectual Property Management Co., Ltd., Osaka (JP)

(72) Inventor: Hiroko Ikeshima, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 809 days.

(21) Appl. No.: 17/081,960

(22) Filed: Oct. 27, 2020

(65) Prior Publication Data

US 2021/0043330 A1     Feb. 11, 2021

Related U.S. Application Data

(63) Continuation of application No. PCT/JP2019/027290, filed on Jul. 10, 2019.

(30) Foreign Application Priority Data

Aug. 8, 2018   (JP) .................................. 2018-149706
Aug. 8, 2018   (JP) .................................. 2018-149707
(Continued)

(51) Int. Cl.
*G16H 50/80*     (2018.01)
*G08B 21/02*     (2006.01)
(Continued)

(52) U.S. Cl.
CPC ............. *G16H 50/80* (2018.01); *G08B 21/02* (2013.01); *G10L 25/66* (2013.01); *G16H 40/67* (2018.01); *G16H 50/30* (2018.01); *H04W 4/023* (2013.01)

(58) Field of Classification Search
CPC ........ G16H 50/80; G16H 50/30; G10L 25/66; H04W 4/023
See application file for complete search history.

(56) References Cited

U.S. PATENT DOCUMENTS

2017/0024531 A1*   1/2017   Malaviya ............... G16H 50/30
2017/0125034 A1    5/2017   Kakadiaris et al.
(Continued)

FOREIGN PATENT DOCUMENTS

JP     2011-089921 A      5/2011
JP     2011-248802        12/2011

OTHER PUBLICATIONS

International Search Report of PCT application No. PCT/JP2019/027290 dated Oct. 1, 2019.
(Continued)

*Primary Examiner* — Thomas H Maung
(74) *Attorney, Agent, or Firm* — Rimon P.C.

(57) ABSTRACT

An information providing method includes: acquiring, from one or more voice recognition devices, regional infection information indicating one or more infection alert levels and one or more regions associated with the one or more infection alert levels, the one or more infection alert levels being obtained by the one or more voice recognition devices analyzing a voice signal; calculating, based on the regional infection information, an infection risk value representing a magnitude of a risk of infection in each of the one or more regions; and generating output information in accordance with the infection risk value for each of the one or more regions.

11 Claims, 27 Drawing Sheets

(30) Foreign Application Priority Data

Aug. 8, 2018 (JP) .................................. 2018-149708
Jun. 27, 2019 (JP) .................................. 2019-120241

(51) Int. Cl.
*G10L 25/66* (2013.01)
*G16H 40/67* (2018.01)
*G16H 50/30* (2018.01)
*H04W 4/02* (2018.01)

(56) References Cited

U.S. PATENT DOCUMENTS

2017/0199979 A1* 7/2017 Reiner .................. G16H 10/60
2020/0004746 A1* 1/2020 Randall ............... G06F 16/2455
2021/0158966 A1* 5/2021 Ozaki ................... G16H 50/30

OTHER PUBLICATIONS

English Translation of Chinese Search Report dated Dec. 5, 2023 for the related Chinese Patent Application No. 201980023953.0.

* cited by examiner

FIG. 4

| SMART SPEAKER ID | ****** |
|---|---|
| PLACE OF INSTALLATION | CC, MORIGUCHI, OSAKA |
| ANNOUNCEMENT SETTING | ON |
| ANNOUNCEMENT DISTRICT SETTING | ASSOCIATED DISTRICT INCLUDED |
| DEVICE CONTROL SETTING | AUTOMATIC |

} T11

REGISTRATION INFORMATION

| No. | USER | FIRST DESIGNATION | SECOND DESIGNATION | THIRD DESIGNATION | VOICEPRINT REGISTRATION NO. | AGE | SEX | PLACE OF FREQUENT VISIT 1 | LEVEL OF FREQUENT VISIT 1 | REFERENCE DURATION OF STAY 1 | PLACE OF FREQUENT VISIT 2 | LEVEL OF FREQUENT VISIT 2 | REFERENCE DURATION OF STAY 2 | DISEASE INFORMATION | ASSOCIATED DESIGNATION | RELATIONSHIP |
|---|---|---|---|---|---|---|---|---|---|---|---|---|---|---|---|---|
| 1 | TARO | DAD | TARO-SAN | | 1 | 42 | M | AB CORPORATION WORKPLACE | 4 | 9 h | DD GYM | 2 | 2 h | METS | DIRECTOR MATSUSHITA | SUPERIOR |
| 2 | HANAKO | MOM | HANAKO-CHAN | | 2 | 40 | F | SUPERMARKET CC | 5 | 0.5 h | EE SHOPPING MALL | 2 | 2 h | NONE | KEITA-CHAN'S MOM | FRIEND |
| 3 | KOTARO | KEITA-CHAN | | 1 | 3 | 8 | M | CC ELEMENTARY SCHOOL/OC SCHOOL | 4 | 7 h | CC SWIMMING SCHOOL | 3 | 1.5 h | ATOPY | KEN-CHAN | FRIEND |
| 4 | KOJIRO | KOJI-CHAN | | 1 | 4 | 5 | M | CC KINDERGARTEN SCHOOL | 4 | 6 h | CC PARK | 3 | 1 h | ASTHMA | RIKA-CHAN | FRIEND |

REGIONAL INFECTION INFORMATION

| TIME | DETECTION CONTENT | SOURCE | PLACE | DISTRICT | INFECTION ALERT LEVEL | ESTIMATED NAME OF INFECTIOUS DISEASE | EPIDEMIC PERIOD CORRECTION VALUE | SUBJECT NO. | POSSIBILITY OF INFECTION | ANCILLARY DATA |
|---|---|---|---|---|---|---|---|---|---|---|
| 7:00 01/18/2018 | "I HEARD THAT THE CLIENT I MET AT WORK YESTERDAY HAD THE FLU" | No. 1 / SOUND PRODUCTION | AB CORPORATION | BB DISTRICT | 4 | INFLUENZA | x1 | 1 | 5 | MOVEMENT INFORMATION/ SMARTPHONE |
| 7:02 01/18/2018 | "THE CLASS NEXT DOOR WAS TEMPORARILY CLOSED LAST MONTH" | No. 3 / SOUND PRODUCTION | CC ELEMENTARY SCHOOL | CC DISTRICT | 5 | INFLUENZA | x0.5 | 3 | 3 | |
| 7:03 01/18/2018 | "RIKA-CHAN IS ABSENT" "SHE HAS A HIGH FEVER" | No. 4 / SOUND PRODUCTION | CC KINDERGARTEN | CC DISTRICT | 3 | COLD | x1 | 4 | 5 | |
| 7:10 01/18/2018 | "TELL ME PREDICTION OF EPIDEMICS OF THE FLU" | No. 2 / SEARCH | HOUSE | CC DISTRICT | 1 | INFLUENZA | x1 | 1 | 1 | |
| 20:00 01/23/2018 | "I'VE BEEN FEVERISH SINCE YESTERDAY" | No. 1 / SOUND PRODUCTION | HOUSE | CC DISTRICT | 2 | COLD | x1 | 1 | 6 | MOVEMENT INFORMATION/ SMARTPHONE |
| 20:30 01/23/2018 | SNEEZING SOUND | No. 1 / SOUND PRODUCTION | HOUSE | CC DISTRICT | 2 | COLD | x1 | 1 | 6 | MOVEMENT INFORMATION/ SMARTPHONE |
| 20:40 01/23/2018 | SNEEZING SOUND | No. 1 / SOUND PRODUCTION | HOUSE | CC DISTRICT | 2 | COLD | x1 | 1 | 6 | MOVEMENT INFORMATION/ SMARTPHONE |

FIG. 6

REGISTRATION INFORMATION  10

| No. | USER | FIRST DESIGNATION | SECOND DESIGNATION | THIRD DESIGNATION | VOICEPRINT REGISTRATION NO. | AGE | SEX | PLACE OF FREQUENT VISIT 1 | LEVEL OF FREQUENT VISIT 1 |
|---|---|---|---|---|---|---|---|---|---|
| 1 | TARO | DAD | TARO-SAN | | 1 | 42 | M | AB CORPORATION/ WORKPLACE | 4 |
| 2 | HANAKO | MOM | HANA-CHAN | | 2 | 40 | F | SUPERMARKET CC | 5 |
| 3 | KOTARO | | KOTA-CHAN | | 3 | 8 | M | CC ELEMENTARY SCHOOL/SCHOOL | 4 |
| 4 | KOJIRO | | KOJI-CHAN | | 4 | 5 | M | CC KINDERGARTEN/ SCHOOL | 4 |

| REFERENCE DURATION OF STAY 1 | PLACE OF FREQUENT VISIT 2 | LEVEL OF FREQUENT VISIT 2 | REFERENCE DURATION OF STAY 2 | DISEASE INFORMATION | ASSOCIATED DESIGNATION | RELATIONSHIP |
|---|---|---|---|---|---|---|
| 9 h | DD GYM | 2 | 2 h | ETC | DIRECTOR MATSUSHITA | SUPERIOR |
| 0.5 h | EE SHOPPING MALL | 2 | 2 h | NONE | KEN-CHAN'S MOM | FRIEND |
| 7 h | CC SWIMMING SCHOOL | 3 | 1.5 h | ATOPY | KEN-CHAN | FRIEND |
| 6 h | CC PARK | 3 | 1 h | ASTHMA | RIKA-CHAN | FRIEND |

*EVERYDAY 5, FIVE DAYS A WEEK 4, TWICE A WEEK 3, ONCE A WEEK 2, TWICE A MONTH 1

9

| TIME | DETECTION | |
|---|---|---|
| | CONTENT | SOURCE |
| 7:00 01/18/2018 | "I HEARD THAT THE CLIENT I MET AT WORK YESTERDAY HAD THE FLU" | NO. 1/SOUND PRODUCTION |

PERSON WORD
INFECTED PERSON IDENTIFIED:
NOT TARO HIMSELF, BUT
THERE IS POSSIBILITY OF
CLOSE CONTACT

DATE AND TIME WORD
DATE IDENTIFIED:
01/17/2018

DISEASE NAME WORD
DISEASE NAME IDENTIFIED:
INFLUENZA (INFECTIOUS DISEASE)
ONSET?: YES

PLACE WORD
PLACE IDENTIFIED:
WORK → FROM REGISTRATION INFORMATION
AB CORPORATION

01/18/2018 DATA

T51A

| PLACE | NUMBER OF REPORTED CASES BY INFECTION ALERT LEVEL | | | | | CORRECTION COEFFICIENT BASED ON NUMBER OF USERS | CORRECTION COEFFICIENT BASED ON ASSUMED DURATION OF STAY | ALERT LEVEL BASED ON SNS INFORMATION | ALERT LEVEL BASED ON PATIENT COUNT DATA | INFECTION RISK VALUE BASED ON COOPERATIVE SMART SPEAKER | INFECTION RISK VALUE | ASSOCIATED PLACE |
|---|---|---|---|---|---|---|---|---|---|---|---|---|
| NAME OF PLACE | 5 | 4 | 3 | 2 | 1 | | | | | | | |
| AB CORPORATION | 2 | 2 | 4 | 5 | 10 | aj | bj | cj | dj | ej | 13.8 | DD GYM... |
| AA ELEMENTARY SCHOOL | 3 | 2 | 5 | 10 | 13 | | | | | | 19.8 | |
| ... | | | | | | | | | | | | |
| *WEIGHT ASSIGNED | 3 | 1 | 0.7 | 0.4 | 0.1 | p1 | p2 | p3 | p4 | p5 | | |

T52A

| DISTRICT | NUMBER OF REPORTED CASES BY INFECTION ALERT LEVEL | | | | | CORRECTION COEFFICIENT BASED ON NUMBER OF STAYERS | CORRECTION COEFFICIENT BASED ON ASSUMED DURATION OF STAY | ALERT LEVEL BASED ON SNS INFORMATION | ALERT LEVEL BASED ON PATIENT COUNT DATA | INFECTION RISK VALUE BASED ON COOPERATIVE SMART SPEAKER | INFECTION RISK VALUE | ASSOCIATED DISTRICT |
|---|---|---|---|---|---|---|---|---|---|---|---|---|
| NAME OF DISTRICT | 5 | 4 | 3 | 2 | 1 | | | | | | | |
| BB DISTRICT | 62 | 90 | 150 | 219 | 500 | | | | | | 518.6 | |
| CC DISTRICT | | | | | | | | | | | | |
| ... | | | | | | | | | | | | |
| *WEIGHT ASSIGNED | | | | | | | | | | | | |

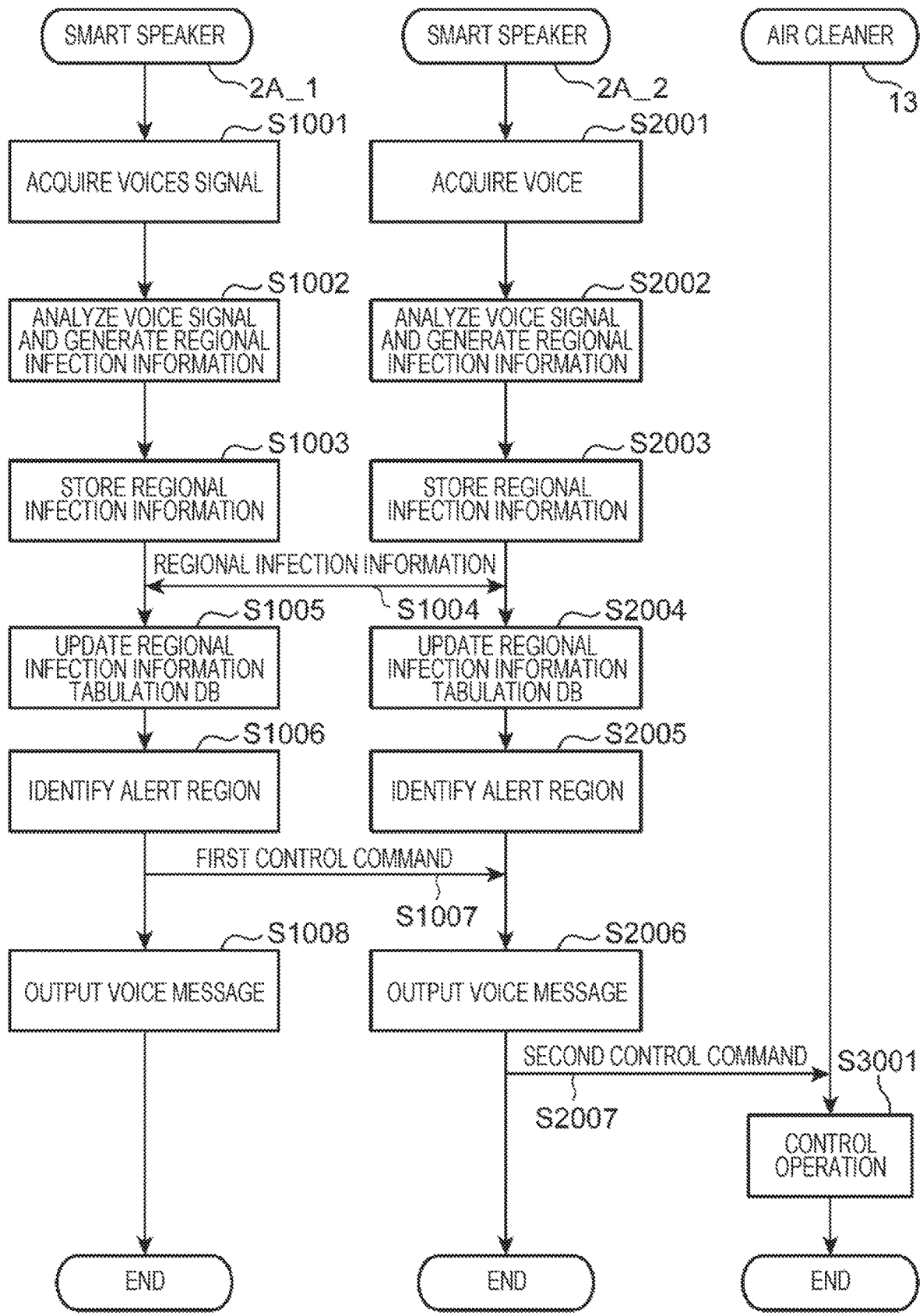

| PLACE | 9:00 01/18/2018 | | 10:00 01/18/2018 | | 11:00 01/18/2018 | | ... |
|---|---|---|---|---|---|---|---|
| | NUMBER OF POSSIBLY-INFECTED PERSONS | ENVIRONMENTAL INFORMATION | NUMBER OF POSSIBLY-INFECTED PERSONS | ENVIRONMENTAL INFORMATION | NUMBER OF POSSIBLY-INFECTED PERSONS | ENVIRONMENTAL INFORMATION | |
| AA SHOPPING CENTER | 25 | TEMPERATURE, HUMIDITY, SET VALUE, RISK OF INFECTION, INFECTION RISK VALUE | 24 | TEMPERATURE, HUMIDITY, SET VALUE, RISK OF INFECTION, INFECTION RISK VALUE | 10 | TEMPERATURE, HUMIDITY, SET VALUE, RISK OF INFECTION, INFECTION RISK VALUE | |
| STAR SQUARE | 10 | | 8 | | 5 | | |
| MOON SQUARE | 15 | | 16 | | 5 | | |
| CC SUPERMARKET | 13 | | 10 | | 8 | | |

APPARATUS, SYSTEM, AND METHOD FOR PROVIDING INFORMATION RELATED TO INFECTIOUS DISEASE, VIA VOICE RECOGNITION DEVICE

BACKGROUND

1. Technical Field

The present disclosure relates to a technology with which to provide information related to an infectious disease using a voice signal obtained by a voice recognition device.

2. Description of the Related Art

Japanese Unexamined Patent Application Publication No. 2011-248802 has been known to disclose a conventional information providing system that provides information related to an infectious disease. Japanese Unexamined Patent Application Publication No. 2011-248802 discloses a technology with which to accumulate histories of movements of infection monitoring system participants, manage, from a history of movements of an infection monitoring system participant confirmed or estimated infected with a virus by a hospital or a health center, a place accessed by the infection monitoring system participant, and, in a case where a different infection monitoring system participant has accessed the place accessed, notify the different infection monitoring system participant of the place accessed and the date and time of access by the virus-infected person to the place accessed.

SUMMARY

In one general aspect, the techniques disclosed here feature a method for providing information through an information providing system that provides information related to an infectious disease, the method including: acquiring, from one or more voice recognition devices connected to a computer of the information providing system via a network, regional infection information indicating one or more infection alert levels and one or more regions associated with the one or more infection alert levels, the one or more infection alert levels being obtained by the one or more voice recognition devices analyzing a voice signal; calculating, based on the regional infection information, an infection risk value representing a magnitude of a risk of infection in each of the one or more regions; and generating output information in accordance with the infection risk value for each of the one or more regions.

In one general aspect, the techniques disclosed here feature a voice recognition device that provides information associated with an infectious disease, the voice recognition device including: a microphone that detects an ambient sound and outputs a voice signal based on a detection result; a processor that executes a voice recognition process on the voice signal outputted by the microphone; a speaker; and a memory, wherein the processor extracts, from a result of the voice recognition process executed on the voice signal, first voice data containing at least one selected from the group consisting of a word and a sound related to a risk of infection and identifies an infection alert level from the first voice data, the processor extracts, from the result of the voice recognition process, second voice data corresponding to a sound detected by the microphone during a certain period of time before and after a time that the sound corresponding to the first voice data was detected by the microphone and identifies a region associated with the first voice data from the second voice data or identifies a region associated with the first voice data using movement history data representing a history of movements of an utterer of the first voice data, the processor generates regional infection information associating the region with the infection alert level and accumulates the regional infection information in the memory, and the processor generates a voice message corresponding to the infection alert level of the region from the regional infection information.

In one general aspect, the techniques disclosed here feature a method for providing information through an information providing system, the information providing system including a voice recognition device and a server, the information providing system providing information related to an infectious disease, the method including: using the voice recognition device to phonetically recognize a voice signal based on a sound detected using a microphone, identify a possibly-infected person who is possibly infected with the infectious disease and a possibility of the possibly-infected person being infected with the infectious disease, and transmit, to a mobile terminal of the possibly-infected person, first infection information indicating the possibility of infection; using the mobile phone to transmit, to the server, coordinate data associating positional information on the mobile terminal with the first infection information; and using the server to generate mapping data using a plurality of pieces of coordinate data, transmitted from a plurality of mobile terminals including the mobile terminal, that include the coordinate data, the mapping data associating a particular place on map data with the number of possibly-infected persons in the particular place, and transmit the mapping data to the mobile terminal of the possibly-infected person or a mobile terminal of a person who is different from the possibly-infected person.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram showing an example of a data configuration of a registration information DB stored in a memory of a smart speaker;

FIG. 5 is a diagram showing an example of a data configuration of a regional infection information DB stored in the memory of the smart speaker;

FIG. 6 is a diagram explaining a voice recognition process that is performed by a data analyzer of the smart speaker;

FIG. 7 is a diagram showing an example of a data configuration of a regional infection information tabulation DB stored in a memory of the server;

FIG. 14 is a diagram showing an example of a data configuration of a regional infection information tabulation DB stored in a memory of the smart speaker according to Embodiment 2;

FIG. 15 is a flow chart showing an example of a process that is performed by the information providing system according to Embodiment 2 of the present disclosure;

FIG. 24 is a diagram showing an example of a data configuration of a mapping DB stored in a memory of a server;

DETAILED DESCRIPTION

Figure 1:
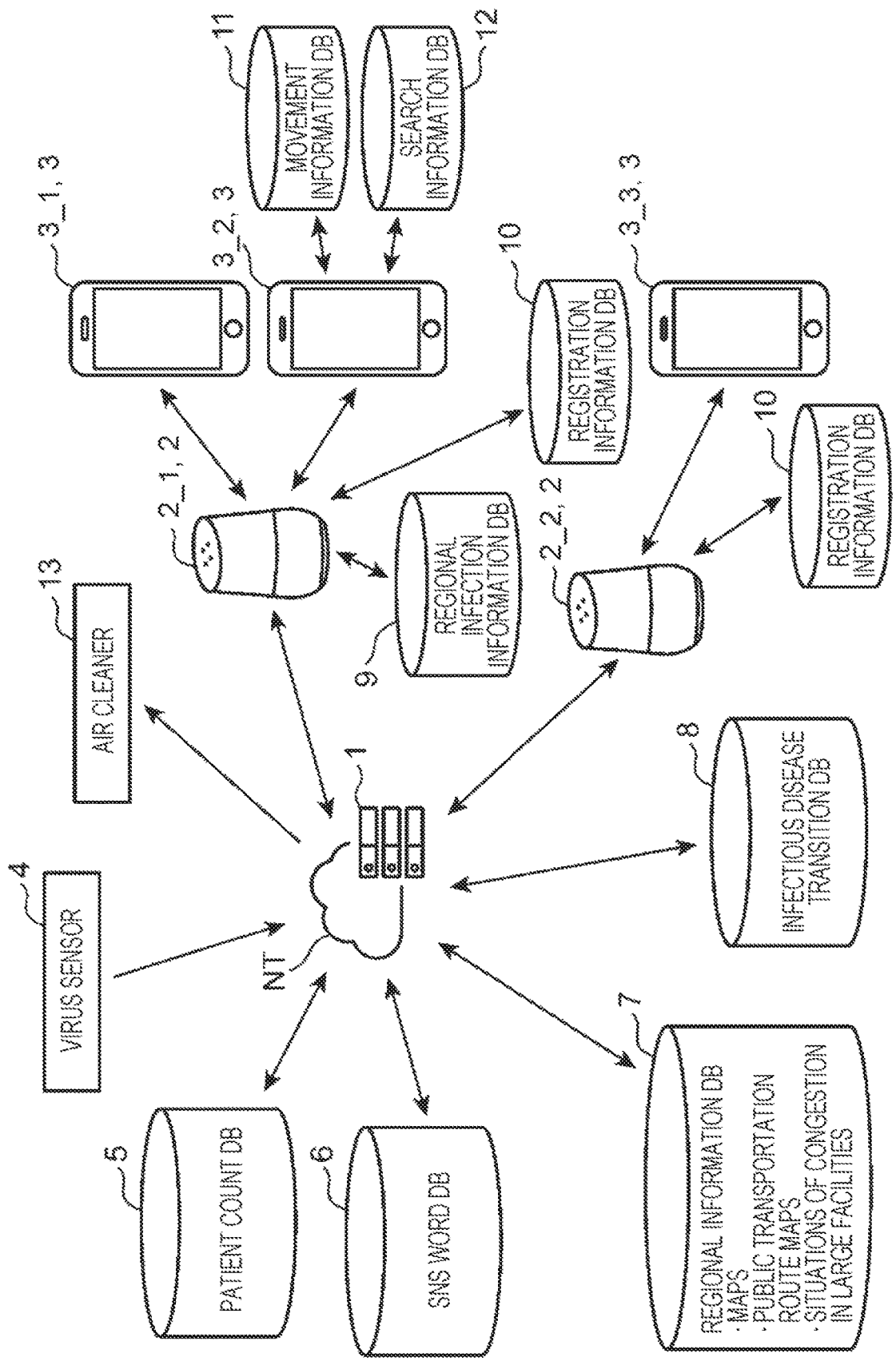
FIG. 1 is a diagram showing an example of a network configuration of an information providing system according to Embodiment 1 of the present disclosure.

Underlying Knowledge Forming Basis of the Present Disclosure

At the occurrence of an epidemic of an infectious disease such as influenza, patient data representing the numbers of infected persons by region is published by medical institutions such as hospitals and health centers, so a user can recognize the degrees of epidemicity of the infectious disease by region to a certain extent with reference to the patient data. However, this patient data often represents the numbers of patients counted about a week before the announcement and therefore undesirably lacks in timeliness. Therefore, countermeasures taken against the infectious disease after confirmation of the patient data are often already too late, and the patient data is insufficient in terms of curbing the epidemic of the infectious disease.

To address this problem, there has been a demand for a timely notification of the degrees of epidemicity of an infectious disease by region at the occurrence of an epidemic of the infectious disease or at the appearance of an omen of such an epidemic.

Incidentally, it is conceivable that at the occurrence of an epidemic of an infectious disease or at the appearance of an omen of an epidemic of an infectious disease, utterances such as "There is an epidemic of influenza in AA Elementary School" or "There seems to be an epidemic of influenza in a firm with which the company does business" may be exchanged at home. Therefore, collecting such utterances and analyzing their contents make it possible to accurately and timely identify risks of infection by region.

Given these circumstances, the inventor focused attention on smart speakers that have recently been coming into widespread use. Using these smart speakers makes it possible to collect a large number of utterances such as those mentioned above and accurately and timely identify risks of infection by region. Furthermore, this also makes it possible to provide users with appropriate information on the basis of the risks of infection thus identified.

The aforementioned Japanese Unexamined Patent Application Publication No. 2011-248802, which does not involve the use of a smart speaker, cannot collect utterances such as those mentioned above and therefore cannot accurately or timely acquire risks of infection by region.

Further, Japanese Unexamined Patent Application Publication No. 2011-248802 merely gives consideration to a place accessed by an infection monitoring system participant confirmed infected with a virus and gives no consideration to a risk of infection in the place accessed. Therefore, Japanese Unexamined Patent Application Publication No. 2011-248802 cannot provide a user with appropriate information according to a risk of infection, undesirably causing the user to take excessive countermeasures against the infectious disease or making the user take insufficient countermeasures against the infectious disease.

Meanwhile, the widespread proliferation of mobile terminals such as smartphones and tablet terminals has made it easy to identify positional information on users who possess mobile terminals. Therefore, tracking, from utterance contents, positional information on a large number of possibly-infected persons who are possibly infected with an infectious disease makes it possible to accurately and timely identify where and about how many possible-infected persons are present.

Moreover, presenting a user with information mapped with the number of possibly-infected persons in each place makes it possible to present the user with information for making a decision about whether to visit a particular place or whether to pass through the particular place and information for making a decision about what countermeasures to take against the infectious disease when visiting or passing though the particular place.

The aforementioned Japanese Unexamined Patent Application Publication No. 2011-248802, which does not involve the use of a smart speaker, cannot collect utterances such as those mentioned above and therefore cannot accurately or timely identify where and about how many possible-infected persons are present.

Further, Japanese Unexamined Patent Application Publication No. 2011-248802, which uses a result of a judgment made by a medical institution as to whether an infection monitoring system participant got infected with an infectious disease, does not track positional information on an infection monitoring system participant who has not received a diagnosis or treatment from a medical institution but is aware of being infected. Therefore, Japanese Unexamined Patent Application Publication No. 2011-248802 cannot accurately or timely identify where and about how many possibly-infected persons are present. As a result, Japanese Unexamined Patent Application Publication No. 2011-248802 undesirably causes a user to take excessive countermeasures against the infectious disease or makes a user take insufficient countermeasures against the infectious disease.

The present disclosure provides a technology with which to accurately and timely identify the region-by-region risk of infection of getting infected with an infectious disease and provide information appropriate for the prevention of the spread of the infectious disease.

In an aspect of the present disclosure, there is provided a method for providing information through an information providing system that provides information related to an infectious disease, the method including: acquiring, from one or more voice recognition devices connected to a computer of the information providing system via a network, regional infection information indicating one or more infection alert levels and one or more regions associated with the one or more infection alert levels, the one or more infection alert levels being obtained by the one or more voice recognition devices analyzing a voice signal; calculating, based on the regional infection information, an infection risk value representing a magnitude of a risk of infection in each of the one or more regions; and generating output information in accordance with the infection risk value for each of the one or more regions.

According to the present configuration, from one or more voice recognition devices connected via the network, regional infection information containing one or more infection alert levels obtained by the one or more voice recognition devices analyzing a voice signal and a region associated with the one or more infection alert level is acquired.

Moreover, an infection risk value representing the magnitude of a risk of infection in each region is calculated on the basis of the regional infection information thus acquired. Therefore, the present configuration makes it possible to collect a large number of pieces of regional infection information generated on the basis of utterances that are exchanged, for example, in a users house and accurately and timely identify an infection risk value by region.

In the foregoing aspect, the infection risk value may be calculated by calculating the number of reported cases for each of the one or more infection alert levels in each of the one or more regions, assigning, to the number of reported cases, a weight corresponding to the one or more infection alert levels, and evaluating the number of reported cases assigned the weight.

According to the present configuration, an infection risk value of each region is calculated by calculating the number of reported cases of the infectious disease for each infection alert level in each region from the regional infection information, assigning a weight to the number of reported cases thus calculated according to the infection alert level, and evaluating the number of reported cases assigned the weight. Therefore, the present configuration makes it possible to accurately calculate an infection alert level for each region.

In the foregoing aspect, the one or more infection alert levels may be estimated by the one or more voice recognition devices using a voice recognition content obtained by the one or more voice recognition devices analyzing the voice signal.

For example, an utterance such as "The class next door was temporarily closed" can be estimated to be larger in the number of infected persons and is therefore higher in risk of infection than an utterance such as "AA is absent from school because of influenza", and risks of infection can be sorted according to level. The present configuration makes it possible to sort the infection alert levels contained in the regional infection information according to level by judging from such utterance contents.

In the foregoing aspect, the method may further include acquiring the number of users in each of the one or more regions and an assumed duration of stay for which the users stay in each of the one or more regions. The infection risk value of each of the one or more regions may be calculated using a first correction coefficient of a region corresponding to the infection risk value, and the first correction coefficient may be a coefficient that increases the infection risk value of the corresponding region as at least one selected from the group consisting of the number of users in the corresponding region and the assumed duration of stay for which the users stay in the corresponding region increases.

The present configuration makes it possible to calculate the infection risk value to be higher as the region becomes larger in the number of users and the region becomes longer in the assumed duration of stay for which the users stay in the region, making it possible to obtain a more accurate infection risk value.

In the foregoing aspect, the method may further include acquiring, from a social network service server, information containing a regional infection word indicating an epidemic of the infectious disease in the one or more regions and a frequency of use of the regional infection word. The infection risk value of each of the one or more regions may be calculated using a second correction coefficient that increases the infection risk value of a region corresponding to the infection risk value as the frequency of use of the regional infection word in the region corresponding to the infection risk value becomes higher.

The present configuration makes it possible to, in a case where the occurrence of an epidemic of the infectious disease in a certain region has become a popular topic of conversation on a social network, reflect the popular topic in the infection risk value.

In the foregoing aspect, the method may further include acquiring patient count data representing the number of patients infected with the infectious disease in each of the one or more regions. The infection risk value of each of the one or more regions may be calculated using a third correction coefficient that increase the infection risk value of a region corresponding to the infection risk value as the number of patients in the region corresponding to the infection risk value increases.

The present configuration makes it possible to calculate the infection risk value in consideration of the number of patients infected with the infectious disease in a certain region.

In the foregoing aspect, the method may further include acquiring a measured value from a virus sensor installed in each of the one or more regions. The infection risk value of a region corresponding to the infection risk value may increase as the measured value of the virus sensor installed in the region corresponding to the infection risk value becomes larger.

The present embodiment makes it possible to calculate the infection risk value in consideration of the magnitude of a measured value of a virus sensor installed in a certain region.

In the foregoing aspect, the method further include, for each of the one or more regions, transmitting the output information via the network to a device existing in a region corresponding to the output information. The device may be a voice output device, and the output information may be a first control command that causes the voice output device to output a voice message serving as a notification of a risk of infection corresponding to the infection risk value.

In the present configuration, output information is generated for each region according to the infection risk value, and is transmitted to a device of a region corresponding to the output information. This makes it possible to provide the user with appropriate information according to the infection risk value, making it possible to avoid causing the user to take excessive countermeasures against the infectious disease or making the user take insufficient countermeasures against the infectious disease.

Further, the present configuration, in which a voice message corresponding to the infection risk value is outputted from the voice output device, allows the user to take measures needed to prevent infection with the infectious disease, making it possible to limit the spread of the infectious disease.

In the foregoing aspect, the method may further include, for each of the one or more regions, transmitting the output information via the network to a device existing in a region corresponding to the output information. The device may be an air cleaner, and the output information may be a second control command that brings the air cleaner into operation.

In the present embodiment, output information is generated for each region according to the infection risk value, and is transmitted to a device of a region corresponding to the output information. This makes it possible to provide the user with appropriate information according to the infection risk value, making it possible to avoid causing the user to take excessive countermeasures against the infectious disease or making the user take insufficient countermeasures against the infectious disease.

Further, the present configuration makes it possible to limit the spread of the infectious disease, for example, by transmitting a virus-removal control command to an air cleaner installed in a region whose infection risk value is high.

In an aspect of the present disclosure, there is provided a server of an information providing system that provides information related to an infectious disease, the server including: a communicator that acquires, from one or more voice recognition devices connected via a network, regional infection information indicating one or more infection alert levels and one or more regions associated with the one or more infection alert levels, the one or more infection alert levels being obtained by the one or more voice recognition devices analyzing a voice signal; and a processor that calculates, based on the regional infection information, an infection risk value representing a magnitude of a risk of infection in each of the one or more regions and generates output information in accordance with the infection risk value for each of the one or more regions.

In an aspect of the present disclosure, there is provided a voice recognition device that provides information associated with an infectious disease, the voice recognition device including: a microphone that detects an ambient sound and outputs a voice signal based on a detection result; a processor that executes a voice recognition process on the voice signal outputted by the microphone; a speaker; and a memory, wherein the processor extracts, from a result of the voice recognition process executed on the voice signal, first voice data containing at least one selected from the group consisting of a word and a sound related to a risk of infection and identifies an infection alert level from the first voice data, the processor extracts, from the result of the voice recognition process, second voice data corresponding to a sound detected by the microphone during a certain period of time before and after a time that the sound corresponding to the first voice data was detected by the microphone and identifies a region associated with the first voice data from the second voice data or identifies a region associated with the first voice data using movement history data representing a history of movements of an utterer of the first voice data, the processor generates regional infection information associating the region with the infection alert level and accumulates the regional infection information in the memory, and the processor generates a voice message corresponding to the infection alert level of the region from the regional infection information.

According to the present configuration, first voice data containing at least one selected from the group consisting of a word and a sound related to a risk of infection is extracted from a voice signal detected by the microphone, and an infection alert level is identified. Further, second voice data corresponding to a sound detected by the microphone during a certain period of time before and after the time that the sound corresponding to the first voice data was detected by the microphone, and a region associated with the first voice data is identified or a region associated with the first voice data is identified using movement history data on an utterer of the first voice data. Then, regional infection information generated by associating the infection alert level thus identified with the region thus identified is stored in the memory, and a voice message corresponding to the infection alert level is generated from the regional infection information thus accumulated.

Therefore, the present configuration makes it possible to collect regional infection information generated on the basis of utterances that are exchanged, for example, in a user's house and accurately and timely generate a voice message suited to an infection alert level by region.

Therefore, the present configuration makes it possible to provide the user with appropriate information according to the infection alert level, making it possible to avoid causing the user to take excessive countermeasures against the infectious disease or making the user take insufficient countermeasures against the infectious disease. It should be noted that an example of the sound contained in the first voice data is a sound, such as a sneeze or a cough, produced by the user.

In the foregoing aspect, the processor may estimate, from an utterance content of the first voice data, an infectious disease that is epidemic in the region or an infectious disease with which a particular person is infected.

According to the present configuration, in a case where the first voice data contains, for example, an utterance content such as "There is an epidemic of influenza in the BB District", it is estimated that there is an epidemic of influenza in the region concerned. Further, according to the present configuration, in a case where an utterance content such as "AA caught influenza" is contained, for example, it is estimated that a particular person got infected with influenza.

In the foregoing aspect, the processor may estimate, from an utterance content of the second voice data, a period during which a particular person is infected with an infectious disease, and correct the infection alert level using an estimation result.

For example, a person infected with influenza is expected to recover from influenza in about a week after infection. In the present configuration, a period of infection with the infectious disease is estimated from the utterance content of the second voice data, and an infection alert level is corrected from an estimation result, so that the infection alert level can be accurately identified.

In the foregoing aspect, when information for generating the regional infection information is insufficient, the processor may cause the speaker to output a question message, acquire a reply voice signal to the question message using the microphone, and generate the regional infection information using the reply voice signal.

According to the present configuration, with insufficient information to generate the regional infection information, a question message is outputted from the speaker, and the regional infection information is generated using the use's reply voice signal to the question message. This makes it possible to avoid as many situations as possible where the regional infection information cannot be generated.

In the foregoing aspect, the regional infection information may be information associating one or more regions including the region with one or more infection alert levels including the infection alert level, and the processor may calculate the number of reported cases of the infectious disease for each of the one or more infection alert levels in each of the one or more regions by classifying, for each of the one or more regions and each of the one or more infection alert levels, the regional infection information accumulated in the memory.

According to the present configuration, the number of reported cases of the infectious disease for each infection alert level in each region is calculated from the regional infection information thus acquired. Therefore, the present configuration makes it possible to accurately and timely identify an infection risk value by region.

In the foregoing aspect, the voice recognition device may further include a communicator that, for each of the one or more regions, transmits the output information via a network to a device existing in a region corresponding to the output information. The processor may use the communicator to acquire, from a social network service server, information containing a regional infection word indicating an epidemic of the infectious disease in each of the one or more regions and a frequency of use of the regional infection word and calculate an infection risk value for each of the one or more regions using a correction coefficient that increases the infection risk value as the frequency of use of the regional infection word becomes higher.

The present configuration makes it possible to, in a case where the occurrence of an epidemic of the infectious disease in a certain region has become a popular topic of conversation on a social network, reflect the popular topic in the infection risk value.

In the foregoing aspect, the memory may accumulate regional infection information generated by a different voice recognition device.

The present configuration makes it possible to calculate a more accurate infection risk value in cooperation with the different voice recognition device.

In the foregoing aspect, the voice recognition device may further include a communicator that, for each of the one or more regions, transmits the output information via a network to a device existing in a region corresponding to the output information. The device may be a different voice recognition device connected to the voice recognition device via the network, and the processor may generate a first control command that causes the different voice recognition device to output a voice message corresponding to the infection risk value, and transmit the first control command to the different voice recognition device.

Further, the present configuration, in which a voice message corresponding to the infection risk value is outputted from a different voice output device of a region in which there is an epidemic of the infectious disease, allows the user to take measures needed to prevent infection with the infectious disease, making it possible to limit the spread of the infectious disease.

In the foregoing aspect, the voice recognition device may further include a communicator that, for each of the one or more regions, transmits the output information via a network to a device existing in a region corresponding to the output information. The device may be an air cleaner, and the processor may generate a second control command that brings the air cleaner into operation, and transmit the second control command to the air cleaner.

The present configuration makes it possible to limit the spread of the infectious disease, for example, by transmitting a virus-removal control command to an air cleaner installed in a region whose infection risk value is high.

In an aspect of the present disclosure, there is provided a method for providing information through a voice recognition device that provides information associated with an infectious disease, the voice recognition device including a processor, the method including: extracting, from a sound detected by a microphone, first voice data containing at least one selected from the group consisting of a word and a sound related to a risk of infection; identifying an infection alert level from the first voice data; extracting second voice data from a sound detected by the microphone during a certain period of time before and after a time that the sound corresponding to the first voice data was detected by the microphone; identifying a region associated with the first voice data from the second voice data or identifying a region associated with the first voice data using movement history data representing a history of movements of an utterer of the first voice data; generating regional infection information associating the region with the infection alert level, and accumulating the regional infection information in a memory; and generating a voice message corresponding to the infection alert level from the region infection information.

In an aspect of the present disclosure, there is provided a non-transitory computer-readable recording medium storing a program for providing information through a voice recognition device that provides information associated with an infectious disease, the program causing a processor included in the voice recognition device to execute a method including: extracting, from a sound detected by a microphone, first voice data containing at least one selected from the group consisting of a word and a sound related to a risk of infection; identifying an infection alert level from the first voice data; extracting second voice data from a sound detected by the microphone during a certain period before and after a time that the sound corresponding to the first voice data was detected by the microphone; identifying a region associated with the first voice data from the second voice data or identifying a region associated with the first voice data using movement history data representing a history of movements of an utterer of the first voice data; generating regional infection information associating the region with the infection alert level, and accumulating the regional infection information in a memory; and generating a voice message corresponding to the infection alert level from the region infection information.

In an aspect of the present disclosure, there is provided a method for providing information through an information providing system, the information providing system including a voice recognition device and a server, the information providing system providing information related to an infectious disease, the method including: using the voice recognition device to phonetically recognize a voice signal based on a sound detected using a microphone, identify a possibly-infected person who is possibly infected with the infectious disease and a possibility of the possibly-infected person being infected with the infectious disease, and transmit, to a mobile terminal of the possibly-infected person, first infection information indicating the possibility of infection; using the mobile phone to transmit, to the server, coordinate data associating positional information on the mobile terminal with the first infection information; and using the server to generate mapping data using a plurality of pieces of coordinate data, transmitted from a plurality of mobile terminals including the mobile terminal, that include the coordinate data, the mapping data associating a particular place on map data with the number of possibly-infected persons in the particular place, and transmit the mapping data to the mobile terminal of the possibly-infected person or a mobile terminal of a person who is different from the possibly-infected person.

According to the present configuration, a possibly-infected person and a possibility of infection of the possibly-infected person being infected with the infectious disease are identified by the voice recognition device, and first infection information containing the possibility of infection is transmitted to a mobile terminal of the possibly-infected person. Further, upon receiving the first infection information, the mobile terminal transmits, to the server, coordinate data associating positional information on the mobile terminal with the infection information. This allows the server to acquire positional information on the possibly-infected person from the mobile terminal of the possibly-infected person, and to accurately and timely identify where and about how many possibly-infected persons are present, i.e. a risk of infection by region. Then, mapping data associating the place thus identified with the number of possibly-infected persons thus identified is transmitted to the mobile terminal. This allows the user of the mobile terminal, for example, to recognize about how many possibly-infected persons are present in a place he/she is going to visit, and to take appropriate countermeasures against the infectious disease.

In the foregoing aspect, the voice recognition device may estimate, from an utterance content of the voice signal, the infectious disease with which the possibly-infected person is infected.

According to the present configuration, for example, in a case where an utterance content such as "There is an epidemic of influenza", it is estimated that there is an epidemic of influenza in the region concerned.

In the foregoing aspect, the server may calculate an risk of infection in the particular place using the number of possibly-infected persons, and the mapping data may contain the risk of infection and advice information on infection preventive measures corresponding to the risk of infection.

The present configuration, in which a risk of infection in a particular place and advice information on infection preventive measures corresponding to the risk of infection are displayed on the mobile terminal, allows the user to visit the particular place with thoroughgoing measures against the infectious disease.

In the foregoing aspect, the mapping data may contain measurement data of a sensor that is installed in the particular place and that measures environmental information on the particular place.

The present configuration, in which information such as the presence or absence of a virus, humidity, and temperature in a particular place is displayed on the mobile terminal, makes it possible to provide the user with information for making a decision about what countermeasures to take against the infectious disease and information for making a decision about whether to visit the particular place.

In the foregoing aspect, the information providing system may further include an external server, the voice recognition device may identify, from the voice signal, a place associated with the infectious disease and an infection alert level for the place and transmit, to the external server, second infection information indicating the place and the infection alert level, the external server may receive a plurality of pieces of second infection information including the second infection information, calculate the number of reported cases of each of a plurality of infection alert levels in each of a plurality of places by classifying the plurality of pieces of second infection information for each of the plurality of places and each of the plurality of infection alert levels, the plurality of places being indicated by the plurality of pieces of second infection information and including the place, the plurality of infection alert levels being indicated by the plurality of pieces of second infection information and including the infection alert level, and calculate an infection risk value for each place by assigning, to the number of reported cases, a weight corresponding to each of the plurality of infection alert levels and evaluating the number of reported cases assigned the weight, the server may acquire the infection risk value for each of the plurality of places from the external server, and the mapping data may contain the infection risk value in each of the plurality of places.

The present configuration, in which an infection risk value in a particular place is displayed on the mobile terminal, makes it possible to provide the user with information for making a decision about what countermeasures to take against the infectious disease and information for making a decision about whether to visit the particular place.

In the foregoing aspect, the method may further include displaying a map image and the number of possibly-infected persons in the particular place superimposed on the map image.

The present configuration, in which the number of possibly-infected persons in a particular place is displayed on a map image, allows the user to easily recognize whether there is an epidemic of the infectious disease in the particular place.

In the foregoing aspect, the server may transmit the mapping data upon a request from the mobile terminal.

The present configuration makes it possible, for example, to, in a case where a user intending to go out to a certain place has asked the server to search for a route of movement, notify the user of a search result and the approximate number of possibly-infected persons around the route of movement. This makes it possible to present the user with information for making a decision about what countermeasures to take against the infectious disease.

In an aspect of the present disclosure, there is provided an information providing system that provides information related to an infectious disease, the information providing system including: a voice recognition device; a plurality of mobile terminals; and a server, wherein the voice recognition device phonetically recognizes a voice signal based on a sound detected using a microphone, identifies a possibly-infected person who is possibly infected with the infectious disease and a possibility of the possibly-infected person being infected with the infectious disease, and transmits, to one of the plurality of mobile terminals that belongs to the possibly-infected person, first infection information indicating the possibility of infection, upon receiving the first infection information, the mobile terminal of the possibly-infected person transmits, to the server, coordinate data associating positional information on the mobile terminal of the possibly-infected person with the first infection information, and the server generates mapping data using a plurality of pieces of coordinate data, transmitted from the plurality of mobile terminals, that include the coordinate data, the mapping data associating a particular place on map data with the number of possibly-infected persons in the particular place.

In still another aspect of the present disclosure, there is provided a mobile terminal of an information providing system that provides information related to an infectious disease, the mobile terminal including: a communicator that receives, from a server, mapping data associating a particular place on map data, the number of possibly-infected persons in each place, a risk of infection in each place, and advice information on infection preventive measures corresponding to the risk of infection with one another; and a controller that uses the mapping data to generate a display screen by associating the number of possibly-infected persons, the risk of infection, and the advice information with one another in each place and displays the display screen on a display unit.

In still another aspect of the present disclosure, there is provided an apparatus that provides information associated with an infectious disease, the apparatus including: a processor that executes a word recognition process on an input signal inputted to the apparatus; a display unit; and a memory, wherein the processor includes an infection alert level identifier that extracts, from a result of the word recognition process executed on the input signal, first word data containing a word related to a risk of infection and identifies an infection alert level from the first word data, a region identifier that extracts second word data from a result of a word recognition process executed on an input signal during a certain period of time before and after a time that the input signal corresponding to the first word data was obtained and identifies a region associated with the first word data from the second word data or identifies a region associated with the first word data using movement history data representing a history of movements of the apparatus, a regional infection information generator that generates regional infection information associating the region thus identified with the infection alert level thus identified and accumulates the regional infection information in the memory, and an output information generator that generates a message corresponding to the infection alert level of the region from the regional infection information thus accumulated, and the display unit displays the message.

The present disclosure can also be implemented as a computer program that causes a computer to execute each of the characteristic steps of such a method or a server that operates on such a computer program. Further, such a computer program can of course be circulated via a non-transient computer-readable recording medium such as a CD-ROM or a communication network such as the Internet.

It should be noted that the embodiments to be described below each illustrate a specific example of the present disclosure. The numerical values, shapes, constituent elements, steps, orders of steps, and the like that are shown in the following embodiments are merely examples and are not intended to limit the present disclosure. Further, those of the constituent elements in the following embodiments which are not recited in an independent claim representing the most generic concept are described as optional constituent elements. Further, the content of each of the embodiments may be combined with that of another embodiment.

Embodiment 1

FIG. 1 is a diagram showing an example of a network configuration of an information providing system according to Embodiment 1 of the present disclosure. In a service coverage region including a region of residence of a user to which a service is applied and one or more regions located within a certain range from the region, the information providing system serves to calculate, for each region, the risk of the user getting infected with an infectious disease and, on the basis of a result of the calculation, provide the user with various services to prevent the user from getting infected with the infectious disease. The term "region" here encompasses a district and a place. The term "district" refers to one of a plurality of areas, such as cities, towns, and villages, into which the service coverage region is divided on the basis of a predetermined criterion such as a geographical factor. The term "place" refers to the places of facilities, such as commercial facilities, hospitals, and elementary schools, included in the region. The term "infectious disease" refers to diseases, such as cold, influenza, dysentery, malaria, and a norovirus disease, that are caused by a pathogen proliferating through invading an organism.

The information providing system includes a server 1, smart speakers 2 (each of which is an example of the voice recognition device and the device), mobile terminals 3, a virus sensor 4, a patient count DB (database) 5, an SNS word DB 6, a regional information DB 7, an infectious disease transition DB 8, an regional infection information DB 9, registration information DBs 10, a movement information DB 11, a search information DB 12, and an air cleaner 13 (which is an example of the device).

All of these components from the server 1 to the air cleaner 13 are communicably connected to one another via a network NT. The network NT encompasses, for example, an Internet communication network, a mobile phone communication network, and the like.

The server 1 is for example a cloud server constituted by one or more computers, and calculates an infection risk value for each region using regional infection information acquired from the smart speakers 2.

Each of the smart speakers 2 is installed, for example, in a user's house. The smart speaker 2, which is also called "AI speaker", is a device that collects, with a microphone, utterances exchanged at home, phonetically recognizes a voice signal obtained by collecting sounds, and provides the user with various services using a voice recognition result. The smart speaker 2 is an example of the voice recognition device and the voice output device. In the example shown in FIG. 1, two smart speakers 2_1 and 2_2 are illustrated; however, this is merely an example, and the number of smart speakers 2 may be 1 or may be not smaller than 3.

Each of the mobile terminals 3 is a device that is possessed by a user living in a house in which a smart speaker 2 is installed. The mobile terminal 3 is constituted, for example, by a portable information processing device such as a smartphone, a tablet terminal, or a push-button mobile phone. In the example shown in FIG. 1, three mobile terminals 3_1, 3_2, and 3_3 are illustrated; however, this is merely an example, and the number of mobile terminals 3 may be 1, may be 2, or may be not smaller than 4.

The virus sensor 4 is constituted, for example, by a sensor that detects viruses such as the influenza virus and norovirus.

The patient count DB 5 stores patient count data representing a distribution of the numbers of infected patients by region. The patient count data is data that is generated by medical institutions such as hospitals and health centers and, for example, is data that, at the occurrence of an epidemic of an infectious disease, is generated to encourage local residents to take countermeasures against the infectious disease. Note, however, that since the numbers of patients contained in the patient count data usually show the numbers of patients counted a certain period of time after (e.g. one week after) the occurrence of an epidemic of the infectious disease, the patient count data has a drawback of lacking in timeliness. The patient count DB 5 is a database assembled on a medical institution server administered by a medical institution, and is connected to the network NT via the medical institution server.

The SNS (social network service) word DB 6 is a database that stores associations between words that have become popular topics of conversation on SNSs and time shifts in frequency of use of those words. For example, in a case where there is an epidemic of influenza in the AA District and therefore the frequency of use of "influenza" in association with "AA District" on an SNS has exceeded a certain value, the SNS word DB 6 stores a time shift in frequency of use regarding a regional infection word, such as "AA District-influenza", associating a place with an infectious disease. The SNS word DB 6 is for example a database assembled on an SNS administration server administered by an SNS administrator, and is connected to the network NT via the SNS administration server.

The regional information DB 7 stores geographical data, route map data representing public transportation route maps, and congestion situation data representing situations of congestion in large facilities within the service coverage region. Examples of large facilities include civic centers, libraries, swimming pools, commercial facilities, and the like. The regional information DB 7 is for example a database assembled on an administration server administrated by an administrator of the information providing service, and is connected to the network NT via the administration server. Geographical data contained in regional data is stored in the regional information DB 7, for example, by the administration server importing geographical data provided by a search engine operator on the Internet. Further, public transportation route map data contained in the regional data is stored in the regional information DB 7, for example, by the administration server importing route map data disclosed on the Internet by railroad companies, bus companies, and the like. Further, congestion situation data contained in the regional data is stored in the regional information DB 7, for example, by the administration server importing congestion situation data generated by a search engine operator on the Internet.

The infectious disease transition DB 8 stores infectious disease transition data representing, by type and region, how infectious diseases changed from one form or state to another in the past. The infectious disease transition data stores, by type and region, the numbers of patients at the occurrence of epidemics of infectious diseases in the past and the dates of the epidemics. The infectious disease transition DB 8 is for example a database that is assembled on the medical institution server, and is connected to the network NT via the medical institution server.

The regional infection information DB 9 is created on the basis of histories of utterances of users phonetically recognized by a smart speaker 2, and stores regional infection information representing an infection alert level for each region. Each of the registration information DBs 10 stores personal information on constituent members living in a house in which a smart speaker 2 is installed. The regional infection information DB 9 and the registration information DB 10 are stored, for example, in a memory of the smart speaker 2. Note, however, that this is merely an example and the regional infection information DB 9 and the registration information DB 10 may be stored in an external server.

The movement information DB 11 stores movement information on a user who possesses a mobile terminal 3. The movement information is for example data associating positional information calculated by a GPS sensor of the mobile terminal 3 with the time of calculation. The movement information DB 11 is stored in a memory of the mobile terminal 3. Note, however, that this is merely an example and the movement information DB 11 may be stored in the external server.

The search information DB 12 stores search information representing a history of searches done by the user on a search engine that is executed on the mobile terminal 3. The search information is for example data associating a search word entered into the search engine with the time of search.

The air cleaner 13 is installed in the service coverage region, and operates in accordance with a second control command that is transmitted from a corresponding smart speaker 2. For example, at the occurrence of an epidemic of an infectious disease in the region in which the air cleaner 13 is installed, the air cleaner 13 operates in accordance with a second control command from a smart speaker 2 installed in the region and prevents the spread of the infectious disease by purifying ambient air.

Figure 2:
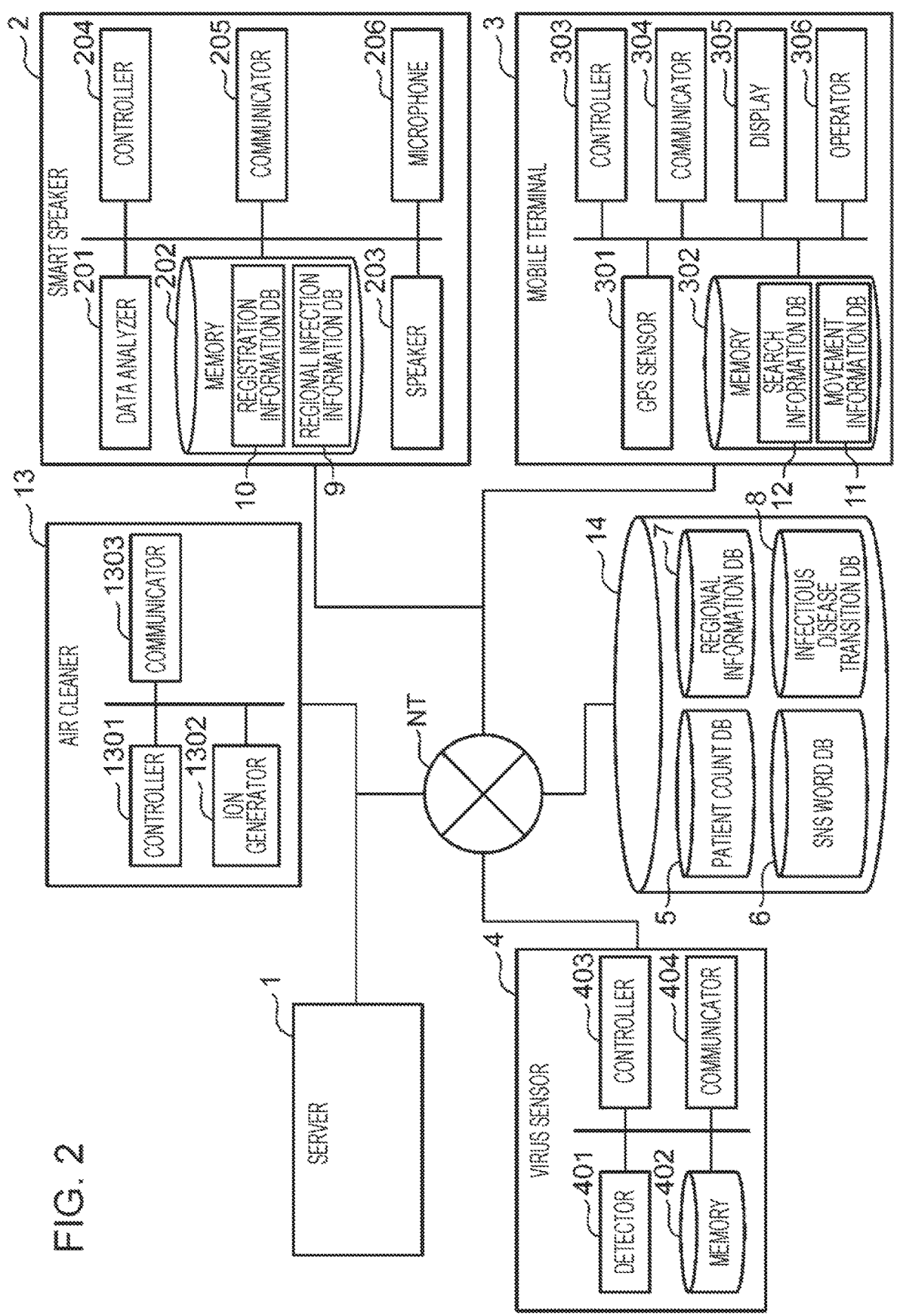
FIG. 2 is a block diagram showing an example configuration of the information providing system shown in FIG. 1.

FIG. 2 is a block diagram showing an example configuration of the information providing system shown in FIG. 1. Each of the smart speakers 2 includes a data analyzer 201, a memory 202, a speaker 203, a controller 204, a communicator 205, and a microphone 206. The data analyzer 201 is constituted by a processor that performs a voice recognition process on a voice signal obtained by the microphone 206 collecting sounds.

Note here that the data analyzer 201 extracts, from a voice signal obtained by the microphone 206 collecting sounds, first voice data containing at least one selected from the group consisting of a word and a voice signal related to a risk of infection and identifies an infection alert level from the first voice data. Then, the data analyzer 201 extracts second voice data from a voice signal obtained by the microphone 206 collecting sounds during a certain period of time before and after the time that the first voice data was obtained by the microphone 206 collecting sounds and identifies a region associated with the first voice data from the second voice data. Alternatively, the data analyzer 201 identifies a region associated with the first voice data using movement information on an utterer of the first voice data. Then, the data analyzer 201 generates regional infection information by associating the region thus identified with the infection alert level thus identified.

The infection alert level is data that numerically expresses a degree of epidemicity of an infectious disease, and the data is obtained by analyzing a voice signal, contained in the first voice data, that represents a cough or a sneeze or an utterance content represented by the first voice data. As a certain period of time before and after the time that the first voice data was obtained by collecting sounds, the duration of a series of conversations that users exchange regarding the infectious disease is adopted, and for example, a value such as ten seconds, thirty seconds, or one minute is adopted.

The memory 202 is constituted, for example, by a semiconductor memory, and stores the registration information DB 10 and the regional infection information DB 9. The registration information DB 10 and the regional infection information DB 9 will be described in detail later.

The speaker 203 outputs a voice message under control of the controller 204.

The controller 204 is constituted, for example, by a CPU, and exercises overall control of the smart speaker 2. The communicator 205 is constituted by a communication device through which the smart speaker 2 is connected to the network NT. For example, the communicator 205 transmits, to the server 1, regional infection information generated by the data analyzer 201. The microphone 206 collects ambient sounds and converts them into a voice signal.

Each of the mobile terminals 3 includes a GPS sensor 301, a memory 302, a controller 303, a communicator 304, a display unit 305, and an operator 306. The GPS sensor 301 periodically calculates the position of the smartphone.

The memory 302 is constituted, for example, by a semiconductor memory, and stores the search information DB 12 and the movement information DB 11.

The controller 303 is constituted, for example, by a CPU, and exercises overall control of the mobile terminal 3. For example, the controller 303 generates movement information by associating a position calculated by the GPS sensor 301 with the time of calculation, and stores the movement information in the movement information DB 11. Further, the controller 303 generates search information by associating a search word entered into a search engine by operating the operator 306 with the time of search, and stores the search information in the search information DB 12.

The communicator 304 is constituted by a communication device that connects the mobile terminal 3 to the network NT. The display unit 305 is constituted by a display device such as a liquid crystal panel, and displays various images under control of the controller 303. For example, the display unit 305 displays an image of a search engine.

The operator 306 is constituted, for example, by a touch panel, and accepts various operations that are entered by the user. For example, the operator 306 accepts an operation of entering a search word.

The virus sensor 4 includes a detector 401, a memory 402, a controller 403, and a communicator 404. The detector 401 includes, for example, a light source that applies light to a sample to which at least one selected from the group consisting of sialic acid and gold nanoparticles have been added, a light-receiving element that detects the wavelength and reflectance (transmittance) of light that vary depending on the presence or absence of a virus, and a processor that determines the presence or absence of a virus using a detection result yielded by the light-emitting element.

The memory 402 is constituted, for example, by a semiconductor memory, and stores a result of detection of a virus by the detector 401.

The controller 403 is constituted, for example, by a CPU, and exercises overall control of the virus sensor 4. The communicator 404 is constituted by a communication device that connects the virus sensor 4 to the network NT.

The air cleaner 13 includes a controller 1301, anion generator 1302, and a communicator 1303. The controller 1301 is constituted, for example, by a CPU, and exercises overall control of the air cleaner 13. The ion generator 1302 generates ions in the air to inactivate the virus. The communicator 1303 is constituted by a communication device that connects the air cleaner 13 to the network NT.

A database group 14 is a compilation of the patient count DB 5, the SNS word DB 6, the regional information DB 7, and the infectious disease transition DB 8, which are shown in FIG. 1, and is assembled on the various servers described with reference FIG. 1.

Figure 3:
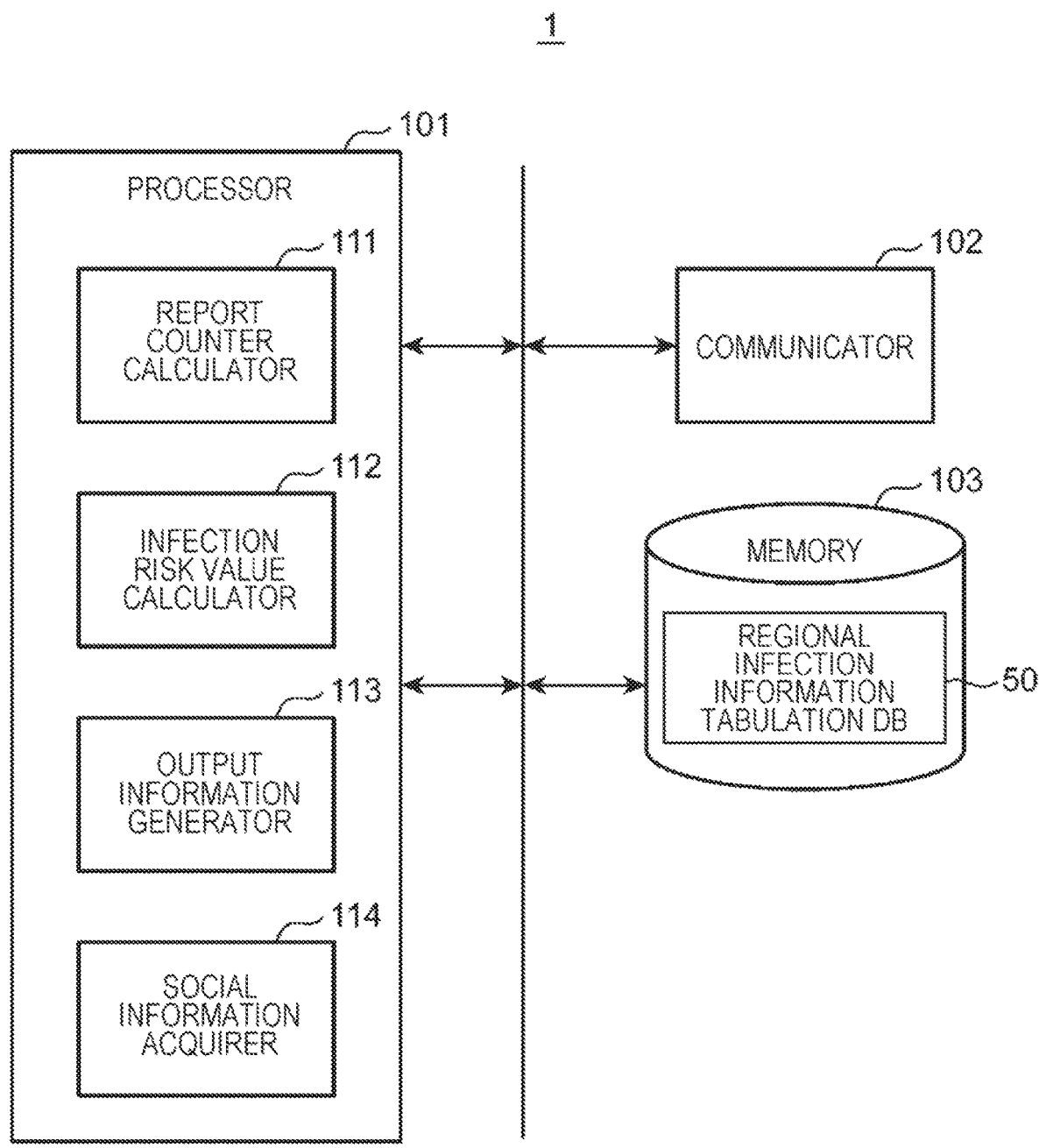
FIG. 3 is a block diagram showing an example configuration of a server shown in FIG. 2.

FIG. 3 is a block diagram showing an example configuration of the server 1 shown in FIG. 2. The server 1 includes a processor 101, a communicator 102, and a memory 103. The processor 101 is constituted, for example, by a CPU, and includes a reported case count calculator 111, an infection risk value calculator 112, an output information generator 113, and a social information acquirer 114. All of these components from the reported case count calculator 111 to the social information acquirer 114 are implemented by the processor 101 executing a control program, stored in the memory 103, that causes a computer to function as the server 1.

The reported case count calculator 111 calculates the number of reported cases of an infectious disease for each infection alert level in each region by classifying, for each region and each infection alert level, regional infection information that the communicator 102 received from a smart speaker 2.

The infection risk value calculator 112 assigns, to the number of reported cases calculated by the reported case count calculator 111, a weight corresponding to the infection alert level and calculates an infection risk value of each region by evaluating the number of reported cases assigned the weight. The term "infection risk value" here refers to an index that indicates the magnitude of a risk of infection with the infectious disease in each region.

The output information generator 113 generates output information from the infection risk value of each region as calculated by the infection risk value calculator 112 and transmits the output information to a device of the region concerned through the communicator 102. An adoptable example of the output information is a first control command that causes a smart speaker 2 installed in a region determined to be high in infection risk value to output a voice message. The first control command contains the voice message that the smart speaker 2 is made to output.

The social information acquirer 114 acquires a regional infection word and a time shift in frequency of use of the regional infection word from the SNS word DB 6 through the communicator 102. The memory 103 is constituted, for example, by a semiconductor memory, and stores a regional infection information tabulation DB 50. The regional infection information tabulation DB 50 will be described in detail later.

FIG. 4 is a diagram showing an example of a data configuration of a registration information DB 10 stored in the memory 202 of a smart speaker 2. The registration information DB 10 contains a basic information table T11 and a registration information table T12.

The basic information table T11 is a table storing the place of installation of and the contents of settings for the smart speaker 2. Specifically, the basic information table T11 stores "Smart Speaker ID", "Place of Installation", "Announcement Setting", "Announcement District Setting", and "Device Control Setting". The "Smart Speaker ID" represents an identifier uniquely assigned to the smart speaker 2 entered. The "Place of Installation" is the place of installation of the smart speaker 2. In this example, the address of the house in which the smart speaker 2 is installed is adopted. The "Announcement Setting" represents configuration information indicating whether to, upon receiving a first control command from the server 1, cause the smart speaker 2 to output a voice message. For example, upon receiving a first control command from the server 1 in a case where the announcement setting is ON, the smart speaker 2 outputs a voice message contained in the first control command. On the other hand, when the smart speaker 2 has received a first control command from the server 1 in a case where the announcement setting is OFF, the smart speaker 2 does not output a voice message contained in the first control command.

The "Announcement District Setting" represents information indicating whether to share regional infection information stored in the regional infection information DB 9 with a smart speaker 2 installed in an associated district. In a case where the announcement district setting is set to "Associated District Included", the smart speaker 2 shares the regional infection information with a smart speaker 2 installed in the same district or a predetermined associated district.

The "Device Control Setting" represents configuration information indicating whether to, upon receiving a first control command from the server 1, transmit to a corresponding air cleaner 13 a second control command that brings the corresponding air cleaner 13 into operation. For example, if the device control setting is "Automatic", the smart speaker 2 transmits the second control command to the corresponding air cleaner 13. On the other hand, if the device control setting is not "Automatic", the smart speaker 2 does not transmit the second control command to the corresponding air cleaner 13. Note here that the corresponding air cleaner 13 is an air cleaner 13 provided in the region in which the smart speaker 2 is installed, and refers to an air cleaner 13 associated in advance with the smart speaker 2. For example, if the smart speaker 2 is installed in a house, the corresponding air cleaner 13 is an air cleaner 13 installed in the house.

The registration information table T12 is a table storing personal information on constituent members living in the house in which the smart speaker 2 is installed. The registration information table T12 is a table storing one piece of registration information in one record. The registration information stores "No.", "User", "First Designation" "Second Designation", "Third Designation", "Voiceprint Registration No.", "Age", "Sex", "Place of Frequent Visit 1", "Level of Frequent Visit 1", "Reference Duration of Stay 1", "Place of Frequent Visit 2", "Level of Frequent Visit 2", "Reference Duration of Stay 2", "Disease Information", "Associated Designation", and "Relationship" in association with one another.

The "No. (Number)" represents identifiers of the constituent members. The "User" Column stores the names of the constituent members. Since this family is constituted by four constituent members, the "User" Column stores the names of these four constituent members. The "First Designation", the "Second Designation", and the "Third Designation" represent the respective nominal designations of the constituent members in the family. The "First Designation" to "Third Designation" represent the nominal designation of each constituent member by the other constituent members or the self-designation of each constituent member in the family. In the family, there are wide variations in designation depending, for example, on relationships between persons who speak and persons who are spoken to. Therefore, in this example, to deal with the wide variations, the registration information table T12 stores the three designations, namely the "First Designation" to "Third Designation".

The "Voiceprint Registration No. (Number)" represents an index of voiceprint data of each constituent member. Since the voiceprint data of each constituent member is stored in association with the voiceprint registration No. in advance in the memory 202, the voiceprint data of the constituent member concerned is read out from the memory 202 with the voiceprint registration No. as a key. The "Age" represents the age of each constituent member, and the "Sex" represents the sex of each constituent member. The "Place of Frequent Visit 1" represents a place, such as a workplace or a school, that each constituent member visits most frequently. The "Level of Frequent Visit 1" is data that numerically expresses the degree to which each constituent member visits the place of frequent visit 1. In this example, the number of visits per week is adopted as the "Level of Frequent Visit 1". Specifically, the "Level of Frequent Visit 1" is configured such that a place that is visited seven days per week is set to "5", that a place that is visited four to six days per week is set to "4", that a place that is visited two to three days per week is set to "3", that a place that is visited one day per week is set to "2", and that a place that is not visited every week but visited twice or more per month is set to "1". The same applies to the "Level of Frequent Visit 2".

The "Reference Duration of Stay 1" represents the reference duration of stay for which each constituent member stays in the place of frequent visit 1. The "Place of Frequent Visit 2" represents a place that each constituent member visits second most frequently after the place of frequent visit 1. The "Level of Frequent Visit 2" and the "Reference Duration of Stay 2" represent the level of frequent visit to the place of frequent visit 2 and the reference duration of stay in the place of frequent visit 2, respectively.

The "Disease Information" represents a disease, such as metabolic syndrome (MetS) or atopic dermatitis (atopy), from which each constituent member suffers. The "Associated Designation" represents a designation of each constituent member outside the family (e.g. in a company, a school, or other places). The "Relationship" represents a relationship between a person, such as a superior or a friend, who calls each constituent member by an associated designation and that constituent member.

In FIG. 4, the "User", the "First designation" to "Third designation", the "Age", "Sex", the "Disease Information", the "Associated Designation", and the "Relationship" are data entered in advance, for example, by a user by means of an input device or voices. The "Voiceprint Registration No." is data assigned in a voiceprint registration phase. The "Place of Frequent Visit 1", the "Level of Frequent Visit 1", and the "Reference Duration of Stay 1" may be entered by a user by means of an input device or voices, or may be identified using movement information stored in the movement information DB 11. The same applies to the "Place of Frequent Visit 2", the "Level of Frequent Visit 2", and the "Reference Duration of Stay 2". It should be noted that each piece of information registered in the registration information table T12 may be information automatically registered by machine learning of voices acquired by the smart speaker 2.

FIG. 5 is a diagram showing an example of a data configuration of the regional infection information DB 9 stored in the memory 202 of the smart speaker 2. The regional infection information DB 9 is a database, created on the basis of utterances of the constituent members living in the house in which the smart speaker 2 is installed, that stores regional infection information containing infection alert levels by region. The regional infection information DB 9 stores one piece of regional infection information in one record. Regional infection information is information generated for each voice recognition result, and contains "Time", "Detection", and "Analysis Result".

The "Time" represents a phonetically-recognized time such as 7:00 01/18/2018 (7 o'clock on Jan. 18, 2018). The "Detection" represents voice recognition results, and contains "Content" and "Source". The "Content" represents the contents of the voice recognition results (voice recognition contents). The "Content" is constituted by data obtained by converting into text an utterance content such as "I heard that the client I met at work yesterday had the flu", for example, if a voice recognition content is an utterance. Further, the "Content" is constituted by data such as a "coughing sound" or a "sneezing sound", for example, if a voice recognition content is a sound such as a cough or a sneeze. The "Source" represents sources of utterance of the voice recognition contents. In this example, the "Source" Column stores the identifiers of the constituent members and the classes of the contents as in the case of "No. 1/Sound Production". As the identifiers of the constituent members, the identifiers of the constituent members as stored in the registration information table T12 are adopted. For example, the identifier of Taro is No. 1, and the identifier of Hanako is No. 2.

The classes of the contents represent the classes of the voice recognition contents and, in this example, include "Sound Production" and "Search". The "Sound Production" indicates that a voice recognition content is an utterance of a constituent member or a coughing sound or sneezing sound of a constituent member. The "Search" indicates that a voice recognition content is a search request made to the smart speaker 2 by a constituent member.

The "Analysis Result" represents results of analyses of the voice recognition contents, and contains "Place", "District", "Infection Alert Level", "Estimated Name of Infectious Disease", "Epidemic Period Correction Value", "Subject No. (Number)", "Possibility of Infection", and "Ancillary Data".

The "Place" represents epidemic places, estimated from the voice recognition contents, where there are epidemics of infectious diseases. The "District" represents districts to which the estimated epidemic places belong. The "Infection Alert Level" is data that numerically expresses the degrees of epidemicity of the infectious diseases as estimated from the voice recognition contents. In this example, the infection alert level takes on a larger value from among numerical values of 1 to 5 as the degree of epidemicity of an infectious disease becomes higher.

For example, if a voice recognition content is a content indicating a large number of (e.g. two or more) infected persons, the infection alert level is set to "5". Further, if a voice recognition content is such a content that the presence of at least one infected person can be identified although the number of infected persons cannot be identified, the infection alert level is set to "4". Further, if a voice recognition content is a content containing information related to an infectious disease whose name cannot be identified, the infection alert level is set to "3". Further, if a voice recognition content is a content indicating an early symptom (such as a coughing sound or sneezing sound) of an infectious disease, the infection alert level is set to "2". Further, if a voice recognition content is a content indicating growing concern over an infectious disease, the infection alert level is set to "1".

The regional infection information may be created using messages and search words typed into multi-devices. The multi-devices set infection alert levels from the words typed, identify regions from words or positional information data entered before or after the time that words corresponding to set infection alert levels were typed, and associate the infection alert levels with the regions.

The multi-devices are for example mobile terminals or personal computers, and have message sending functions and/or search functions involving the use of search engines.

The "Estimated Name of Infectious Disease" represents the names of infectious diseases, such as influenza and cold, as estimated from the voice recognition contents. The "Epidemic Period Correction Value" is a correction coefficient for an infection alert level in consideration of an epidemic period of an infectious disease. For example, if the infectious disease is influenza, it is usual to recover from the infectious disease in about a week. Accordingly, as an epidemic period of an infectious disease as estimated from a voice recognition content further dates back to the past from the current point of time, the epidemic period correction value is set to a lower value within a range of 0 to 1. In this example, in a case where an epidemic period of an infectious disease as estimated from a voice recognition content dates back one week or shorter or is unknown, the epidemic period correction value is set to "1". Further, if an epidemic period of an infectious disease as estimated from a voice recognition content dates back two weeks or shorter, the epidemic period correction value is set to "0.75". Further, if an epidemic period of an infectious disease as estimated from a voice recognition content dates back one month or shorter, the epidemic period correction value is set to "0.5". Further, if an epidemic period of an infectious disease as estimated from a voice recognition content dates back one and a half months or shorter, the epidemic period correction value is set to "0.25". Further, if an epidemic period of an infectious disease as estimated from a voice recognition content dates back one and a half months or longer to the past, the epidemic period correction value is set to "0".

A final value of the infection alert level is calculated by multiplication by the correction value represented by the epidemic period correction value.

The "Subject No." represents identifiers of constituent members estimated from the voice recognition contents to be infected with an infectious disease, and in this example, the identifiers of the constituent members are adopted. The "Possibility of Infection" represents possibilities, estimated from the voice recognition contents, that the constituent members stored in the "Subject No." Column may be infected with an infectious disease.

In this example, the possibility of infection takes on a larger value from among numerical values of 1 to 6 as the possibility of a constituent member being infected with an infectious disease becomes higher. Specifically, in a case where a constituent member can be determined with certainty to be an infected person, the possibility of infection is set to "6". Further, in a case where a constituent member has possibly had close contact with an infected person, the possibility of infection is set to "5". Further, if the duration of stay for which a constituent member stayed in an epidemic place where there was an epidemic of an infectious disease is a long period of time (e.g. four hours or longer), the possibility of infection is set to "4". Further, if the duration of stay for which a constituent member stayed in an epidemic place where there was an epidemic of an infectious disease is a short period of time (e.g. three hours or longer and shorter than four hours), the possibility of infection is set to "3". Further, in a case where the duration of stay cannot be identified but a constituent member can be estimated to have visited an epidemic place where there was an epidemic of an infectious disease or a case where the duration of stay for which a constituent member stayed in an epidemic place where there was an epidemic of an infectious disease is shorter than three hours, the possibility of infection is set to "2". Further, in a case where the possibility of a constituent member being infected with an infectious disease is low, the possibility of infection is set to "1".

The "Ancillary Data" Column has stored therein movement information indicating routes of movement of the constituent members registered in the "Subject No." Column. The movement information can be acquired from the movement information DB 11, provided the constituent member concerned possesses a mobile terminal 3. Therefore, in this example, ancillary data is registered about "Taro", who possesses a mobile terminal 3, but no ancillary data is registered on the other constituent members. In the "Ancillary Data" Column, the phrase "Movement Information/Smartphone" indicates that the device from which the movement information was acquired is a mobile terminal 3. Further, as the movement information registered in the "Ancillary Data", movement information over the past period based on the "Time" of the voice recognition contents is adopted. Storing movement information in this way makes it possible to identify a region that a constituent member with a high possibility of infection dropped by and reflect the region in the calculation of an infection risk value in the region.

FIG. 6 is a diagram explaining a voice recognition process that is performed by the data analyzer 2 of the smart speaker 2. First, the data analyzer 201 phonetically recognizes a voice signal obtained by the microphone 206 collecting sounds. In this example, as indicated in the first row of the regional infection information DB 9, the voice recognition content "I heard that the client I met at work yesterday had the flu" is obtained, for example. Further, an utterer of this utterance is identified by using voiceprint data. In the example in the first row, "Taro" of "No. 1" is identified as the utterer.

Next, the data analyzer 201 extracts, out of the voice recognition content, first voice data containing a disease name word (i.e. a word related to a risk of infection).

In the example shown in the first row, the phrase "had the flu", which contains a disease name word, is extracted as the first voice data. Next, the data analyzer 201 identifies an infection alert level from the utterance of the first voice data. In the example shown in the first row, the infection alert level is set to "4", as it can be estimated from the utterance content of the phrase "had the flu", which is the first voice data, that at least one person got infected with influenza.

Next, the data analyzer 201 extracts second voice data from a voice signal obtained by the microphone 206 collecting sounds during a certain period of time before and after the time that the first voice data was obtained by collecting sounds. In the example shown in the first row, the clause "the client I met at work yesterday", which was uttered during a certain period of time before the first voice data "had the flu", is extracted as the second voice data.

Next, the data analyzer 201 identifies a place associated with the first voice data from the second voice data. In the example shown in the first row, since the clause "the client I met at work yesterday" contains a place word "work", the word "work" is extracted.

In this example, the utterer is "Taro", and in the registration information DB 10, the "AB Corporation", for which Taro works, is stored as the "Place of Frequent Visit 1" for "Taro". Therefore, the "AB Corporation" is identified from the second voice data as the place associated with the first voice data. As a result, the "AB Corporation" is stored in the "Place" Column. Further, since the location of the "AB Corporation" belongs to the "BB District", the "BB District" is stored in the "District" Column. Note here that the data analyzer 201 needs only refer to the geographical data contained in the regional information DB 7 to identify the "District" to which the "Place" belongs.

Next, the data analyzer 201 identifies a date and time word and a person word from the second voice data. In the example shown in the first row, since the second voice data "the client I met at work yesterday" contains a date and time word "yesterday" and a person word "the client I met", the words "yesterday" and "the client I met" are identified.

In the example shown in the first row, since the time of voice recognition is 7 o'clock on Jan. 18, 2018 and the date and time word is "yesterday", "Jan. 17, 2018" is identified as a date and time associated with the first voice data. Note here that since Jan. 17, 2018 is within a week from the time of voice recognition, i.e. the current point of time, the "Epidemic Period Correction Value" is set to "×1".

Further, in the example shown in the first row, the person word "the client I met" indicates that the utterer "Taro", who met the "client", has possibly had close contact. Therefore, the "Possibility of Infection" is set to "5".

Further, in the example shown in the first row, since the utterer is "Taro", "1", which is the identifier of "Taro", is stored in the "Subject No".

Note here that the data analyzer 201 needs only read out, from the memory 202, word lists in which candidate words are stored in advance for the date and time word, the place word, the person word, and the disease name word, respectively, and, with reference to these word lists, identify the date and time word, the place word, the person word, and the disease name word from the voice recognition content.

Referring to FIG. 5, in the example shown in the sixth row, since a sneezing sound has been recognized from a voice signal obtained by the microphone 206 collecting sounds, the sneezing sound is stored as a voice recognition content. Further, since this sneezing sound is a sound produced by "Taro", "No. 1", which is the identifier of Taro, and "Sound Production" are stored in the "Source" Column. Further, since the sneezing sound has been produced in the house in which the smart speaker 2 is installed, the "House" is stored in the "Place" Column, and since the "House" belongs to the "CC District", the "CC District" is stored in the "District" Column. Further, since the sneezing sound is an early symptom of the infectious disease, "2" is stored in the "Infection alert level" Column, and since the sneezing sound is produced in the case of cold, "Cold" is stored in the "Estimated Name of Infectious Disease" Column. Further, since the sneezing sound is a sound currently produced, the "Epidemic Period Correction Value" is set to "×1". Further, the person who has produced the sneezing sound is "Taro", "1", which is the identifier of "Taro", is stored in the "Subject No." Column. Further, since it is "Taro" himself who has produced the sneezing sound and Taro is infected with cold, "6" is stored in the "Possibility of Infection" Column. Further, since "Taro" possesses a mobile terminal 3 and movement information can be acquired, movement information on Taro is stored in the "Ancillary Data" Column.

It should be noted that every time the smart speaker 2 adds new regional infection information to the regional infection information DB 9, the smart speaker 2 transmits to the server 1 the regional infection information thus added. The regional infection information to be transmitted is obtained by further adding, to the regional infection information generated, the age group and sex of a constituent member indicated by the "Subject No.". Although the regional infection information contains the identifier of the constituent member in the "Subject No."; the server 1, which does not include the registration information DB 10, cannot identify personal information, such as the name of the constituent member, from the "Subject No.". This prevents leakage of the personal information. Further, the age group and the sex are added to the regional infection information for the purpose of classifying the regional infection information by age group and sex in order to assemble a third table T53 of FIG. 7.

Figure 7:
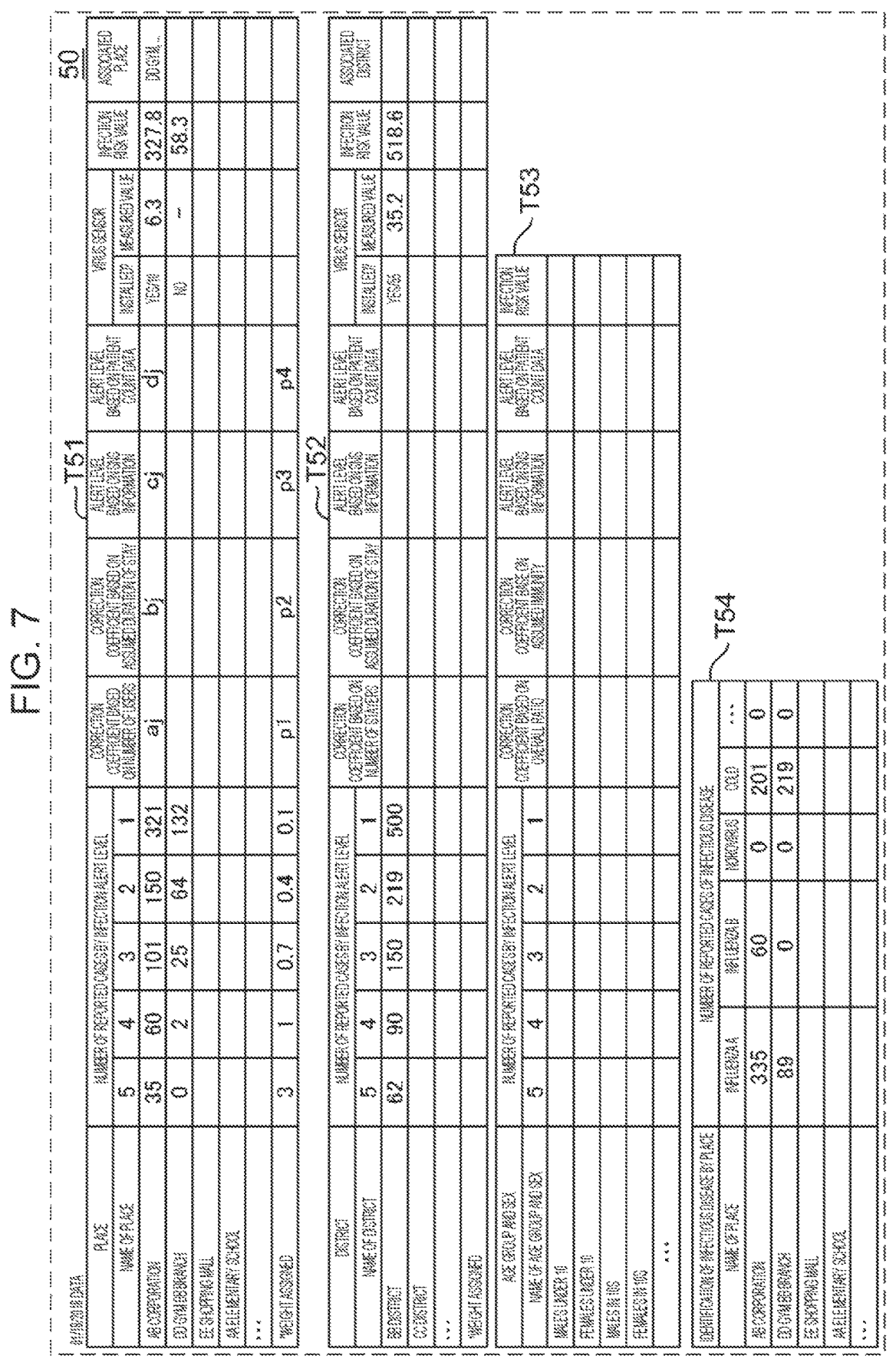

FIG. 7 is a diagram showing an example of a data configuration of the regional infection information tabulation DB 50 stored in the memory 103 of the server 1. The regional infection information tabulation DB 50 is a database that is assembled by tabulating regional infection information transmitted from the smart speakers 2_1 and 2_2, and includes a first table T51, a second table T52, the third table T53, and a fourth table T54.

Figure 9:
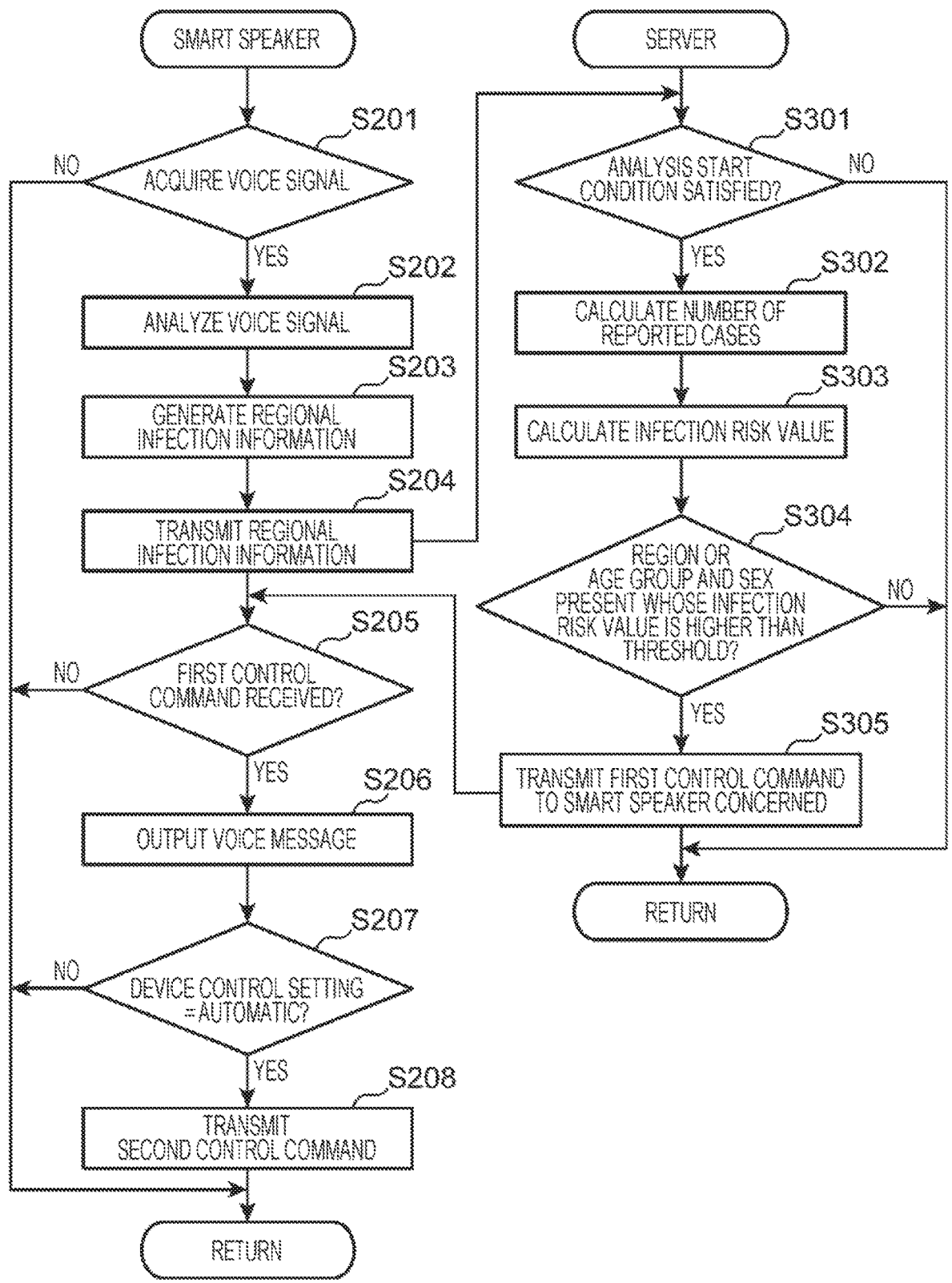
FIG. 9 is a flow chart showing details of steps of the process in FIG. 8 that are performed by the smart speaker and the server.

It should be noted that the first to forth tables T51 to T54 are each created every time a tabulation process is performed upon satisfaction of an analysis condition shown in FIG. 9. FIG. 7 shows tables created by a tabulation process executed on Jan. 18, 2018.

The first table T51 is a table that is assembled by classifying, for each place, the regional infection information transmitted from the smart speakers 2, and assigns one record to each place.

The first table T51 stores "Place", "Number of Reported Cases by Infection Alert Level", "Correction Coefficient Based on Number of Users" (which is an example of the first correction coefficient), "Correction Coefficient Based on Assumed Duration of Stay" (which is an example of the first correction coefficient), "Alert Level Based on SNS Information" (which is an example of the second correction coefficient), "Alert Level Based on Patient Count Data" (which is an example of the third correction coefficient), "Virus Sensor", "Infection Alert Risk Value", and "Associated Place" in association with one another.

The "Place" Column stores the names of places contained in the regional infection information. The "Number of Reported Cases by Infection Alert Level" represents values obtained by tabulating the numbers of reported cases of regional infection information for each of the infection alert levels contained in the regional infection information. For example, in the example shown in the first row, 35 pieces of regional infection information with an infection alert level of 5 are transmitted regarding the "AB Corporation". Therefore, the number of reported cases stored in the infected alert level "5" column for the "AB Corporation" is "35". Similarly, the numbers of reported cases stored in the infected alert level "4", "3", "2" and "1" columns for the "AB Corporation" are "60", "101", "150", and "321" respectively.

Further, the infection alert levels are assigned weights, respectively. The weights are data learned by the infection risk value calculator 112 comparing infection alert levels set by the smart speakers 2 with an actual result of an epidemic of an infectious disease. Note here that the actual result of the epidemic of the infectious disease needs only refer to the infectious disease transition data stored in the infectious disease transition DB 8.

For example, in a case where the infection alert level "5" thus set is an overestimation of the actual result of the epidemic of the infectious disease, the weight takes on a value of lower than "5".

In particular, a difference is calculated by subtracting the number of patients during an epidemic period as indicated by the infectious disease transition data from the number of reported cases of the infection alert level "5" thus calculated, and if the difference is equal to or larger than a predetermined value, the infection alert level "5" is determined to be an overestimation, so that the current weighting value of the infection alert level "5" is reduced by a predetermined span of adjustable range. On the other hand, if the difference is smaller than the predetermined value, the infection alert level "5" is determined not to be an overestimation, so that the current weighting value is maintained.

Further, if the difference is equal to or larger than the predetermined value in a negative direction, the infection alert level "5" is determined not to be an overestimation, so that the current weighting value of the infection alert level "5" is reduced by a predetermined span of adjustable range with the maximum value set to "5". On the other hand, if the difference is smaller than the predetermined value in a negative direction, the infection alert level "5" is determined not to be an overestimation, so that the current weighting value is maintained. In this way, the weighting value is updated every time a tabulation process is performed. It should be noted that the weighting values of the other infection alert levels are updated in a similar manner.

In the example shown in FIG. 7, the infection alert level "5" is assigned a weight of "3". Along the same lines of thought, the infection alert levels "4", "3", "2", and "1" are assigned weights of "1", "0.7", "0.4", and "0.1", respectively. It should be noted that the weights are periodically calculated for updating.

The "Correction Coefficient Based on Number of Users" is set by the infection risk value calculator 112, and is set to a larger value as the number of users in the place concerned becomes larger. Note here that the number of users in the place concerned is identified with reference to the current situations of congestion in large facilities as stored in the regional information DB 7.

The "Correction Coefficient Based on Assumed Duration of Stay" is set by the infection risk value calculator 112, and is set to a larger value as the assumed duration of stay for which the users stay in the place concerned becomes longer. Note here that the "Correction Coefficient Based on Assumed Duration of Stay" takes on a value determined in advance for each place.

The "Alert Level Based on SNS Information" is set by the infection risk value calculator 112, and is set to a larger value as the current frequency of use of a regional infection word indicating the place concerted becomes higher on SNSs. Note here that the frequency of use of the regional infection word is acquired from the SNS word DB 6. The "Alert Level Based on Patient Count Data" is set to a larger value as the number of patients in a region including the place increases.

The "Alert Level Based on Patient Count Data" is set by the infection risk value calculator 112, and is set to a larger value as the number of pieces of patient count data in the place concerted becomes larger. Note here that the patient count data in the place concerned is acquired from the patient count DB 5.

The "Virus Sensor" represents the presence or absence of the installation of virus sensors 4 in the place concerned and the number of virus sensors 4 installed in the place concerned. The "Infection Risk Value" is calculated by the infection risk value calculator 112, and indicates a degree of epidemicity of the infectious disease in the place concerned.

The Infection Risk Value" is such that the infection risk value calculator 112 calculates the infection risk value of a place j according to Formula (1):

$$\text{Infection Risk Value in Place } j = aj \times bj \times cj \times dj \times \Sigma i\alpha i \times \beta ij \qquad (1)$$

where $\alpha i$ is the weight an infection alert level i (=1 to 5) is assigned, $\beta ij$ is the number of reported cases of the infection alert level i in the place j, aj is a correction coefficient based on the number of users in the place j, bj is a correction coefficient based on the assumed duration of stay in the place j, cj is an alert level based on SNS information in the place j, and dj is an alert level based on patient count data in the place j.

For example, in the example of the AB Corporation, the infection risk value is calculated according to $$aj \times bj \times cj \times dj \times (35 \times 3 + 60 \times 1 + 101 \times 0.7 + 150 \times 0.4 + 321 \times 0.1).$$

It should be noted that the "Correction Coefficient Based on Number of Users", the "Correction Coefficient Based on Assumed Duration of Stay", the "Alert Level Based on SNS Information", and the "Alert Level Based on Patient Count Data" may be assigned weights, respectively.

The weight assigned to the "Correction Coefficient Based on Number of Users" is set by the infection risk value calculator 112, and is data learned by comparing the actual result of the epidemic of the infectious disease with the number of users. This weight is set to a smaller value as the rate of influence that the number of users exerts on the actual result of the epidemic of the infectious disease becomes lower.

The weight assigned to the "Correction Coefficient Based on Assumed Duration of Stay" is set by the infection risk value calculator 112, and is set to a smaller value as the rate of influence that the assumed duration of stay exerts on the actual result of the epidemic of the infectious disease becomes lower. The weight assigned to the "Alert Level Based on SNS Information" is set by the infection risk value calculator 112, and is set to a smaller value as the rate of influence that SNS information exerts on the actual result of the epidemic of the infectious disease becomes lower. The weight assigned to the "Alert Level Based on Patient Count Data" is set by the infection risk value calculator 112, and is set to a smaller value as the rate of influence that the number of patients exerts on the actual result of the epidemic of the infectious disease becomes lower.

The infection risk value calculator 112 calculates an infection risk value according to Formula (2):

$$\text{Infection Risk Value in Place } j = p1 \times aj \times p2 \times bj \times p3 \times cj \times p4 \times dj \times \Sigma i\alpha i \times \beta ij \qquad (2)$$

where p1, p2, p3, and p4 are the weights assigned to the "Correction Coefficient Based on Number of Users", the "Correction Coefficient Based on Assumed Duration of Stay", the "Alert Level Based on SNS Information", and the "Alert Level Based on Patient Count Data", respectively.

Further, the infection risk value may be set in consideration of the number of virus sensor 4 installed and values measured by the virus sensors 4. In this case, the infection risk value calculator 112 needs only calculate a final infection risk value by making the infection risk value obtained by Formula (1) or (2) smaller as the number of virus sensors 4 installed increases and making the infection risk value obtained by Formula (1) or (2) larger as the values measured by the virus sensors 4 increase.

The "Associated Place" represents a place that is highly likely to be visited by a user who stays in the place concerned. For example, since many of the employees of the "AB Corporation" go to the "DD Gym", the "DD Gym" is stored as a place associated with the "AB Corporation".

In this case, the infection risk value of the place concerned may be set in consideration of the infection risk value of the associated place. For example, the final infection risk value may be calculated by adding, to the infection risk value of the place concerned, a value obtained by multiplying the infection risk value of the associated place by a predetermined coefficient.

The second table T52 is a table assembled by classifying, for each district, the regional infection information transmitted from the smart speakers 2. Since the second table T52 is identical to the first table T51 except that the regional infection information is classified not for each place but for each district, a detailed description of the second table T52 is omitted. Note, however, that the second table T52 includes "Correction Coefficient Based on Number of Stayers" instead of the "Correction Coefficient Based on Number of Users". The "Correction Coefficient Based on Number of Stayers" represents a correction coefficient corresponding to a person who stayed in a district. Further, the second table T52 includes "Associated District" instead of the "Associated Place".

The third table T53 is a table that is assembled by classifying, for each age group and sex, the regional infection information transmitted from the smart speakers 2, and assigns one record to each age group and sex. Each age group and sex category adopted here is one of ten categories of males by age such as "Males under 10" and ten categories of females by age such as "Females under 10".

As is the case with the first table T51, the third table T53 includes "Number of Reported Cases by Infection Alert Level", "Alert Level Based on SNS Information", and "Alert Level Based on Patient Count Data". In addition, the third table T53 includes "Correction Coefficient Based on Overall Ratio" and "Correction Coefficient Based on Immunity" instead of the "Correction Coefficient Based on Number of Users" and the "Correction Coefficient Based on Assumed Duration of Stay". The "Correction Coefficient Based on Overall Ratio" represents the proportion of each age group to the total number of individuals tabulated from the regional infection information transmitted from the smart speakers 2. The "Correction Coefficient Based on Assumed Immunity" is set to a smaller value for an age group with higher immunity.

The fourth table T54 is a table assembled by classifying, for each place and each infectious disease, the regional infection information transmitted from the smart speakers 2, and assigns one record to each place. For example, in the example of the AB Corporation in the first row, the numbers of reported cases by infectious disease according to the regional infection information are stored.

Figure 8:
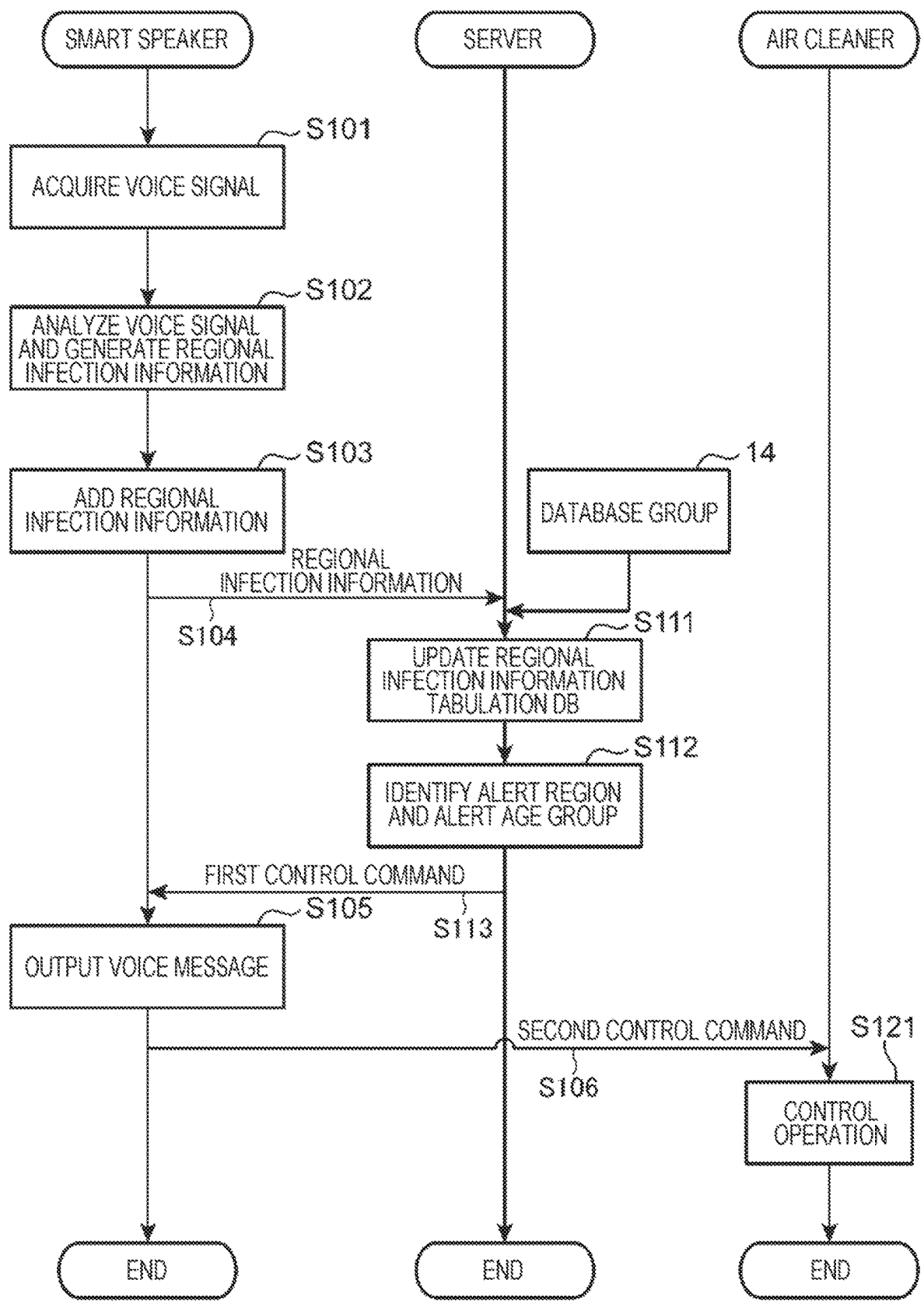
FIG. 8 is a flow chart showing an example of a process that is performed by the information providing system according to Embodiment 1 of the present disclosure.

FIG. 8 is a flowchart showing an example of a process that is performed by the information providing system according to Embodiment 1 of the present disclosure. In step S101, the microphone 206 of a smart speaker 2 acquires a voice signal by collecting ambient sounds. In step S102, the data analyzer 201 of the smart speaker 2 analyzes the voice signal and generates regional infection information. In this example, the voice signal is subjected to a voice recognition process, whereby a voice recognition content such as "I heard that the client I met at work yesterday had the flu" is acquired. Further, in this example, voiceprint data is used, whereby an utterer of this voice recognition content is identified. Further, from this voice recognition content, a disease name word, a place word, a date and time word, and a person word are extracted. Then, from results of the extraction of these words, data is stored in each column shown in the regional infection information DB 9, and new regional infection information is added to the regional infection information DB 9 (S103).

In step S104, the communicator 205 of the smart speaker 2 transmits, to the server 1, regional infection information to which "age group" and "sex" data has been added.

In step S111, the reported case count calculator 111 and infection risk value calculator 112 of the server 1 updates the regional infection information tabulation DB 50 by using the regional infection information transmitted from the smart speaker 2 and using the database group 14 when needed.

In step S112, the output information generator 113 of the server 1 identifies an alert region and an alert age group with reference to the regional infection information tabulation DB 50 thus updated.

In step S113, the output information generator 113 of the server 1 generates, through the alert region and alert age group thus identified, a first control command that causes a smart speaker 2 installed in the alert region to output a voice message serving as a notification of a risk of infection, and transmits the first control command to the smart speaker 2 concerned through the communicator 102.

In step S105, the smart speaker 2 that has received the first control command outputs the voice message through the speaker 203 in accordance with the first control command.

In step S106, the smart speaker 2 that has received the first control command transmits a second control command to a corresponding air cleaner 13.

In step S121, the air cleaner 13, which has received the second control command, starts to operate in accordance with the second control command and purifies ambient air.

FIG. 9 is a flowchart showing details of steps of the process in FIG. 8 that are performed by the smart speaker 2 and the server 1. Since steps S201 to S204 are identical to steps S101 to S104 of FIG. 8, a description of steps S201 to S204 is omitted.

In step S301, the processor 101 of the server 1 determines whether an analysis start condition is satisfied. Note here that the analysis start condition is a condition for the start of an analysis of the regional infection information tabulation DB 50, and an adopted example thereof is a condition that a certain period of time has elapsed since the previous analysis or a condition that a certain number of pieces of regional infection information have been received since the previous analysis.

In a case where the analysis start condition is satisfied (YES in S301), the process proceeds to step S302. On the other hand, in a case where the analysis start condition is not satisfied (NO in S301), the process returns to step S301.

In step S302, the reported case count calculator 111 calculates the number of reported cases using regional infection information newly received during a period from the previous analysis to the current analysis.

At this point, by classifying, for each place and for each infection alert level, the regional infection information newly received, the reported case count calculator 111 calculates the numbers of reported cases by infection alert level in each place to generate the first table T51.

Referring to FIG. 7, for example, the regional infection information newly received includes 35 pieces of regional infection information with an infection level "5" regarding the "AB Corporation". Therefore, the first table T51 has "35" stored therein as the number of reported cases with an infection alert level of "5" regarding the AB Corporation.

Similarly, by classifying, for each district and for each infection alert level, the regional infection information newly received, the reported case count calculator 111 calculates the numbers of reported cases by infection alert level in each district to generate the second table T52.

Furthermore, by classifying, for each age group and sex and for each infection alert level, the regional infection information newly received, the reported case count calculator 111 calculates the numbers of reported cases by infection alert level for each age group and sex to generate the third table T53.

Furthermore, by classifying, for each place and for each "estimated infectious disease", the regional infection information newly received, the reported case count calculator 111 calculates the numbers of reported cases of infectious diseases for each place to generate the fourth table T54.

In step S303, the infection risk value calculator 112 calculates an infection risk value for each of the first, second, and third tables T51, T52, and T53 thus generated. At this point, the infection risk value calculator 112 calculates, according to the aforementioned Formula (1) or (2), an infection risk value for each place shown in the first table T51, an infection risk value for each district shown in the second table T52, and an infection risk value for each age group and sex shown in the third table T53.

In step S304, the output information generator 113 determines whether there is a region or an age group and sex whose infection risk value is higher than a threshold. Referring to the first table T51 of FIG. 7, assuming that a threshold of place is for example "300", the AB Corporation is determined to be an alert place, as the infection risk value of the "AB Corporation" is "327.8", which is larger than the threshold.

Further, referring to the second table T52 of FIG. 7, assuming that a threshold of district is for example "400", the "BB District" is determined to be an alert district, as the infection risk value of the "BB District" is "518.6".

Further, referring to the third table T53 of FIG. 7, assuming that a threshold of age group and sex is "400" and the infection risk value of the males in their 10s is 500, the males in their 10s are identified as an alert age group.

If, in step S304, there is no region whose infection risk value is higher than the threshold (NO in S304), the process returns to step S301. On the other hand, if, in step S304, there is a region whose infection risk value is higher than the threshold (YES in S304), the process proceeds to step S305.

In step S305, the output information generator 113 generates a first control command for a smart speaker 2 installed in the alert district and the alert place. At this point, the output information generator 113 needs only generate a first control command that causes the smart speaker 2 to output a voice message "There is an epidemic of influenza in the AA District". Alternatively, the output information generator 113 may generate a first control command that causes the smart speaker 2 to output a voice message "There is an epidemic of influenza in the AA District. In particular, there is an epidemic among males in their 10s". Alternatively, the output information generator 113 may rank a level of infection risk on an approximately three-grade scale of "High", "Medium", and "Low" according to the magnitude of an infection risk value and generate a first control command that causes the smart speaker 2 to output a voice message corresponding to the level. For example, with a high level of infection risk, it is only necessary to generate a first control command that causes the smart speaker 2 to output a voice message "Avoid going out". With a medium level of infection risk, it is only necessary to generate a first control command that causes the smart speaker 2 to output a voice message "Wear a mask when you go out, and gargle and wash your hands when you're home". With a low level of infection risk, it is only necessary to generate a first control command that causes the smart speaker 2 to output a voice message "Wash your hands".

In a case where the communicator 205 of the smart speaker 2 has received a first control command in step S205 (YES in S205), the process proceeds to step S206. On the other hand, in a case where the communicator 205 of the smart speaker 2 has received no first control command in step S205 (NO in S205), the process returns to step S201.

In step S206, the controller 204 of the smart speaker 2 outputs a voice message through the speaker 203 in accordance with the first control command thus received. In this example, as mentioned above, a voice message that notifies the user of an epidemic of an infectious disease, a voice message that notifies the user of an age group and sex among which there is an epidemic, or a voice message that notifies the user of a level of infection risk is outputted.

In step S207, the controller 204 of the smart speaker 2 determines whether the device control setting is "Automatic". If the device control setting is "Automatic" (YES in S207), the controller 204 of the smart speaker 2 transmits a second control command to a corresponding air cleaner 13 through the communicator 205 (S208). On the other hand, if the device control setting is not "Automatic" (NO in S207), the process returns to step S201.

Figure 10:
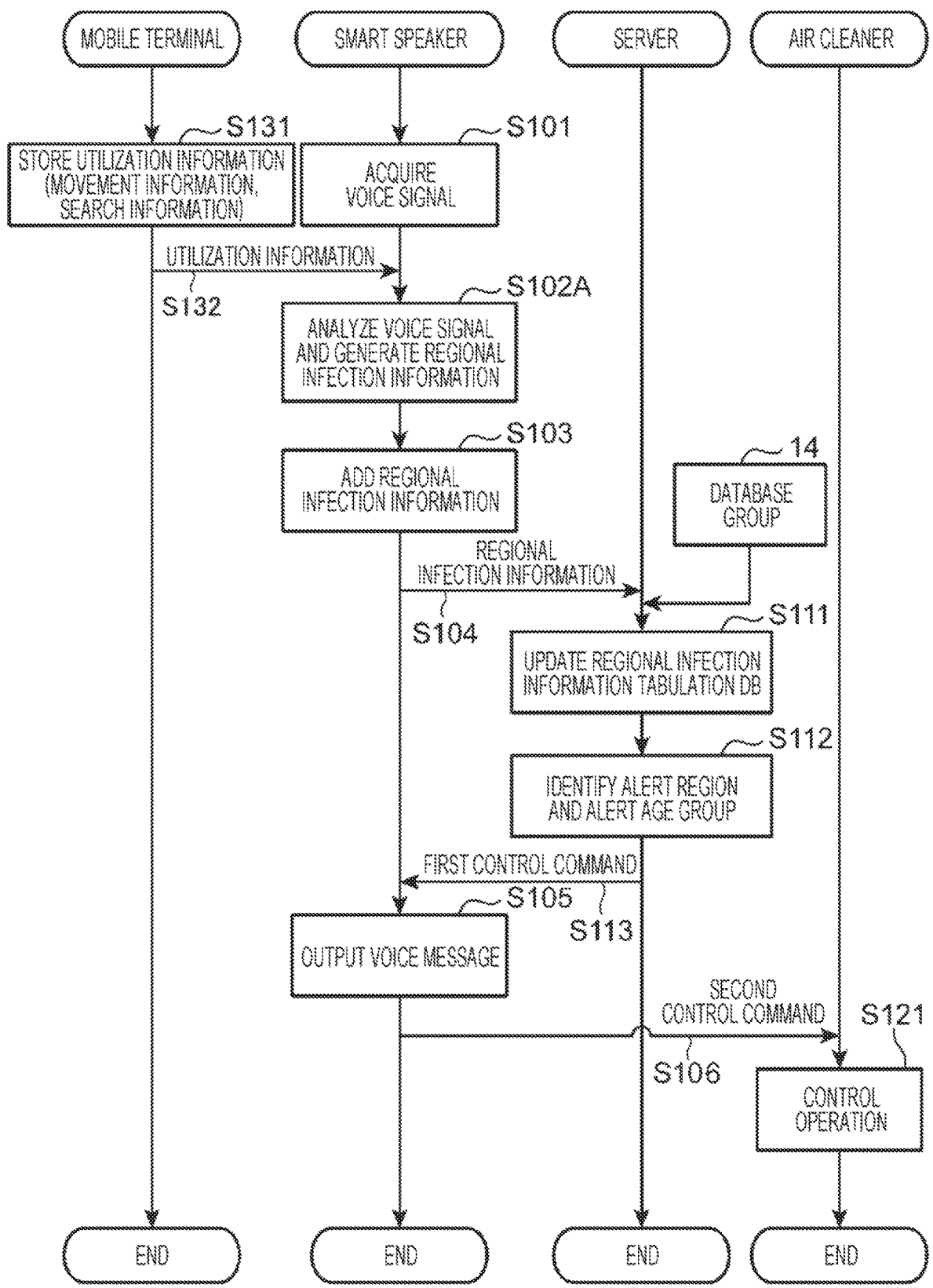
FIG. 10 is a flow chart according to a modification of FIG. 8.

FIG. 10 is a flow chart according to a modification of FIG. 8. The flow chart of FIG. 10 further includes, in addition to the flow chart of FIG. 8, a process that is performed by a mobile terminal 3. Steps of FIG. 10 that are identical to those of FIG. 8 are assigned the same step numbers, and a description of the steps is omitted.

In step S131, the controller 303 of the mobile terminal 3 stores utilization information in the memory 302. Note here that the utilization information contains movement information and search information, and the controller 303 needs only store movement information in the movement information DB 11 at fixed time intervals and, every time a message and/or a search word is entered by the user, store input information and search information in the search information DB 12.

In step S132, the communicator 304 of the mobile terminal 3 transmits the utilization information to the smart speaker 2. At this point, the controller 303 of the mobile terminal 3 needs only incorporate, into the utilization information, those ones of the pieces of movement information in the movement information DB 11 which were stored during a certain period of time from the present to the past and incorporate, into the utilization information, those ones of the pieces of search information in the search information DB 12 which were stored during a certain period of time from the present to the past.

The mobile terminal 3 may periodically transmit the utilization information to the smart speaker 2 or may transmit the utilization information to the smart speaker 2 upon a request from the smart speaker 2.

In step S102A, which follows step S101, the data analyzer 201 of the smart speaker 2 generates regional infection information by using the utilization information when needed in addition to analyzing the voice signal. For example, suppose that a time word was able to be identified from the voice recognition content but a place word was unable to be identified from the voice recognition content. In this case, with movement information on the utterer, the data analyzer 201 needs only use the movement information to identify the place where the utterer was at the date and time indicated by the time word.

Thus, according to the flow chart of FIG. 10, if the voice recognition content is insufficient in information in generating regional infection information, the insufficient information is supplemented by the utilization information from the mobile terminal 3, so that as many situations as possible where no regional infection information is generated can be avoided.

Figure 11:
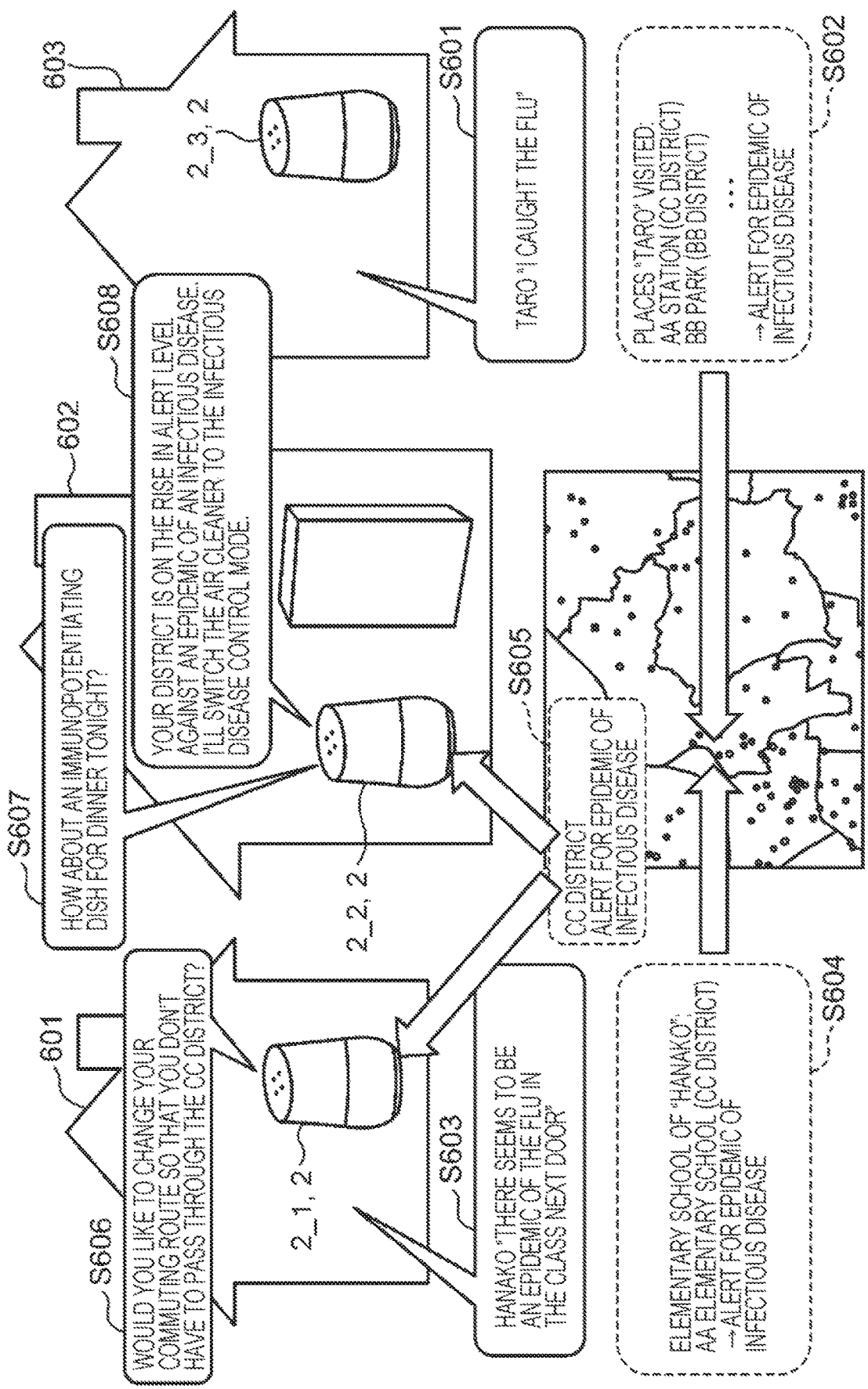
FIG. 11 is a diagram showing a use case of an information providing system of the present disclosure.

FIG. 11 is a diagram showing a use case of an information providing system of the present disclosure. In a house 603, Taro is uttering "I caught the flu" (S601), and this utterance is being phonetically recognized by a smart speaker 2_3. The smart speaker 2_3 determines, from the utterance of S601, that Taro is infected with influenza, and identifies the "AA station" and the "BB Park", to which Taro visited, as alert places from the movement information on Taro (S602). Then, the smart speaker 2_3 notifies the server 1 of the alert places thus identified.

In a house 601, Hanako is uttering "There seems to be an epidemic of the flu in the class next door" (S603), and this utterance is being phonetically recognized by the smart speaker 2_1. The smart speaker 2_1 identifies the AA Elementary School, which is Hanako's elementary school, as an alert place from the utterance of S603 (S604). Then, the smart speaker 2_1 transmits regional infection information to the server 1 to notify the server 1 of the alert place thus identified.

By analyzing these pieces of regional infection information, the server 1 determines that the infectious disease is currently epidemic in the CC District, to which the AA Elementary School belongs, and notifies the smart speakers 2_1 and 2_2, which are installed in the CC District, accordingly (S605).

Upon receiving this notification, the smart speaker 2_1 outputs a voice message "Would you like to change your commuting route so that you don't have to pass through the CC District7" (S606). Further, upon receiving this notification, the smart speaker 22 outputs a voice message "How about an immunopotentiating dish for dinner tonight?" (S607) or outputs a voice message "Your district is on the rise in alert level against an epidemic of an infectious disease. I'll switch the air cleaner to the infectious disease control mode" (S608).

In this way, the information providing system of the present disclosure is configured such that from one or more smart speakers 2 connected via the network NT, regional infection information containing an infection alert level obtained by a smart speaker 2 analyzing a voice signal and a region associated with the infection alert level is acquired. Moreover, an infection risk value of each region is calculated by calculating the number of reported cases of the infectious disease for each infection alert level in each region from the regional infection information, assigning a weight to the number of reported cases thus calculated according to the infection alert level, and evaluating the number of reported cases assigned the weight. Therefore, the information providing system can accurately and timely identify an infection risk value for each region by collecting a large number of pieces of regional infection information generated on the basis of utterances that are exchanged, for example, in a user's house.

Further, in the information providing system, a first control command that causes a smart speaker 2 in each region to output a voice message according to an infection risk value is generated, and is transmitted to a smart speaker 2 in a corresponding region. This makes it possible to provide the user with appropriate information according to the infection risk value, making it possible to avoid causing the user to take excessive countermeasures against the infectious disease or making the user take insufficient countermeasures against the infectious disease.

It should be noted that the following modifications of Embodiment 1 may be adopted.

(1-1) Although, in Embodiment 1, a second control command is transmitted to the air cleaner 13 from a smart speaker 2 having received a first control command, this is not intended to limit the present disclosure. For example, a second control command may be transmitted to the air cleaner 13 directly from the server 1. In this case, the server 1 needs only store regions in which smart speakers 2 are installed and communication addresses in association with each other.

(1-2) In Embodiment 1, the data analyzer 201 of a smart speaker 2 may calculate, in generating regional infection information, a distance of utterance between a place word and a disease name word as extracted from a voice recognition content and, if the distance of utterance is equal to or greater than a certain value, output through the speaker 203 a question message that asks the user whether a place identified from the place word is correct. Then, in a case where the user has uttered affirmatively, the data analyzer 201 needs only generate regional infection information associating the place identified from the place word with an infection alert level identified from the disease name word and store the regional infection information in the regional infection information DB 9. As the distance of utterance, the number of characters from the disease name word to the place word in text data representing the voice recognition content can be adopted. This is based on the idea that a larger number of characters from the disease name word to the place word leads to a drop in association between the words.

(1-3) In generating regional infection information, the data analyzer 201 of a smart speaker 2 may identify, from movement information on a constituent member (infected person), identified from a voice recognition content, whose infection alert level is equal to or higher than a certain level, facilities such as stations, commercial facilities, and schools located on a route of movement of the constituent member where multitudes of people gather, and may notify the server 1 of the facilities thus identified through the communicator 205. Moreover, the server 1 may raise, by predetermined values, infection risk values of places and districts of the facilities thus notified. This makes it possible to more accurately calculate infection risk values in places and districts where there are facilities located on a route of movement of an infected person.

(1-4) Although, in Embodiment 1, a first control command is transmitted to a smart speaker 2 in a region whose infection risk value is equal to or higher than a threshold, this is not intended to limit the present disclosure and a first control command may be transmitted to all smart speakers 2. In this case, it is only necessary to transmit, to the smart speakers 2, a first control command that causes the smart speakers 2 to output different voice messages depending on infection risk values. For example, as mentioned above, it is only necessary to transmit a first control command that causes the smart speakers 2 to output a voice message determined in advance according to whether an infection risk value is high, medium, or low. Further, to a smart speaker 2 installed in a region whose infection risk value is equal to or lower than the threshold, it is only necessary to transmit a first control command that causes the smart speaker 2 to output a voice message indicating that although the infectious disease is not currently epidemic in this district, the infectious disease is currently epidemic in a different district.

(1-5) Although Embodiment 1 has been described on the assumption that the weights shown in FIG. 7 vary, this is not intended to limit the present disclosure and the weights may take on predetermined fixed values. In this case, for example, the weighting values assigned to the levels "5" to "1" with respect to the numbers of reported cases by infection alert level need only take on "5" to "1".

(1-6) Although, in Embodiment 1, infection risk values are calculated by assigning, to the numbers of reported cases for each infection alert level, weights corresponding to the infection alert levels and evaluating the numbers of reported cases assigned the weights, this is not intended to limit the present disclosure. For example, the infection risk values may be calculated evaluating the numbers of reported cases for each infection alert level without assigning weights.

(1-7) A specific example of the aforementioned multi-devices is as follows. A multi-device includes a processor, a display unit, a memory, and an inputter. The processor executes a word recognition process on an input signal containing a word entered into the inputter. The word encompasses a message and/or a search word. The inputter is an operation device such as a touch panel, a keyboard, or a mouse, a microphone, or the like. The input signal refers to a signal obtained by converting information containing a word entered by the inputter into an electrical signal.

The processor includes an infection alert level identifier, a region identifier, a regional infection information generator, and an output information generator. The infection alert level identifier executes a word recognition process on an input signal acquired by the inputter. The infection alert level identifier extracts, from a result of the word recognition process, first word data containing a word related to a risk of infection and identifies an infection alert level from the first word data. The first word data is for example the disease name word shown in FIG. 6.

The region identifier executes a word recognition process on an input signal during a certain period of time before and after the time that the inputter acquired the input signal corresponding to the first word data. The region identifier extracts second word data from the result of the word recognition process and identifies a region associated with the first word data from the second word data. Alternatively, the region identifier identifies a region associated with the first word data using movement history data representing a history of movements of the multi-device. The second word data is for example the place word, such as "work", shown in FIG. 6.

The regional infection information generator generates regional infection information associating the region thus identified with the infection alert level thus identified, and accumulates the regional infection information in the regional infection information DB 9 (which is equivalent to a memory).

The output information generator generates, from the regional infection information accumulated in the memory, a message corresponding to the infection alert level of the region.

Embodiment 2

Figure 12:
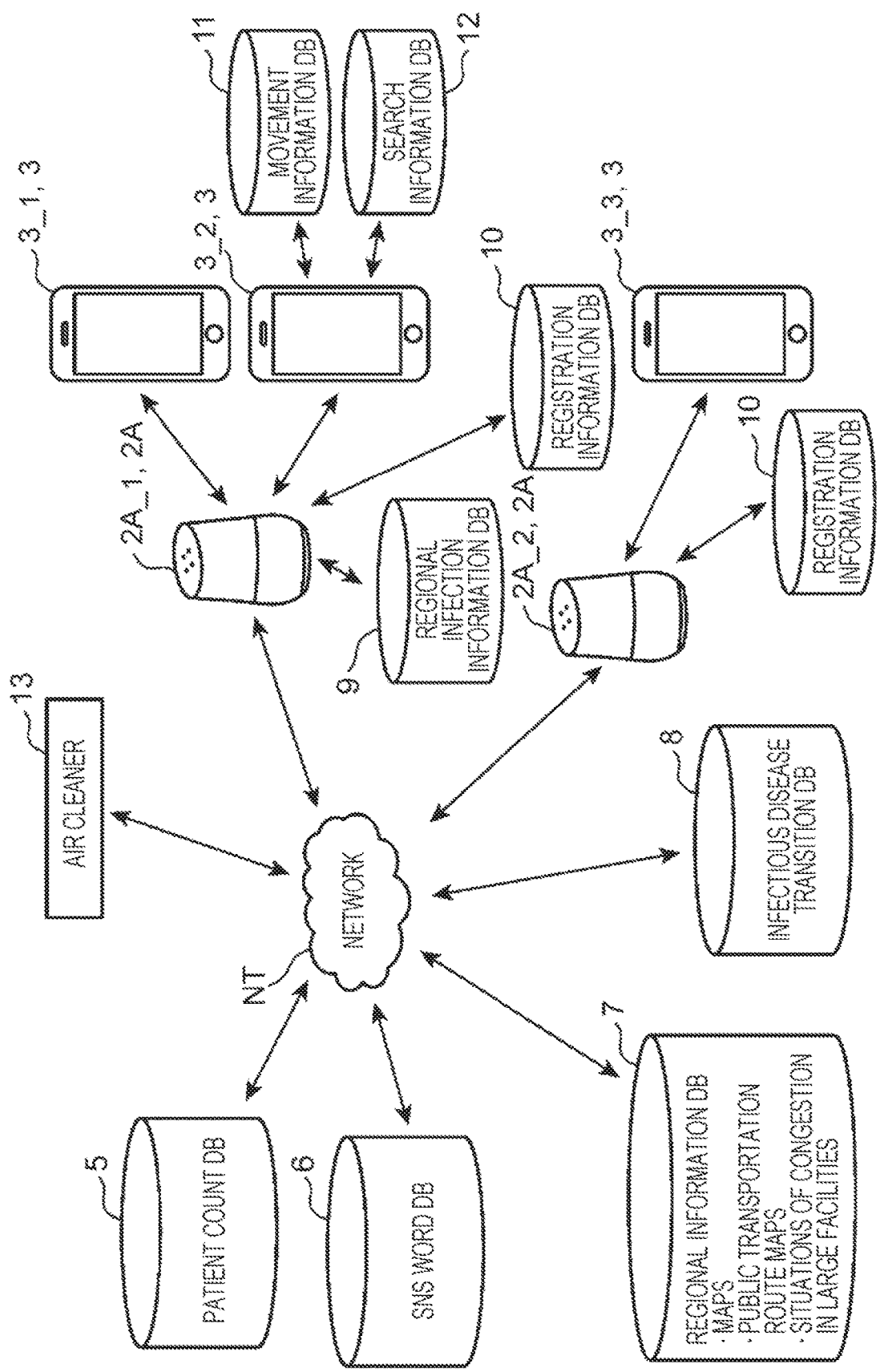
FIG. 12 is a diagram showing an example of a network configuration of an information providing system according to Embodiment 2 of the present disclosure.

FIG. 12 is a diagram showing an example of a network configuration of an information providing system according to Embodiment 2 of the present disclosure. A description of contents of Embodiment 2 that overlap those of Embodiment 1 is omitted. In the information providing system according to Embodiment 2, the server 1 is replaced by a plurality of smart speakers 2A that cooperate with each other to provide users with information related to an infectious disease.

The information providing system according to Embodiment 2 includes smart speakers 2A (each of which is an example of the voice recognition device or the device), mobile terminals 3, a regional infection information DB 9, registration information DBs 10, a movement information DB 11, a search information DB 12, and an air cleaner 13 (which is an example of the device).

These devices are communicably connected to one another via a network NT. The network NT encompasses, for example, an Internet communication network, a mobile phone communication network, and the like.

Figure 13:
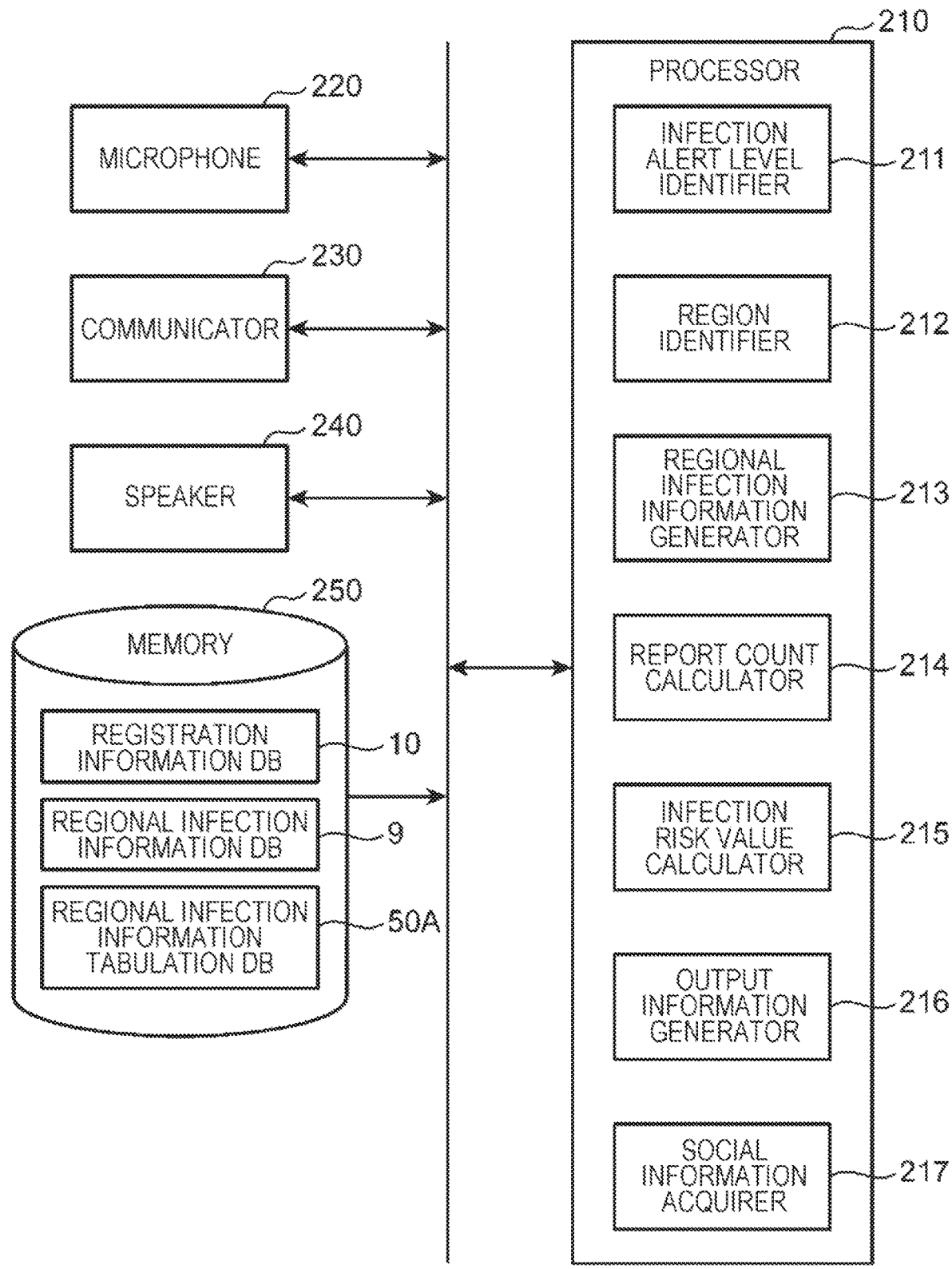
FIG. 13 is a block diagram showing an example configuration of a smart speaker shown in FIG. 12.

FIG. 13 is a block diagram showing an example configuration of each of the smart speakers 2A shown in FIG. 12. The smart speaker 2A includes a processor 210, a microphone 220, a communicator 230, a speaker 240, and a memory 250. The processor 210 performs a voice recognition process on a voice signal obtained by the microphone 220 collecting sounds.

The processor 210 includes an infection alert level identifier 211, a region identifier 212, a regional infection information generator 213, a reported case count calculator 214, an infection risk value calculator 215, an output information generator 216, and a social information acquirer 217.

The infection alert level identifier 211 extracts, from a voice signal obtained by the microphone 220 collecting sounds, first voice data containing at least one selected from the group consisting of a word and a sound related to a risk of infection and identifies an infection alert level from the first voice data. The infection alert level identifier 211 estimates, from an utterance content represented by the first voice data, an infectious disease that is currently epidemic in a region or an infectious disease with which a particular person is infected. The infection alert level identifier 211 estimates, from an utterance content of second voice data, a period of time for which the particular person is infected with the infectious disease, and corrects the infection alert level using an estimation result.

The region identifier 212 extracts second voice data from a voice signal obtained by the microphone 220 collecting sounds during a certain period of time before and after the time that first voice data was obtained by collecting sounds and identifies a region associated with the first voice data from the second voice data. Alternatively, the region identifier 212 identifies a region associated with the first voice data using movement information (which is an example of the movement history data) on an utterer of the first voice data. As a certain period of time before and after the time that the first voice data was obtained by collecting sounds, the duration of a series of conversations that users exchange regarding the infectious disease is adopted, and for example, a value such as ten seconds, thirty seconds, or one minute is adopted.

The regional infection information generator 213 generates regional infection information by associating the region identified by the region identifier 212 with the infection alert level identified by the infection alert level identifier 211, and accumulates the regional infection information in the regional infection information DB 9 of the memory 250. In a case where there is not sufficient information for generating regional infection information, the regional infection information generator 213 causes the speaker 240 to output a question message, acquires a response voice signal to the question message through the microphone 220, and generates regional infection information using the response voice signal.

The reported case count calculator 214 calculates the numbers of reported cases of the infectious disease for each of one or more infection alert levels in each of one or more regions by classifying, for each region and each infection alert level, the regional infection information accumulated in the regional infection information DB 9.

The infection alert level is data that numerically expresses a degree of epidemicity of the infectious disease, and the data is obtained by analyzing a voice signal, contained in the first voice data, that represents a cough or a sneeze or an utterance content represented by the first voice data.

The infection risk value calculator 215 assigns, to the number of reported cases calculated by the reported case count calculator 214, a weight corresponding to the infection alert level and calculates an infection risk value of each region by evaluating the number of reported cases assigned the weight. The term "infection risk value" here refers to an index that indicates the magnitude of a risk of infection with the infectious disease in each region.

The output information generator 216 generates a voice message corresponding to the infection risk value from the risk of infection of each reach as calculated by the infection risk value calculator 215. Note here that the output information generator 216 for example generates a first control command that causes a different smart speaker 2A installed in a region determined to be high in infection risk value to generate and output a voice message, and transmits the first control command to the different smart speaker 2A through the communicator 230.

The output information generator 216 generates a second control command that brings into operation an air cleaner 13 installed in a region determined to be high in infection risk value, and transmits the second control command to the air cleaner 13.

The social information acquirer 217 acquires, from a social network service server through the communicator 230, information containing a regional infection word indicating a regional epidemic of the infectious disease in a region and the frequency of use of the regional infection word. In this case, the infection risk value calculator 215 calculates the infection risk value using a correction coefficient that effects an increase in infection risk value of a corresponding region as the frequency of use of a regional infection word of the corresponding region becomes higher.

The microphone 220 collects ambient sounds and converts them into a voice signal. The communicator 230 is constituted by a communication device through which the smart speaker 2A is connected to the network NT. The speaker 240 outputs a voice message under control of the processor 210.

The memory 250 is constituted, for example, by a semiconductor memory, and stores a registration information DB 10, the regional infection information DB 9, and a regional infection information tabulation DB 50A. The registration information DB 10, the regional infection information DB 9, and the regional infection information tabulation DB 50A will be described in detail later.

Since the data configuration of the registration information DB 10 stored in the memory 250 of the smart speaker 2A is identical to that of FIG. 4, a detailed description of the data configuration is omitted.

Note, however, that in Embodiment 2, the "Announcement Setting" shown in the basic information table T11 represents configuration information indicating whether to, upon receiving a first control command not from the server 1 but from a different smart speaker 2A, cause the smart speaker 2A to output a voice message. For example, upon receiving a first control command from a different smart phone 2A in a case where the announcement setting is ON, the smart speaker 2A outputs a voice message contained in the first control command. On the other hand, when the smart speaker 2A has received a first control command from a different smart speaker 2A in a case where the announcement setting is OFF, the smart speaker 2A does not output a voice message contained in the first control command.

Further, in Embodiment 2, the "Device Control Setting" shown in the basic information table T11 represents configuration information indicating whether to, upon receiving a first control command not from the server 1 but from a different smart speaker 2A, transmit to a corresponding air cleaner 13 a second control command that brings the corresponding air cleaner 13 into operation.

As in the case of Embodiment 1, the "Voiceprint Registration No. (Number)" shown in the registration information table T12 represents an index of voiceprint data of each constituent member. Note, however, that since, in Embodiment 2, the voiceprint data of each constituent member is stored in association with the voiceprint registration No. in advance in the memory 250, the voiceprint data of the constituent member concerned is read out from the memory 250 with the voiceprint registration No. as a key.

Since the data configuration of the regional infection information DB 9 stored in the memory 250 of the smart speaker 2A is identical to that of FIG. 5, a detailed description of the data configuration is omitted.

Since the voice recognition process that is performed by the processor 210 of the smart speaker 2A is described with reference to the same diagram as FIG. 6, with reference to which Embodiment 1 is described, a detailed description of the voice recognition process is omitted. Note, however, that in Embodiment 2, it is not the data analyzer 201 but the infection alert level identifier 211 that phonetically recognizes a voice signal obtained by the microphone 220 collecting sounds.

Further, in Embodiment 2, it is not the data analyzer 201 but the infection alert level identifier 211 that extracts, out of a voice recognition content, first voice data containing a disease name word (i.e. a word related to a risk of infection).

Further, in Embodiment 2, it is not the data analyzer 201 but the region identifier 212 that extracts second voice data from a voice signal obtained by the microphone 220 collecting sounds during a certain period of time before and after the time that first voice data was obtained by collecting sounds.

Further, in Embodiment 2, it is not the data analyzer 201 but the region identifier 212 that identifies a place associated with first voice data from second voice data.

Further, in Embodiment 2, it is not the data analyzer 201 but the region identifier 212 that identifies a date and time word and a person word from second voice data.

Note here that the region identifier 212 needs only read out, from the memory 250, word lists in which candidate words are stored in advance for the date and time word, the place word, the person word, and the disease name word, respectively, and, with reference to these word lists, identify the date and time word, the place word, the person word, and the disease name word from the voice recognition content.

FIG. 14 is a diagram showing an example of a data configuration of the regional infection information tabulation DB 50A stored in the memory 250 of the smart speaker 2A according to Embodiment 2. The regional infection information tabulation DB 50A is a database that is assembled by tabulating regional infection information stored in the regional infection information DB 9, and includes a first table T51A and a second table T52A.

Figure 16:
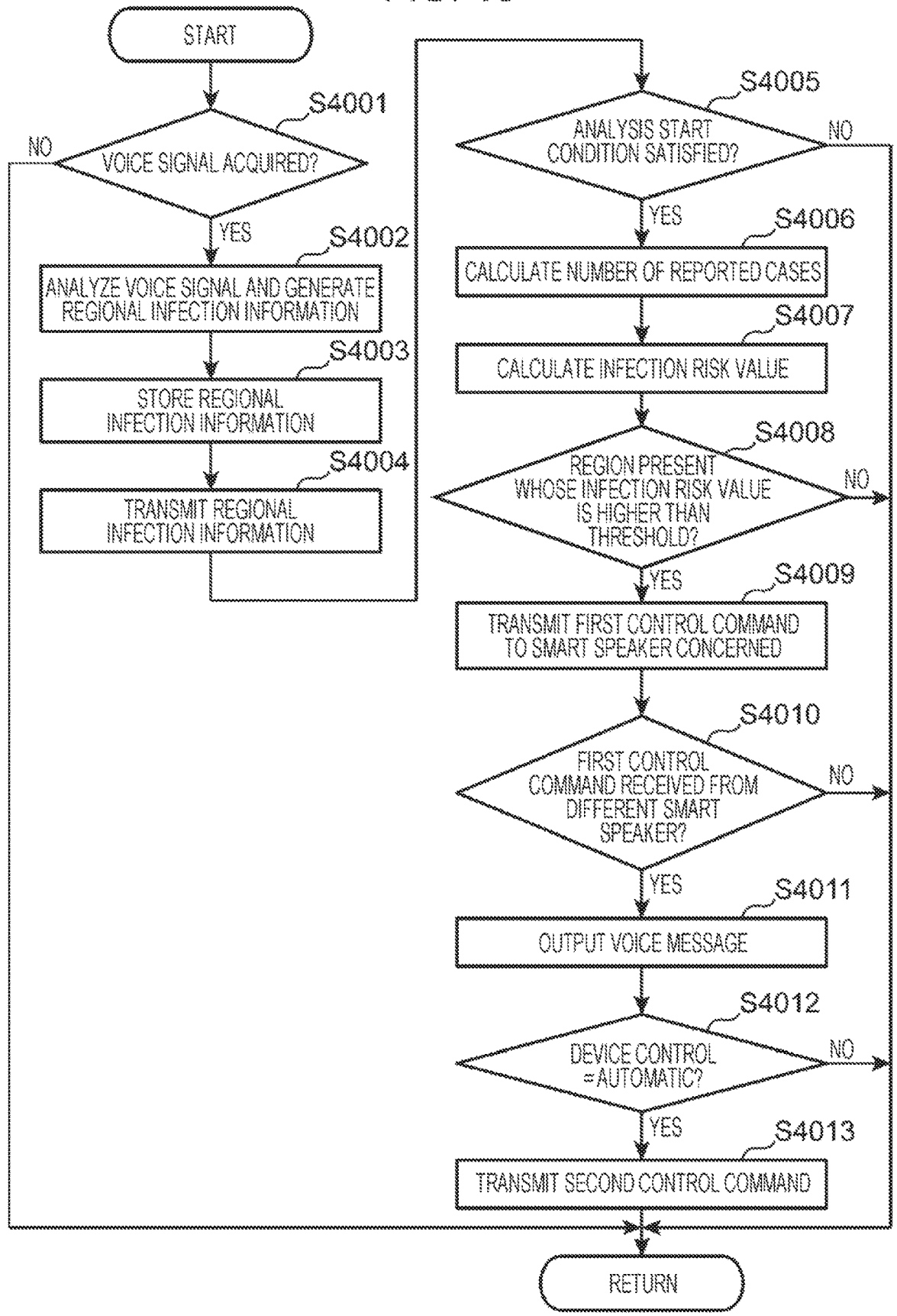
FIG. 16 is a flow chart showing details of steps of the process in FIG. 15 that are performed by a smart speaker.

It should be noted that the first table T51A and the second table T52A are each created every time a tabulation process is performed upon satisfaction of an analysis condition in step S4005 of FIG. 16. FIG. 14 shows tables created by a tabulation process executed on Jan. 18, 2018. Note here that an adoptable example of the analysis start condition is a condition that a certain period of time has elapsed since the previous analysis or a condition that a certain number of pieces of regional infection information have been received since the previous tabulation process.

The first table T51A is a table that is assembled by classifying, for each place, the regional infection information stored in the regional infection information DB 9, and assigns one record to each place.

The first table T51A stores "Place", "Number of Reported Cases by Infection Alert Level", "Correction Coefficient Based on Number of Users", "Correction Coefficient Based on Assumed Duration of Stay", "Alert Level Based on SNS Information" (which is an example of the correction coefficient), "Alert Level Based on Patient Count Data", "Alert Level Based on Cooperative Smart Speaker", "Infection Alert Risk Value", and "Associated Place" in association with one another.

The "Place" Column stores the names of places contained in the regional infection information. The "Number of Reported Cases by Infection Alert Level" represents values obtained by tabulating the numbers of reported cases of regional infection information for each of the infection alert levels contained in the regional infection information. For example, in the example shown in the first row, the newly generated regional infection information includes two pieces of regional infection information with an infection alert level of 5 regarding the "AB Corporation"; therefore, the number of reported cases stored in the infected alert level "5" column for the "AB Corporation" is "2". Similarly, the numbers of reported cases stored in the infected alert level "4", "3", "2" and "1" columns for the "AB Corporation" are "2", "4", "5", and "10", respectively.

Further, the infection alert levels are assigned weights, respectively. The weights are data learned by the infection risk value calculator 215 comparing infection alert levels set by the smart speakers 2A with an actual result of an epidemic of an infectious disease. Note here that the actual result of the epidemic of the infectious disease needs only refer to the infectious disease transition data stored in the infectious disease transition DB 8. Since details of the calculation of these weights are identical to those of Embodiment 1, a detailed description thereof is omitted.

The "Correction Coefficient Based on Number of Users" is set by the infection risk value calculator 215, and is set to a larger value as the number of users in the place concerned becomes larger. Note here that the number of users in the place concerned is identified with reference to the current situations of congestion in large facilities as stored in the regional information DB 7.

The "Correction Coefficient Based on Assumed Duration of Stay" is set by the infection risk value calculator 215, and is set to a larger value as the assumed duration of stay for which the users stay in the place concerned becomes longer. Note here that the "Correction Coefficient Based on Assumed Duration of Stay" takes on a value determined in advance for each place.

The "Alert Level Based on SNS Information" is set by the infection risk value calculator 215, and is set to a larger value as the current frequency of use of a regional infection word indicating the place concerted becomes higher on SNSs. Note here that the frequency of use of the regional infection word is acquired from the SNS word DB 6. The "Alert Level Based on Patient Count Data" is set to a larger value as the number of patients in a region including the place increases.

The "Alert Level Based on Patient Count Data" is set by the infection risk value calculator 215, and is set to a larger value as the number of pieces of patient count data in the place concerted becomes larger. Note here that the patient count data in the place concerned is acquired from the patient count DB 5.

The "Infection Risk Value Based on Cooperative Smart Speaker" represents an infection risk value calculated for each region by a different smart speaker 2A that works together.

The Infection Risk Value" is such that the infection risk value calculator 215 calculates the infection risk value of a place j according to Formula (3):

$$\text{Infection Risk Value in Place } j = aj \times bj \times cj \times dj \times ej \times \Sigma i\alpha i \times \beta ij \quad (3)$$

where αi is the weight an infection alert level i (=1 to 5) is assigned, βij is the number of reported cases of the infection alert level i in the place j, aj is a correction coefficient based on the number of users in the place j, bj is a correction coefficient based on the assumed duration of stay in the place j, cj is an alert level based on SNS information in the place j, dj is an alert level based on patient count data in the place j, and ej is an infection risk value based on a cooperative smart speaker in the place j.

For example, in the example of the AB Corporation, the infection risk value is calculated according to aj×bj×cj×dj× ej×(2×3+2×1+4×0.7+5×0.4+10×0.1).

It should be noted that the "Correction Coefficient Based on Number of Users", the "Correction Coefficient Based on Assumed Duration of Stay", the "Alert Level Based on SNS Information", and the "Alert Level Based on Patient Count Data" may be assigned weights, respectively.

The weight assigned to the "Correction Coefficient Based on Number of Users" is set by the infection risk value calculator 215, and is data learned by comparing the actual result of the epidemic of the infectious disease with the number of users. This weight is set to a smaller value as the rate of influence that the number of users exerts on the actual result of the epidemic of the infectious disease becomes lower.

The weight assigned to the "Correction Coefficient Based on Assumed Duration of Stay" is set by the infection risk value calculator 215, and is set to a smaller value as the rate of influence that the assumed duration of stay exerts on the actual result of the epidemic of the infectious disease becomes lower. The weight assigned to the "Alert Level Based on SNS Information" is set by the infection risk value calculator 215, and is set to a smaller value as the rate of influence that SNS information exerts on the actual result of the epidemic of the infectious disease becomes lower. The weight assigned to the "Alert Level Based on Patient Count Data" is set by the infection risk value calculator 215, and is set to a smaller value as the rate of influence that the number of patients exerts on the actual result of the epidemic of the infectious disease becomes lower. The weight assigned to the "Infection Risk Value Based on Cooperative Smart Speaker" is set by the infection risk value calculator 215, and is set to a smaller value as the rate of influence that the infection risk value based on the cooperative smart speaker exerts on the actual result of the epidemic of the infectious disease becomes lower.

The infection risk value calculator 215 calculates an infection risk value according to Formula (4):

$$\text{Infection Risk Value in Place } j = p1 \times aj \times p2 \times bj \times p3 \times cj \times p4 \times dj \times p5 \times \Sigma i\alpha i \times \beta ij \quad (4)$$

where p1, p2, p3, p4, and p5 are the weights assigned to the "Correction Coefficient Based on Number of Users", the "Correction Coefficient Based on Assumed Duration of Stay", the "Alert Level Based on SNS Information", the "Alert Level Based on Patient Count Data", and the "Infection Risk Value Based on Cooperative Smart Speaker", respectively.

The "Associated Place" represents a place that is highly likely to be visited by a user who stays in the place concerned. For example, since many of the employees of the "AB Corporation" go to the "DD Gym", the "DD Gym" is stored as a place associated with the "AB Corporation".

In this case, the infection risk value of the place concerned may be set in consideration of the infection risk value of the associated place. For example, the final infection risk value may be calculated by adding, to the infection risk value of the place concerned, a value obtained by multiplying the infection risk value of the associated place by a predetermined coefficient.

The second table T52A is a table assembled by classifying, for each district, the regional infection information transmitted from the smart speakers 2A. Since the second table T52A is identical to the first table T51A except that the regional infection information is classified not for each place but for each district, a detailed description of the second table T52A is omitted. Note, however, that the second table T52A includes "Correction Coefficient Based on Number of Stayers" instead of the "Correction Coefficient Based on Number of Users". The "Correction Coefficient Based on Number of Stayers" represents a correction coefficient corresponding to a person who stayed in a district. Further, the second table T52A includes "Associated District" instead of the "Associated Place".

FIG. 15 is a flow chart showing an example of a process that is performed by the information providing system according to Embodiment 2 of the present disclosure. In step S1001, the microphone 220 of a smart speaker 2A_1 acquires a voice signal by collecting ambient sounds. In step S1002, the infection alert level identifier 211 and region identifier 212 of the smart speaker 2A_1 analyze the voice signal, and the regional infection information generator 213 generates regional infection information from a result of the analysis of the voice signal. In this example, the voice signal is subjected to a voice recognition process, whereby a voice recognition content such as "I heard that the client I met at work yesterday had the flu" is acquired. Further, in this example, voiceprint data is used, whereby an utterer of this voice recognition content is identified. Further, from this voice recognition content, a disease name word, a place word, a date and time word, and a person word are extracted.

In step S1003, the processor 210 of the smart speaker 2A_1 stores the newly generated regional infection information in the regional infection information DB 9.

In step S1004, the processor 210 of the smart speaker 2A_1 transmits the newly generated regional infection information to a smart speaker 2A_2 through the communicator 230, receives regional infection information from the smart speaker 2A_2 through the communicator 230, and stores the regional infection information in the regional infection information DB 9. As a result, the memory 250 of a smart speaker 2A accumulates regional infection information generated by a different smart speaker 2A.

In step S1005, the reported case count calculator 214 and infection risk value calculator 215 of the smart speaker 2A_1 updates the regional infection information tabulation DB 50A by tabulating the regional infection information stored in the regional infection information DB 9. As a result, the first table T51A and the second table T52A, which are shown in FIG. 14, are generated.

In step S1006, the output information generator 216 of the smart speaker 2A_1 identifies an alert region with reference to the regional infection information tabulation DB 50A thus updated. Assume here that the alert region thus identified is a region in which the smart speaker 2A_2 is installed.

In step S1007, the output information generator 216 of the smart speaker 2A_1 generates a first control command that causes the smart speaker 2A_1 installed in the alert region thus identified to output a voice message serving as a notification of a risk of infection, and transmits the first control command to the smart speaker 2A_2 through the communicator 230.

In step S1008, the output information generator 216 of the smart speaker 2A_1 generates a voice message that notifies a user of the smart speaker 2A_1 of a risk of infection in the alert region thus identified, and causes the speaker 240 to output the voice message. The outputting of this voice message may be triggered by the utterance against the smart speaker 2A_1 of a voice of such a content that the user will go out to or pass through the alert region thus identified.

It should be noted that since steps S2001 to S2005 that the smart speaker 2A_2 executes are identical to steps S1001 to S1005, a description of steps S2001 to S2005 is omitted.

In step S2006, the smart speaker 2A_2, which has received the first control command, outputs the voice message through the speaker 240 in accordance with the first control command.

In step S2007, the smart speaker 2A_2, which has received the first control command, transmits a second control command to a corresponding air cleaner 13.

In step S3001, the air cleaner 13, which has received the second control command, starts to operate in accordance with the second control command and purifies ambient air.

FIG. 16 is a flow chart showing details of steps of the process in FIG. 15 that are performed by the smart speaker 2A_1. A description is given here by taking, as an example, a use case where the smart speaker 2A_1 receives a first control command from a different smart speaker 2A_3 and transmits a second command to the air cleaner 13.

Since steps S4001 to S4004 are identical to steps S1001 to S1004 of FIG. 15, a description of steps S4001 to S4004 is omitted. In step S4005, the processor 210 of the smart speaker 2A_1 determines whether an analysis start condition is satisfied. Note here that the analysis start condition is a condition for the start of an analysis of the regional infection information tabulation DB 50A, and an adopted example thereof is a condition that a certain period of time has elapsed since the previous analysis or a condition that a certain number of pieces of regional infection information have been received since the previous analysis.

In a case where the analysis start condition is satisfied (YES in S4005), the process proceeds to step S4006. On the other hand, in a case where the analysis start condition is not satisfied (NO in S4005), the process returns to step S4001.

In step S4006, the reported case count calculator 214 calculates the number of reported cases using regional infection information newly received during a period from the previous analysis to the current analysis.

At this point, by classifying, for each place and for each infection alert level, the regional infection information newly received, the reported case count calculator 214 calculates the numbers of reported cases by infection alert level in each place to generate the first table T51A.

Referring to FIG. 14, for example, the regional infection information newly received includes two pieces of regional infection information with an infection level "5" regarding the "AB Corporation". Therefore, the first table T51A has "2" stored therein as the number of reported cases with an infection alert level of "5" regarding the AB Corporation.

Similarly, by classifying, for each district and for each infection alert level, the regional infection information newly received, the reported case count calculator 214 calculates the numbers of reported cases by infection alert level in each district to generate the second table T52A.

In step S4007, the infection risk value calculator 215 calculates an infection risk value for each of the first and second T51A and T52A thus generated. At this point, the infection risk value calculator 215 calculates, according to the aforementioned Formula (3) or (4), an infection risk value for each place shown in the first table T51A and an infection risk value for each district shown in the second table T52A.

In step S4008, the output information generator 216 determines whether there is a region whose infection risk value is higher than a threshold. Referring to the first table T51A of FIG. 14, assuming that a threshold of place is for example "10", the AB Corporation is determined to be an alert place, as the infection risk value of the "AB Corporation" is "13.8", which is larger than the threshold.

Further, referring to the second table T52A of FIG. 14, assuming that a threshold of district is for example "400", the "BB District" is determined to be an alert district, as the infection risk value of the "BB District" is "518.6".

If, in step S4008, there is no region whose infection risk value is higher than the threshold (NO in S4008), the process returns to step S4001. On the other hand, if, in step S4008, there is a region whose infection risk value is higher than the threshold (YES in S4008), the process proceeds to step S4009.

In step S4009, the output information generator 216 generates a first control command for the smart speaker 2A_2 installed in the alert district and the alert place. At this point, the output information generator 216 needs only generate a first control command that causes the smart speaker 2A_2 to output a voice message, for example, to the effect that there is an epidemic of an infectious disease in the district in which the smart speaker 2A_2 is installed. Alternatively, the output information generator 216 may rank a level of infection risk on an approximately three-grade scale of "High", "Medium", and "Low" according to the magnitude of an infection risk value and generate a first control command that causes the smart speaker 2A_2 to output a voice message corresponding to the level. For example, with a high level of infection risk, it is only necessary to generate a first control command that causes the smart speaker 2A_2 to output a voice message "Avoid going out". With a medium level of infection risk, it is only necessary to generate a first control command that causes the smart speaker 2A_2 to output a voice message "Wear a mask when you go out, and gargle and wash your hands when you're home". With a low level of infection risk, it is only necessary to generate a first control command that causes the smart speaker 2A_2 to output a voice message "Wash your hands".

In a case where the communicator 230 of the smart speaker 2A_1 has received a first control command from the difference smart speaker 2A_3 in step S4010 (YES in S4010), the process proceeds to step S4011. On the other hand, in a case where the communicator 230 of the smart speaker 2A_1 has received no first control command in step S4010 (NO in S4010), the process returns to step S4001.

In step S4011, the output information generator 216 of the smart speaker 2A_1 outputs a voice message through the speaker 240 in accordance with the first control command thus received. In this example, as mentioned above, a voice message that notifies the user of an epidemic of an infectious disease or a voice message that notifies the user of a level of infection risk is outputted.

In step S4012, the output information generator 216 of the smart speaker 2A_1 determines whether the device control setting is "Automatic". If the device control setting is "Automatic" (YES in S4012), the output information generator 216 of the smart speaker 2A_1 transmits a second control command to a corresponding air cleaner 13 through the communicator 230 (S4013). On the other hand, if the device control setting is not "Automatic" (NO in S4012), the process returns to step S4001.

Thus, the present embodiment, in which pieces of regional infection information associating infection alert levels with regions are collected on the basis of utterances that are exchanged, for example, in a user's house, makes it possible to accurately and timely generate a voice message suited to an infection alert level for each region and output the voice message through a speaker.

Accordingly, the present configuration makes it possible to provide the user with appropriate information according to the infection alert level, making it possible to avoid causing the user to take excessive countermeasures against the infectious disease or making the user take insufficient countermeasures against the infectious disease.

Embodiment 3

In an information providing system according to Embodiment 3, smart speakers 2B and a server 1A cooperate with each other to provide users with information related to an infectious disease. A description of contents of Embodiment 3 that overlap those of Embodiments 1 and 2 is omitted.

Figure 17:
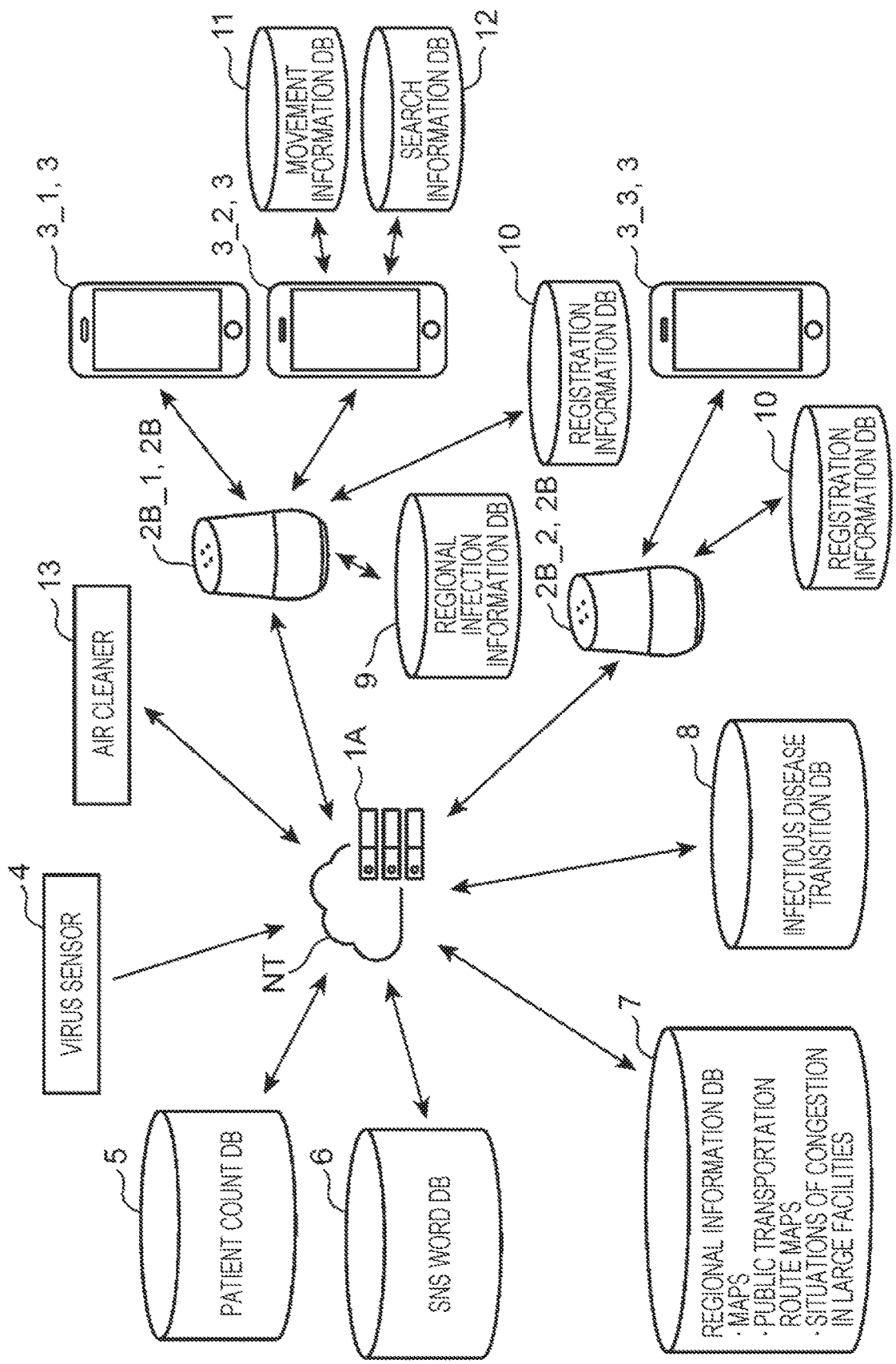
FIG. 17 is a diagram showing an example of a network configuration of an information providing system according to Embodiment 3 of the present disclosure.

FIG. 17 is a diagram showing an example of a network configuration of the information providing system according to Embodiment 3 of the present disclosure.

In FIG. 17, the server 1A and the virus sensor 4 are further provided in addition to the configuration of FIG. 13. The server 1A is for example a cloud server constituted by one or more computers, and calculates an infection risk value of each region using regional infection information acquired from the smart speakers 2B.

Figure 18:
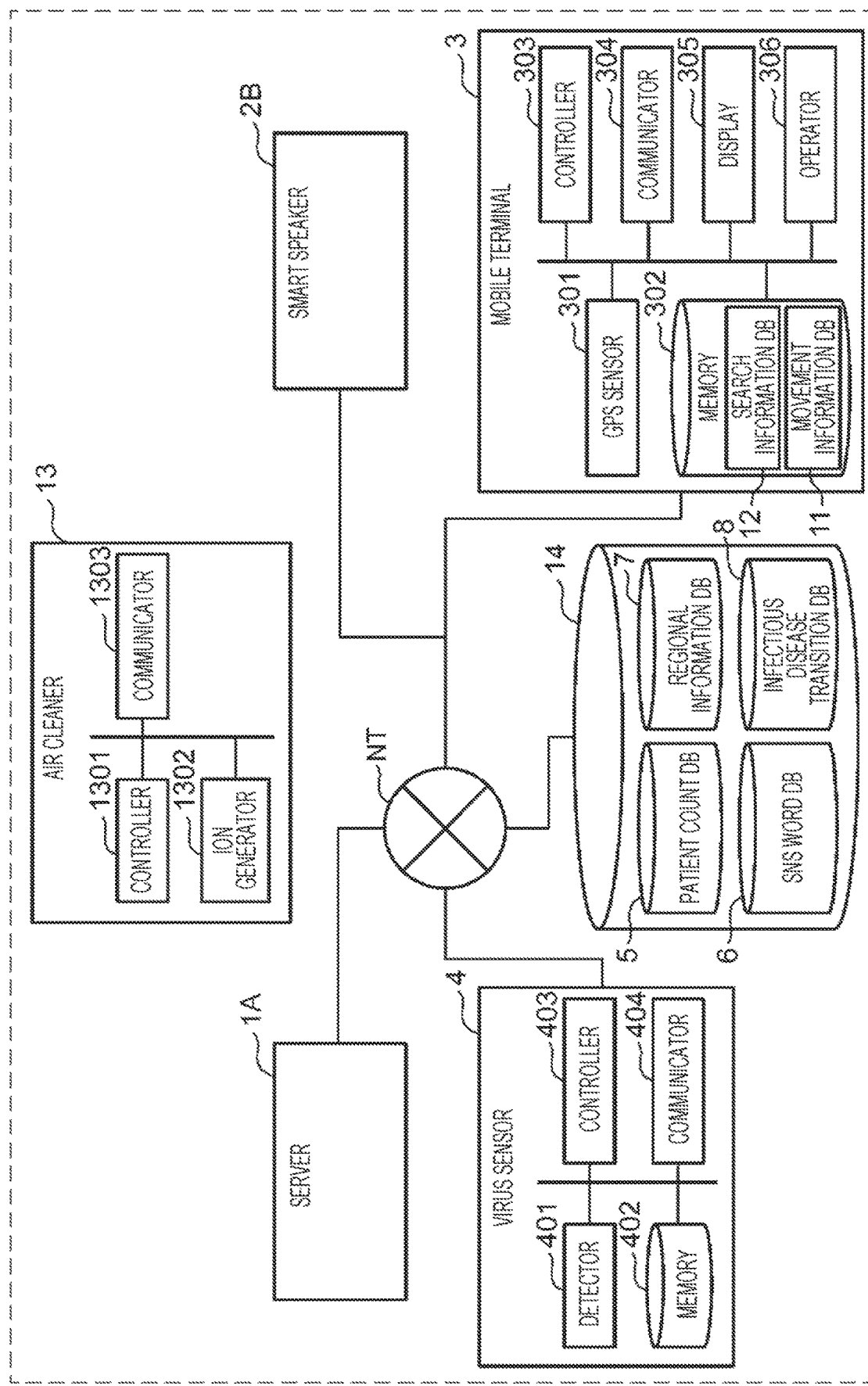
FIG. 18 is a block diagram showing an example configuration of the information providing system shown in FIG. 17.

FIG. 18 is a block diagram showing an example configuration of the information providing system shown in FIG. 17. Since components shown in FIG. 18 other than the server 1A and the smart speakers 2B are identical to those shown in FIG. 2, a description of the components is omitted.

Figure 19:
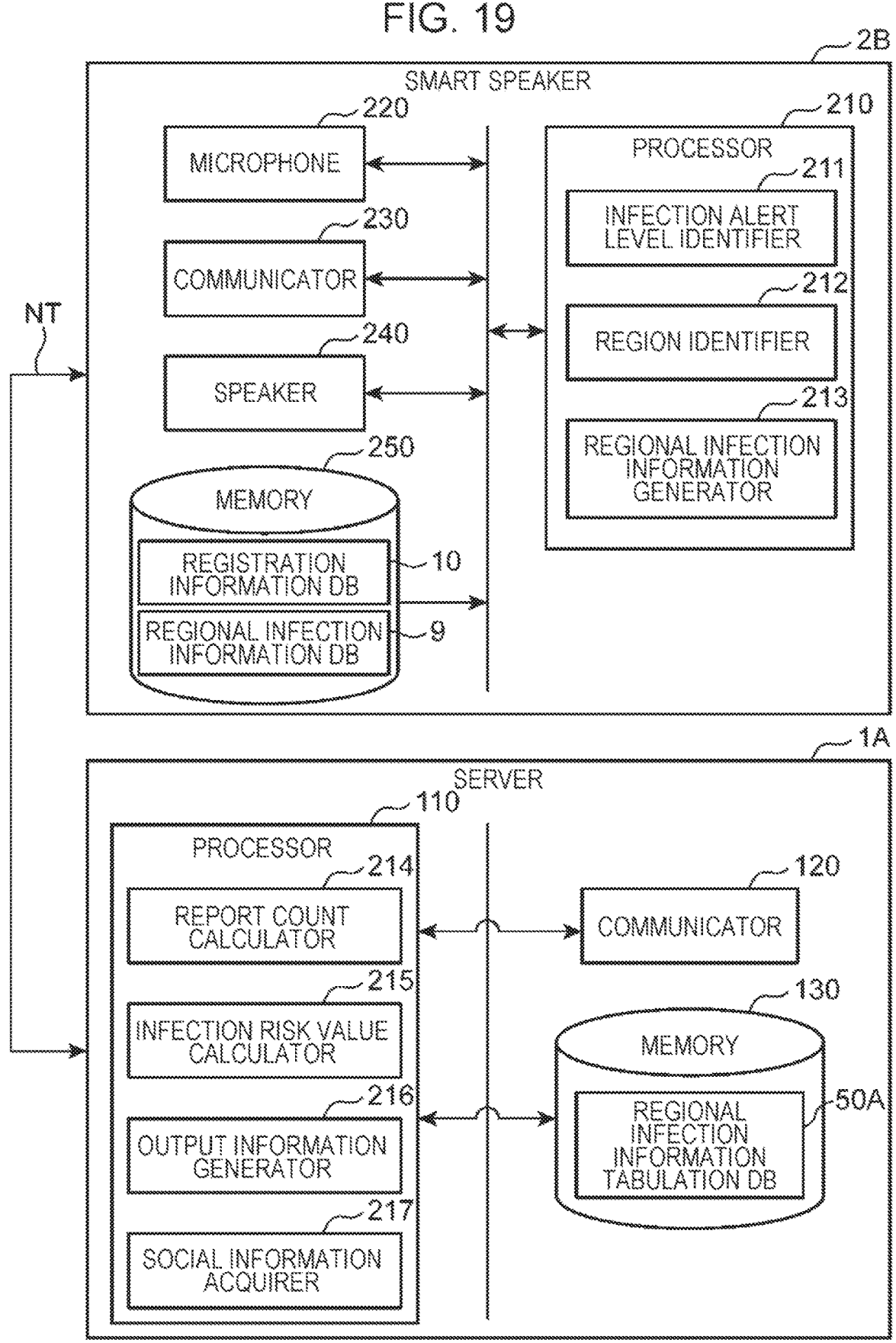
FIG. 19 is a block diagram showing example configurations of a smart speaker shown in FIG. 18 and a server shown in FIG. 18.

FIG. 19 is a block diagram showing example configurations of each of the smart speakers 2B shown in FIG. 18 and the server 1A shown in FIG. 18. FIG. 19 differs from FIG. 13 in that the regional infection information tabulation DB 50A is provided in a memory 130 of the server 1A instead of the memory 250 of the smart speaker 2A and that the reported case count calculator 214, the infection risk value calculator 215, the output information generator 216, and the social information acquirer 217 are provided in a processor 110 of the server 1A instead of the processor 210 of the smart speaker 2A.

Figure 20:
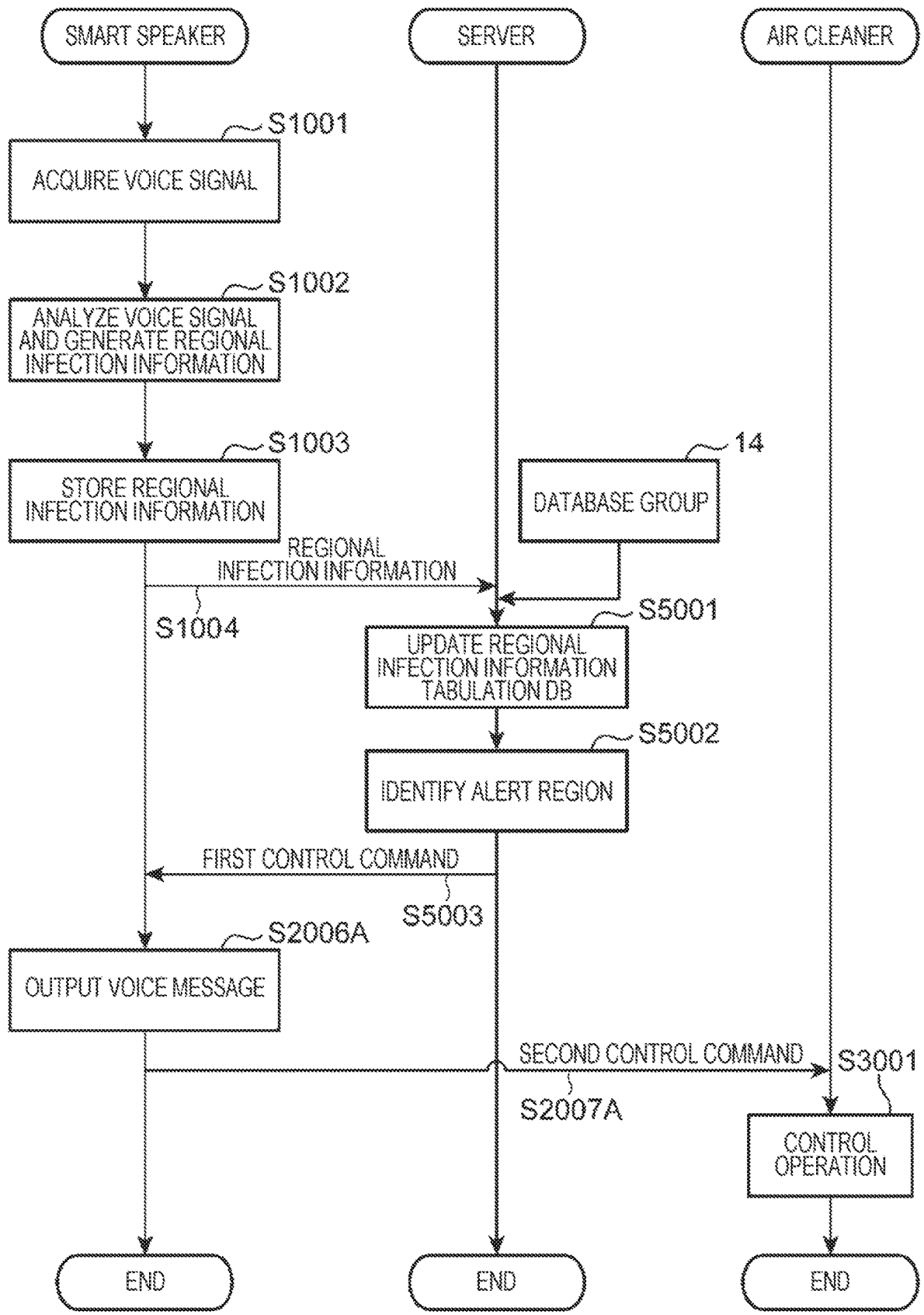
FIG. 20 is a flow chart showing an example of a process that is performed by the information providing system according to Embodiment 3 of the present disclosure.

FIG. 20 is a flow chart showing an example of a process that is performed by the information providing system according to Embodiment 3 of the present disclosure. Steps of FIG. 20 that are identical to those of FIG. 15 are assigned the same step numbers, and a description of the steps is omitted.

In step S5001, which follows step S1004, the reported case count calculator 214 and infection risk value calculator 215 of the server 1A, having received regional infection information from a smart speaker 2B, updates the regional infection information tabulation DB 50A by using the regional infection information transmitted from the smart speaker 2B and using the database group 14 when needed.

In step S5002, the output information generator 216 of the server 1A identifies an alert region with reference to the regional infection information tabulation DB 50A thus updated.

In step S5003, the output information generator 216 of the server 1A generates, through the alert region thus identified, a first control command that causes a smart speaker 2B installed in the alert region to output a voice message serving as a notification of a risk of infection, and transmits the first control command to the smart speaker 2B concerned through the communicator 102.

In step S2006A, the smart speaker 2B that has received the first control command outputs the voice message through the speaker 240 in accordance with the first control command.

In step S2007A, the smart speaker 2B that has received the first control command transmits a second control command to a corresponding air cleaner 13.

In step S3001, the air cleaner 13, which has received the second control command, starts to operate in accordance with the second control command and purifies ambient air.

Figure 21:
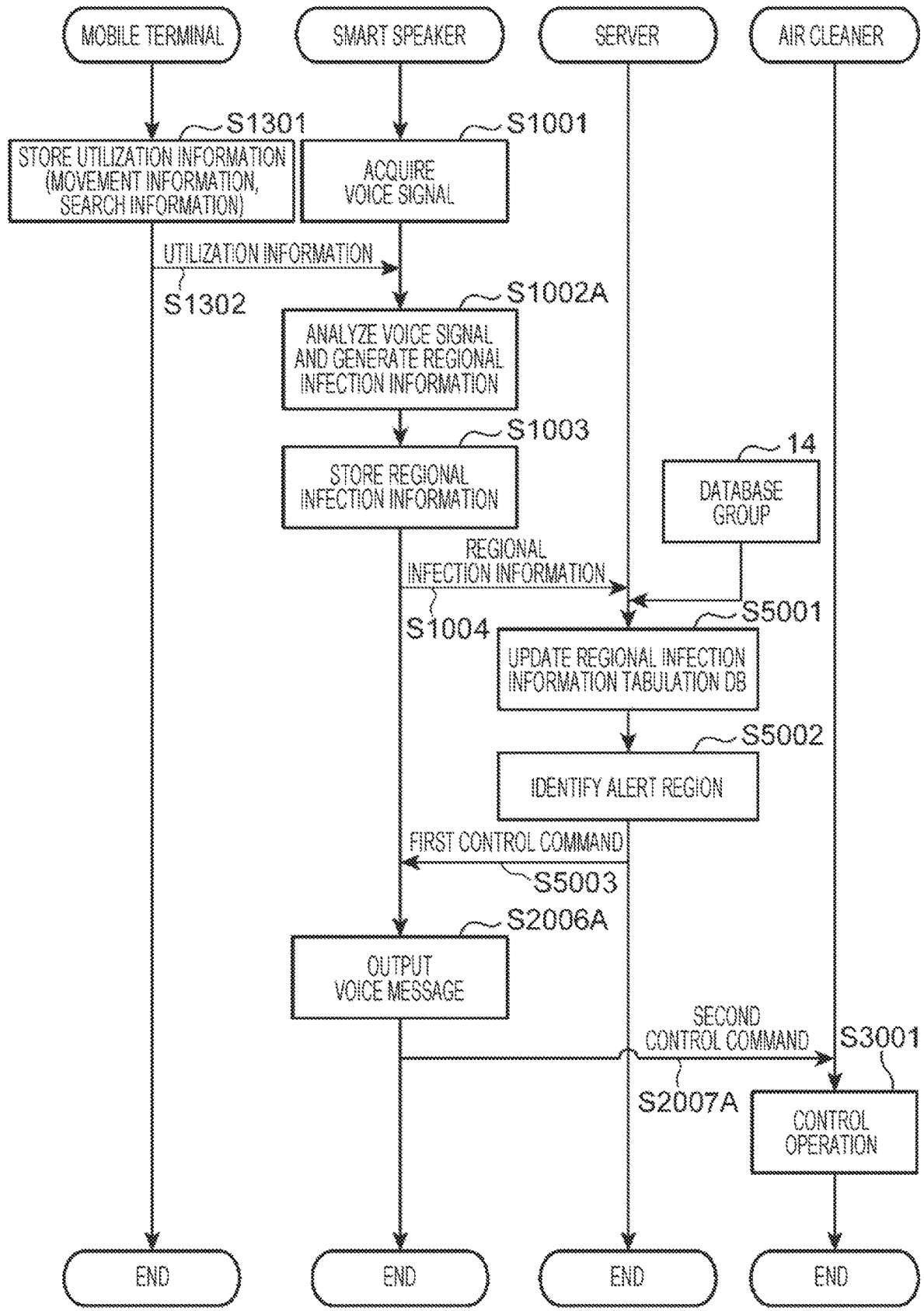
FIG. 21 is a flow chart according to a modification of FIG. 20.

FIG. 21 is a flow chart according to a modification of FIG. 20. The flow chart of FIG. 21 further includes, in addition to the flow chart of FIG. 20, a process that is performed by a mobile terminal 3. Steps of FIG. 21 that are identical to those of FIG. 20 are assigned the same step numbers, and a description of the steps is omitted.

In step S1301, the controller 303 of the mobile terminal 3 stores utilization information in the memory 302. Note here that the utilization information contains movement information and search information, and the controller 303 needs only store movement information in the movement information DB 11 at fixed time intervals and, every time a search word is entered by the user, store search information in the search information DB 12.

In step S1302, the communicator 304 of the mobile terminal 3 transmits the utilization information to the smart speaker 2B. At this point, the controller 303 of the mobile terminal 3 needs only incorporate, into the utilization information, those ones of the pieces of movement information in the movement information DB 11 which were stored during a certain period of time from the present to the past and incorporate, into the utilization information, those ones of the pieces of search information in the search information DB 12 which were stored during a certain period of time from the present to the past.

The mobile terminal 3 may periodically transmit the utilization information to the smart speaker 2B or may transmit the utilization information to the smart speaker 2B upon a request from the smart speaker 2B.

In step S1002A, which follows step S1001, the processor 210 of the smart speaker 2B generates regional infection information by using the utilization information when needed in addition to analyzing the voice signal. For example, suppose that a time word was able to be identified from the voice recognition content but a place word was unable to be identified from the voice recognition content. In this case, with movement information on the utterer, the processor 210 needs only use the movement information to identify the place where the utterer was at the date and time indicated by the time word.

Thus, according to the flow chart of FIG. 21, if the voice recognition content is insufficient in information in generating regional infection information, the insufficient information is supplemented by the utilization information from the mobile terminal 3, so that as many situations as possible where no regional infection information is generated can be avoided.

It should be noted that the following modifications of Embodiments 2 and 3 may be adopted.

(2-1) Although, in each of Embodiments 2 and 3, the second control command is transmitted to the air cleaner 13 from the smart speaker 2A_2, which has received the first control command, as shown in FIG. 15, this is not intended to limit the present disclosure. For example, the second control command may be transmitted to the air cleaner 13 directly from the smart speaker 2A_1, which has transmitted the first control command. In this case, the smart speaker 2A_1 needs only store regions in which smart speakers 2A are installed and communication addresses in association with each other. The same applies to Embodiment 3. That is, in FIG. 20, the second control command may be transmitted to the air cleaner 13 directly from the server 1A, which has transmitted the first control command.

(2-2) In each of Embodiments 2 and 3, the regional infection information generator 213 may calculate, in generating regional infection information, a distance of utterance between a place word and a disease name word as extracted from a voice recognition content and, if the distance of utterance is equal to or greater than a certain value, output through the speaker 240 a question message that asks the user whether a place identified from the place word is correct. Then, in a case where the user has uttered affirmatively, the regional infection information generator 213 needs only generate regional infection information associating the place identified from the place word with an infection alert level identified from the disease name word and store the regional infection information in the regional infection information DB 9. As the distance of utterance, the number of characters from the disease name word to the place word in text data representing the voice recognition content can be adopted. This is based on the idea that a larger number of characters from the disease name word to the place word leads to a drop in association between the words.

(2-3) In generating regional infection information, the regional infection information generator 213 may identify, from movement information on a constituent member (infected person), identified from a voice recognition content, whose infection alert level is equal to or higher than a certain level, facilities such as stations, commercial facilities, and schools located on a route of movement of the constituent member where multitudes of people gather, and may notify a different smart speaker 2A or 2B or the server 1A of the facilities thus identified through the communicator 230. Moreover, the different smart speaker 2A or 2B or the server 1A may raise, by predetermined values, infection risk values of places and districts of the facilities thus notified. This makes it possible to more accurately calculate infection risk values in places and districts where there are facilities located on a route of movement of an infected person.

(2-4) Although, in each of Embodiments 2 and 3, a first control command is transmitted to a smart speaker 2A or 2B in a region whose infection risk value is equal to or higher than a threshold, this is not intended to limit the present disclosure and a first control command may be transmitted to all smart speakers 2A or 2B. In this case, it is only necessary to transmit, to the smart speakers 2A or 2B, a first control command that causes the smart speakers 2A or 2B to output different voice messages depending on infection risk values. For example, as mentioned above, it is only necessary to transmit a first control command that causes the smart speakers 2A or 2B to output a voice message determined in advance according to whether an infection risk value is high, medium, or low. Further, to a smart speaker 2A or 2B installed in a region whose infection risk value is equal to or lower than the threshold, it is only necessary to transmit a first control command that causes the smart speaker 2A or 2B to output a voice message indicating that although the infectious disease is not currently epidemic in this district, the infectious disease is currently epidemic in a different district.

(2-5) Although each of Embodiments 2 and 3 has been described on the assumption that the weights shown in FIG. 14 vary, this is not intended to limit the present disclosure and the weights may take on predetermined fixed values. In this case, for example, the weighting values assigned to the levels "5" to "1" with respect to the numbers of reported cases by infection alert level need only take on "5" to "1".

(2-6) Although, in each of the embodiments described above, a voice message is generated on the basis of an infection risk value described in the regional infection information tabulation DB 50A shown in FIG. 14, this is not intended to limit the present disclosure. For example, a voice message may be generated from the regional infection information DB 9 shown in FIG. 5. For example, suppose a smart speaker 2A or 2B has accepted an utterance from a user to the effect that he/she would like to know where there is an epidemic of an infectious disease. In this case, the smart speaker 2A or 2B may calculate a total value of infection alert levels over a certain period of time (e.g. today) in the regional infection information and generate a voice message indicating that a region where the total value is equal to or higher than a threshold is an epidemic place where there is an epidemic of an infectious disease.

Embodiment 4

Figure 22:
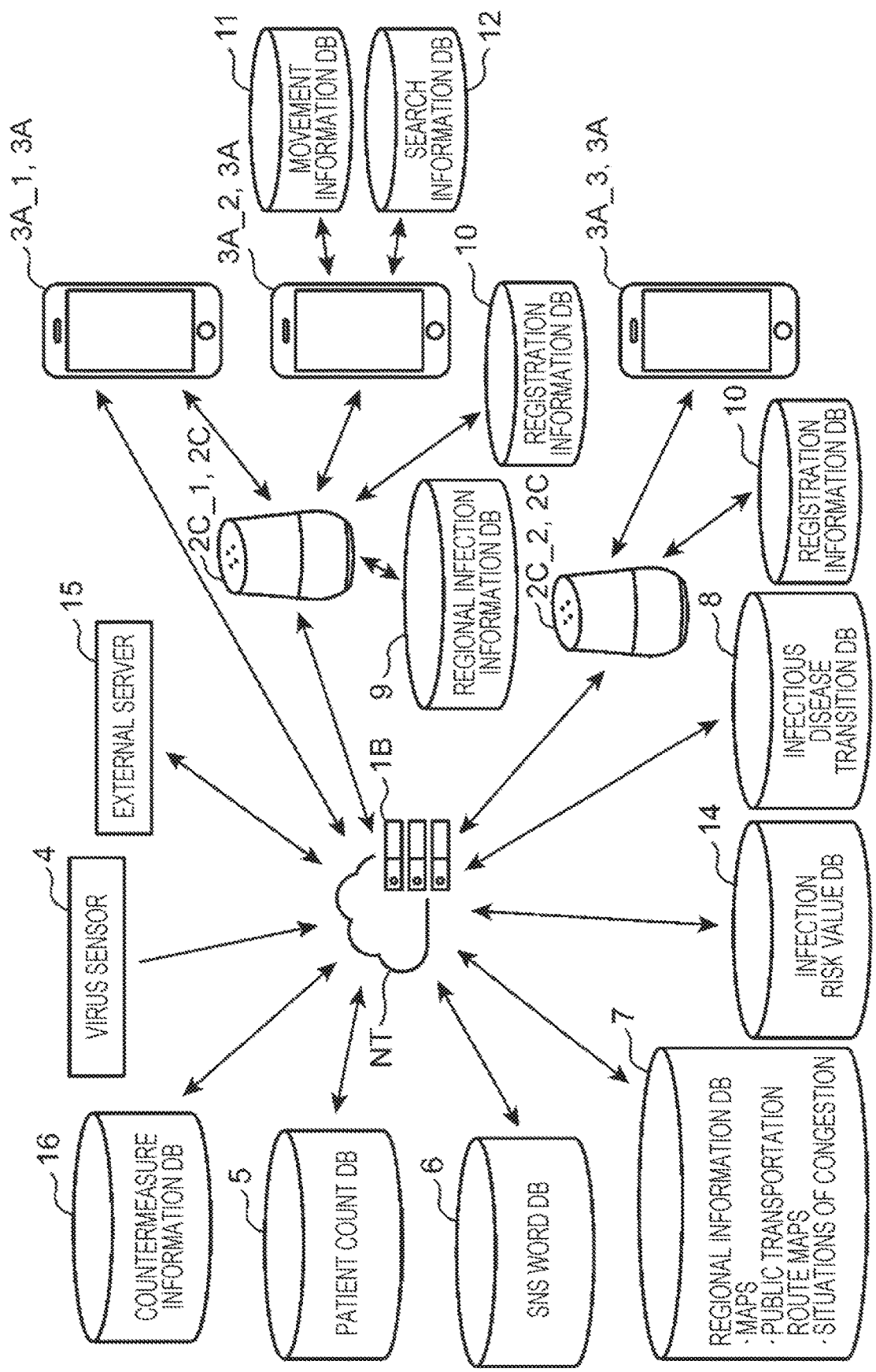
FIG. 22 is a diagram showing an example of a network configuration of an information providing system according to Embodiment 4 of the present disclosure.

FIG. 22 is a diagram showing an example of a network configuration of an information providing system according to Embodiment 4 of the present disclosure. In a service coverage region including a region of residence of a user to which a service is applied and one or more regions located within a certain range from the region, the information providing system according to Embodiment 4 serves to generate mapping data associating a particular place on map data and the number of possibly-infected persons in the place and provide the user with the mapping data. A description of contents of the present embodiment that are identical to those of Embodiments 1 to 3 is omitted.

The information providing system includes a server 1B, smart speakers 2C, mobile terminals 3A, a virus sensor 4, a patient count DB (database) 5, an SNS word DB 6, a regional information DB 7, an infectious disease transition DB 8, an regional infection information DB 9, registration information DBs 10, a movement information DB 11, a search information DB 12, and a countermeasure information DB 16, an infection risk value DB 14, and an external server 15.

All of these components from the server 1B to the infection risk value DB 14 are communicably connected to one another via a network NT.

The server 1B is for example a cloud server constituted by one or more computers, and generates the aforementioned mapping data and transmits the mapping data to the mobile terminals 3A.

Each of the smart speakers 2C is installed, for example, in a user's house. The smart speaker 2C is an example of the voice recognition device. In the example shown in FIG. 22, two smart speakers 2C_1 and 2C_2 are illustrated; however, this is merely an example, and the number of smart speakers 2C may be 1 or may be not smaller than 3.

Each of the mobile terminals 3A is a device that is possessed by a user living in a house in which a smart speaker 2C is installed. The mobile terminal 3A is constituted, for example, by a portable information processing device such as a smartphone, a tablet terminal, or a push-button mobile phone. In the example shown in FIG. 22, three mobile terminals 3A_1, 3A_2, and 3A_3 are illustrated; however, this is merely an example, and the number of mobile terminals 3A may be 1, may be 2, or may be not smaller than 4.

In Embodiment 4, the regional information DB 7 is a database assembled on the external server 15, which is administered by an administrator of the information providing service, and is connected to the network NT via the external server 15. Geographical data contained in regional data is stored in the regional information DB 7, for example, by the external server 15 importing geographical data provided by a search engine operator on the Internet. Further, public transportation route map data contained in the regional data is stored in the regional information DB 7, for example, by the external server 15 importing route map data disclosed on the Internet by railroad companies, bus companies, and the like. Further, congestion situation data contained in the regional data is stored in the regional information DB 7, for example, by the external server 15 importing congestion situation data generated by a search engine operator on the Internet.

The regional infection information DB 9 is created on the basis of histories of utterances of users phonetically recognized by a smart speaker 2C, and stores regional infection information representing infection alert levels for each region. Each of the registration information DBs 10 stores personal information on constituent members living in a house in which a smart speaker 2C is installed. The regional infection information DB 9 and the registration information DB 10 are stored, for example, in a memory of the smart speaker 2C. Note, however, that this is merely an example and the regional infection information DB 9 and the registration information DB 10 may be stored in the external server 15.

The movement information DB 11 stores movement information on a user who possesses a mobile terminal 3A. The movement information is for example data associating positional information calculated by a GPS sensor of the mobile terminal 3A with the time of calculation. The movement information DB 11 is stored in a memory of the mobile terminal 3A. Note, however, that this is merely an example and the movement information DB 11 may be stored in the external server 15.

The search information DB 12 stores search information representing a history of searches done by the user on a search engine that is executed on the mobile terminal 3A. The search information is for example data associating a search word entered into the search engine with the time of search.

The countermeasure information DB 13 is installed in various types of facilities such as large commercial facilities, civic centers, and libraries within the service coverage region, and stores measurement data including measurement data taken by an infection control sensor 20 (FIG. 23) that measures ambient environmental information.

The infection risk value DB 14 is a database, constituted by the external server 15, that stores an infection risk value indicating a risk of infection in each place. Details of the calculation of an infection risk value will be described later.

The external server 15 is a cloud server constituted by one or more computers, and stores the regional information DB 7, the countermeasure information DB 13, and the infection risk value DB 14. Further, the external server 15 calculates an infection risk value for each place and stores the infection risk value in the infection risk value DB 14.

Figure 23:
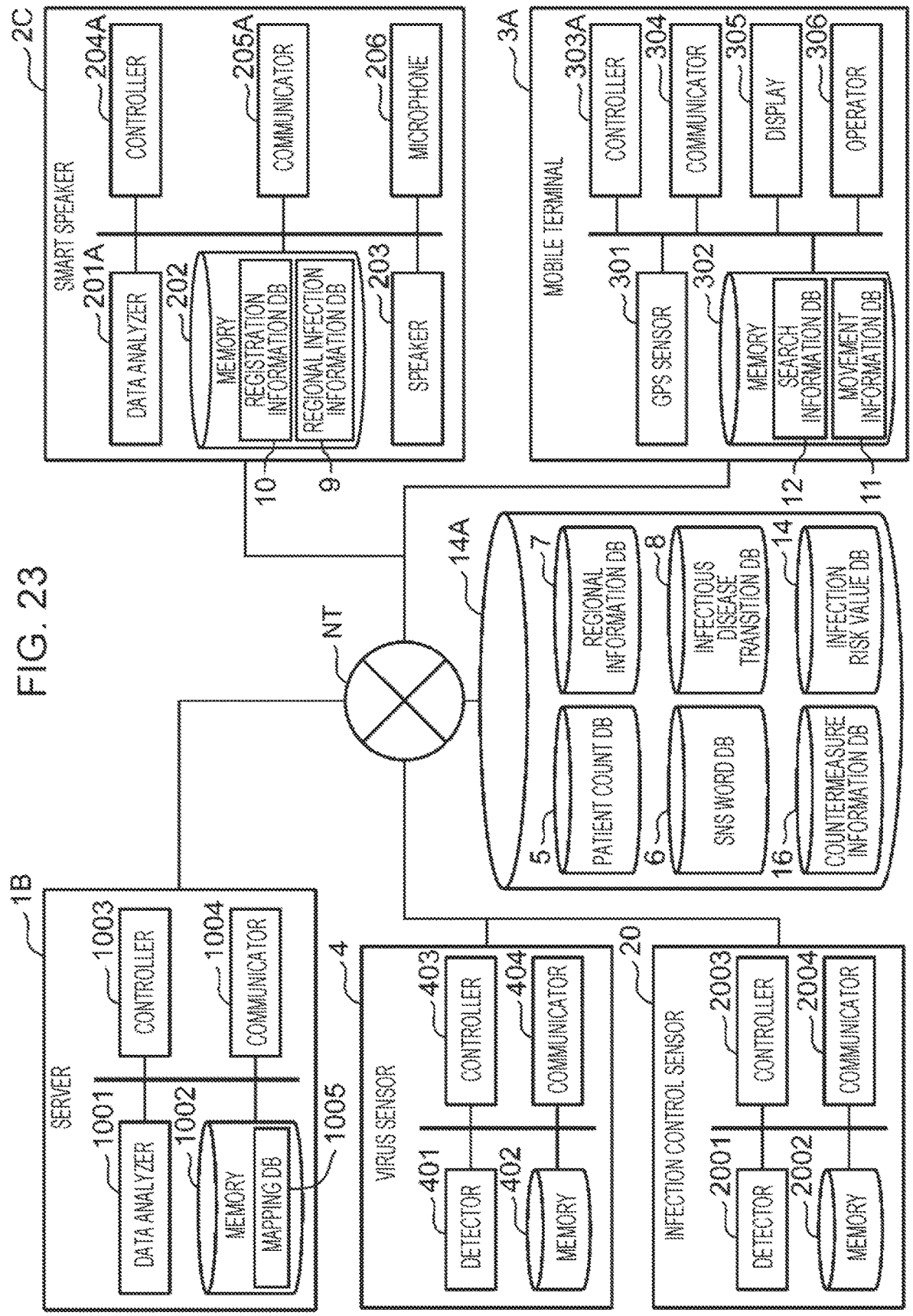
FIG. 23 is a block diagram showing an example configuration of the information providing system shown in FIG. 22.

FIG. 23 is a block diagram showing an example configuration of the information providing system shown in FIG. 22. Each of the smart speakers 2C includes a data analyzer 201A, a memory 202, a speaker 203, a controller 204A, a communicator 205A, and a microphone 206. The data analyzer 201A is constituted by a processor that performs a voice recognition process on a voice signal obtained by the microphone 206 collecting sounds. Blocks of FIG. 23 that overlap those of FIG. 2 are assigned the same signs, and a description of the blocks is omitted.

The data analyzer 201A phonetically recognizes a voice signal obtained by the microphone 206 collecting sounds, identifies a possibly-infected person who is possibly infected with an infectious disease and a possibility of infection of the possibly-infected person, and generates regional infection information (which is an example of the first infection information). The data analyzer 201A estimates, from an utterance content of the voice signal, the infectious disease with which the possibly-infected person is possibly infected.

The communicator 205A is constituted by a communication device through which the smart speaker 2C is connected to the network NT. For example, the communicator 205A transmits to a mobile terminal 3A of the possibly-infected person, the regional infection information generated by the data analyzer 201A.

Each of the mobile terminals 3A includes a GPS sensor 301, a memory 302, a controller 303A, a communicator 304, a display unit 305 (which is an example of the display), and an operator 306.

In addition to the functions of the controller 303 shown in FIG. 2, the controller 303A further reads out positional information over the past period from the movement information DB 11 in a case where the communicator 205A has received regional infection information from the smart speaker 2C, generates coordinate data associating the positional information thus read out with the regional infection information thus received, and transmits the coordinate data to the server 1B through the communicator 205A.

The server 1B includes a data analyzer 1001, a memory 1002, a controller 1003, and a communicator 1004. The data analyzer 1001 is constituted, for example, by a CPU. In a case where the communicator 1004 has received coordinate data from the mobile terminal 3A, the data analyzer 1001 uses the coordinate data to generate mapping data associating a particular place on map data with the number of possibly-infected persons in the place. Moreover, the data analyzer 1001 stores the mapping data thus generated in the mapping DB 1005. The map data refers to geographical data, and the particular place corresponds to a place extracted from a voice recognition content or a predetermined place on the geographical data.

The memory 1002 is constituted, for example, by a semiconductor memory, and stores the mapping DB 1005. The mapping DB 1005 will be described in detail later.

The controller 1003 is constituted, for example, by a CPU. In a case where the communicator 1004 has received a request from a mobile terminal 3A, the controller 1003 transmits the mapping data through the communicator 1004 to the mobile terminal 3A that transmitted the request. The communicator 1004 is a communication device through which the server 1B is connected to the network NT. Note here that the mobile terminal 3A that transmits a request encompasses a mobile terminal 3A of a possibly-infected person and a mobile terminal 3A of a person to which any other service is applied.

The infection control sensor 20 is constituted, for example, by an air cleaner, and includes a detector 2001, a memory 2002, a controller 2003, and a communicator 2004. The detector 2001 is constituted, for example, by a temperature sensor and a humidity sensor, and detects ambient temperature and humidity. The detector 2001 acquires, from the memory 2002, a set value of the infection control sensor 20 as set by the controller 2003. Note here that adopted examples of the set value of the infection control sensor 20 include set values, such as "High", "Medium", and "Low", of the purification capacity of the infection control sensor 20.

The memory 2002 is constituted, for example, by a semiconductor memory, and stores measurement data detected by the detector 2001 and a set value set by the controller 2003.

The controller 2003 is constituted, for example, by a CPU, and exercises overall control of the infection control sensor 20. The communicator 2004 is constituted by a communication device through which the infection control sensor 20 is connected to the network NT.

The database group 14A is a compilation of the patient count DB 5, the SNS word DB 6, the regional information DB 7, the infectious disease transition DB 8, the countermeasure information DB 16, and the infection risk value DB 14, which are shown in FIG. 22, and is assembled on the various servers described with reference FIG. 22.

Since the data configuration of the registration information DB 10 stored in the memory 202 of the smart speaker 2C is identical to that of FIG. 4, a detailed description of the data configuration is omitted.

Note, however, that in Embodiment 4, the "Announcement Setting" shown in the basic information table T11 represents configuration information indicating whether to, upon receiving an utterance command from the server 1B or the external server 15, cause the smart speaker 2C to output a voice message. For example, upon receiving an utterance command from the server 1B or the external server 15 in a case where the announcement setting is ON, the smart speaker 2C outputs a voice message contained in the utterance command. On the other hand, when the smart speaker 2C has received an utterance command from the server 1B in a case where the announcement setting is OFF, the smart speaker 2C does not output a voice message contained in the utterance command.

Further, in Embodiment 4, the "Device Control Setting" shown in the basic information table T11 represents configuration information indicating whether to, upon receiving an utterance command from the server 1B or the external server 15, transmit to a corresponding air cleaner a control command that brings the corresponding air cleaner into operation. For example, if the device control setting is "Automatic", the smart speaker 2C transmits the control command to the corresponding air cleaner. On the other hand, if the device control setting is not "Automatic", the smart speaker 2C does not transmit the control command to the corresponding air cleaner. Note here that if the smart speaker 2C is installed in a house, the corresponding air cleaner is an air cleaner installed in the house.

Since the data configuration of the regional infection information DB 9 stored in the memory 202 of the smart speaker 2C is identical to that of FIG. 5, a detailed description of the data configuration is omitted.

Note, however, that in Embodiment 4, the "Place" represents places extracted from the voice recognition contents. The "District" represents districts to which the extracted places belong.

Further, in Embodiment 4, the "Ancillary Data" Column has stored therein movement information indicating routes of movement of the constituent members registered in the "Subject No." Column. The movement information is acquired from the movement information DB 11 of a mobile terminal 3A possessed by a constituent member.

In the "Ancillary Data" Column, the phrase "Movement Information/Smartphone" indicates that the device from which the movement information was acquired is a mobile terminal 3A. Further, as the movement information registered in the "Ancillary Data", movement information over the past period based on the "Time" of the voice recognition contents is adopted. Storing movement information in this way makes it possible to identify a region that a constituent member with a high possibility of infection dropped by and, using the place thus identified, identify an epidemic place where there is an epidemic of an infectious disease.

Since the voice recognition process that is performed by the data analyzer 201A of the smart speaker 2C is described with reference to the same diagram as FIG. 6, a detailed description of the voice recognition process is omitted.

Note, however, that in the example shown in the first row, since the utterer "Taro" is a person who is possibly infected with an infectious disease, i.e. a possibly-infected person, "1", which is the identifier of "Taro", is stored in the "Subject No".

FIG. 24 is a diagram showing an example of a data configuration of the mapping DB 1005 stored in the memory 1002 of the server 1B. The mapping DB 1005 assigns one piece of mapping data to one record, and stores time shifts in the number of possibly-infected persons and environmental information in one or more places.

The "Place" represents places contained in coordinate data transmitted from mobile terminals 3A, i.e. "places" contained in the regional infection information DB 9 shown in FIG. 5. Alternatively, the "Place" may represent predetermined places, such as large commercial facilities, civic centers, schools, hospitals, and stations, in the service coverage region where multitudes of people gather. In the following, these places are referred to collectively as "particular places".

In the example shown in FIG. 24, the "AA Shopping Center" and the "CC Supermarket" are identified as particular places. Further, since the numbers of possibly-infected persons in more specific places, such as the "Star Square" and the "Moon Square", have been identified in the "AA Shopping Center", the numbers of possibly-infected persons are stored for these places, too. The specific places have been identified in the AA Shopping Center because the "Star Square of the AA Shopping Center" and the "Moon Square of the AA Shopping Center" were stored in the place column of the regional infection information shown in FIG. 5, or because the settings were configured in advance for the AA Shopping Center such that the Star Square and the Moon Square are set as particular places.

Although, in this example, the number of possibly-infected persons in each particular place is calculated on an hourly basis, e.g. at 9 o'clock on January 18th, 2018, at 10 o'clock on Jan. 18, 2018, and so on, this hourly basis is merely an example and the number of possibly-infected persons may be calculated every different period of time such as one minute, ten minutes, or two hours.

With 10 o'clock on Jan. 18, 2018 taken as an example, first, the data analyzer 1001 extracts movement information on the possibly-infected persons from coordinate data transmitted from mobile terminals 3A during the time of day from the time (9 o'clock on Jan. 18, 2018) at which the previous numbers of possibly-infected persons were calculated to "10 o'clock" of the same date. Specifically, the movement data stored in the "Ancillary Data" Column of the regional infection information (FIG. 5) contained in the coordinate data is extracted.

Then, the data analyzer 1001 determines, from the movement information thus extracted, whether the possibly-infected persons stayed in the particular places for a predetermined period of time or longer during this time of day. Note here adoptable examples of the predetermined period of time include periods of time such as one minute, two minutes, five minutes, and ten minutes. Further, in the example of the AA Shopping Center, the determination as to whether the possibly-infected persons are in the particular place is made, for example, by identifying the latitude and longitude ranges of the AA Shopping Center from the geographical data and determining whether latitudes and longitudes indicated by the movement information on the possibly-infected persons fall within these latitude and longitude ranges. Alternatively, the determination may be made by determining whether the latitudes and longitudes of the possibly-infected persons are located within a certain range from the location of the center of the AA Shopping Center.

Then, the data analyzer 1001 calculates the number of possibly-infected persons for each particular place by tabulating, for each particular place, the number of possibly-infected persons who stayed for the predetermined period of time or longer, and stores the number of possibly-infected persons in the column concerned of the mapping DB 1005.

In the example shown in FIG. 24, since movement information on eight possibly-infected persons indicates that they stayed in the "Star Square of the AA Shopping Center" for the predetermined period of time or longer during the time of day from 9 o'clock to 10 o'clock, the number of possibly-infected persons in the "Star Square of the AA Shopping Center" at 10 o'clock on Jan. 18, 2018 is calculated to be "8". The numbers of possibly-infected persons in other particular places are calculated in a similar manner.

The environmental information represents ambient environmental information and infection control information on a particular place and, for example, is acquired from an infection control sensor 20 installed in the particular place. In the example shown in FIG. 24, the environmental information contains "Temperature", "Humidity", "Set Value", "Risk of Infection", and "Infection Risk Value". A set value represents the set value, such as "High", "Medium", or "Low", of the purification capacity of the infection control sensor 20. In a case where the infection control sensor 20 is not operating, OFF is stored as a set value. When the infection control sensor 20 is operating, it is conceivable that measures to control infectious diseases are being taken in the particular place; therefore, in a case where the "Set Value" is "High", "Medium", or "Low", it is determined that environmental measures are being taken.

A risk of infection represents a risk of infection in a particular place as calculated by the data analyzer 1001. The risk of infection is calculated, for example, in the following manner. First, the data analyzer 1001 calculates the density of infected persons in the particular place. For example, the data analyzer 1001 calculates the density of infection persons according to nr=n/S, where S is the area of the AA Shopping Center as acquired from the regional information DB 7, n is the current number of epidemic infected persons in the AA Shopping Center, and nr is the density of infected persons. Next, the data analyzer 1001 calculates an infection risk evaluation value $\alpha$ ($=nr \cdot kt \cdot km \cdot kl$) by multiplying the number of infected persons by a temperature coefficient kt determined from the current temperature of the AA Shopping Center, a humidity coefficient km determined from the humidity, and a set value coefficient kl determined from the set value. For example, since the influenza virus more likely to grow at a lower humidity and a lower temperature, the humidity coefficient km and the temperature coefficient kt are set to larger values with decrease in humidity and temperature. Further, since the virus decreases as the set value becomes larger, the set value coefficient kl is set to a smaller value as the set value becomes larger.

Then, the data analyzer 1001 calculates the risk of infection according to which of the ranges of numerical values determined in advance for "High", "Medium", and "Low", respectively, the infection risk evaluation value $\alpha$ belongs to. That is, the risk of infection is ranked on a three-grade scale of "High", "Medium", and "Low". Note, however, that this is merely an example and the risk of infection may be ranked on a two-grade scaled or may be ranked on a four-or-more-grade scale.

The infection risk value is an index that numerically expresses a risk of infection in a particular place as obtained by the external server 15 analyzing a large number of pieces regional infection information transmitted from the smart speakers 2C. The infection risk value is stored in the infection risk value DB 14, and the server 1B acquires the infection risk value of a particular place from the infection risk value DB 14.

The infection risk value is calculated by the external server 15 in the following manner. First, the external server 15 receives regional infection information (which is an example the second infection information) from the smart speakers 2C at any time. Then, the external server 15 calculates the number of reported cases for each infection alert level in the particular place by classifying the regional infection information for each particular place and each infection alert level. Referring to FIG. 5, suppose that "10", "8", "7", "15", and "20" pieces of regional infection information with infection alert levels of "5" to 1" have been received regarding the AB Corporation, respectively. In this case, the external server 15 calculates the numbers of reported cases of the infection alert levels "5" to "1" to be "10", "8", "7", "15", and "20" regarding the AB Corporation, respectively.

Next, the external server 15 calculates the infection risk value by subjecting the numbers of reported cases to weighted addition using weights assigned in advance to the infection alert levels "5" to "1", respectively. For example, assuming that the weights assigned to the infection alert levels "5" to "1" are "k5", "k4", "k3", "k2", and "k1", respectively, the infection risk value of the AB Corporation is calculated as follows:

Infection Risk Value of *AB* Corporation=$k5 \cdot 10 + k4 \cdot 8 + k3 \cdot 7 + k2 \cdot 15 + k1 \cdot 20$ By executing such a process for each particular place, the external sever 15 calculates an infection risk value for each particular place. At this point, the external server 15 calculates an infection risk value every predetermined period of time (e.g. one day) and stores such infection risk values in chronological order in the infection risk value DB 14. Therefore, upon receiving from the server 1B a request for acquisition of an infection risk value, the external server 15 needs only transmit the latest infection risk value to the server 1B.

Figure 25:
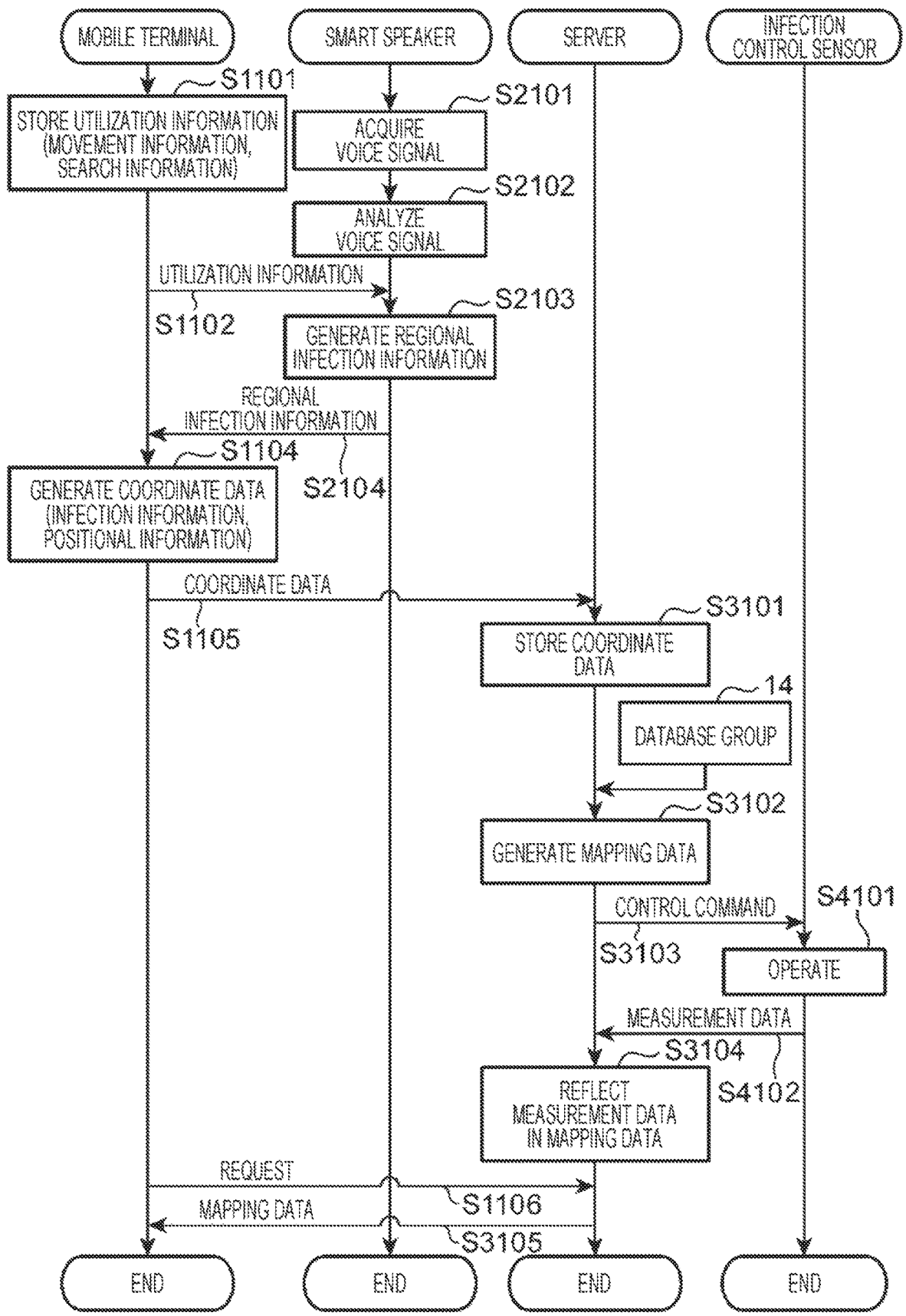
FIG. 25 is a flow chart showing an example of a process that is performed by the information providing system shown in FIG. 22.

FIG. 25 is a flowchart showing an example of a process that is performed by the information providing system shown in FIG. 22. In step S1101, the controller 303A of a mobile terminal 3A stores utilization information in the memory 302. Note here that the utilization information contains movement information and search information, and the controller 303A needs only store movement information in the movement information DB 11 at fixed time intervals and, every time a search word is entered by the user, store search information in the search information DB 12.

In step S1102, the communicator 304 of the mobile terminal 3A transmits the utilization information to a smart speaker 2C. At this point, the controller 303A of the mobile terminal 3A needs only incorporate, into the utilization information, those ones of the pieces of movement information in the movement information DB 11 which were stored during a certain period of time (e.g. one hour) from the present to the past and incorporate, into the utilization information, those ones of the pieces of search information in the search information DB 12 which were stored during a certain period of time (e.g. one hour) from the present to the past. The mobile terminal 3A needs only transmit the utilization information to a predetermined smart speaker 2C installed, for example, in a user's house.

The mobile terminal 3A may periodically (e.g. every one hour) transmit the utilization information to the smart speaker 2C or may transmit the utilization information to the smart speaker 2C upon a request from the smart speaker 2C.

In step S2101, the microphone 206 of the smart speaker 2C c acquires a voice signal by collecting ambient sounds. In step S2102, the data analyzer 201A of the smart speaker 2C analyzes the voice signal. In this example, the voice signal is subjected to a voice recognition process, whereby a voice recognition content such as "I heard that the client I met at work yesterday had the flu" is acquired. Further, in this example, voiceprint data is used, whereby an utterer of this voice recognition content is identified. Further, from this voice recognition content, a disease name word, a place word, a date and time word, and a person word are extracted.

In step S2103, the data analyzer 201A of the smart speaker 2C generates regional infection information using the utilization information transmitted from the mobile terminal 3A and the voice recognition content acquired in step S2102, and stores the regional infection information in the regional infection information DB 9. This causes data to be stored in each column shown in the regional infection information DB 9, so that new regional infection information is added to the regional infection information DB 9. For example, the identifier of the utterer is stored in the "Subject No." Column. The name of an infectious disease as estimated from the disease name word is stored in the "Estimated Name of Infectious Disease" Column. A place and a district estimated from the place word are stored in the "Place" and "District" Columns, respectively. The "Epidemic Period Correction Value" is determined from a time estimated from the date and time word. A possibility of infection estimated from the person word is stored in the "Possibility of Infection" Column. The utilization information is stored in the "Ancillary Data" Column.

In step S2104, the data analyzer 201A of the smart speaker 2C transmits the regional infection information thus generated to a mobile terminal 3A of a possibly-infected person through the communicator 205A. At this point, the possibly-infected person is a constituent member living in the house in which the smart speaker 2C is installed, and the smart speaker 2C has stored in advance in the memory 302 the communication address of a mobile terminal 3A of each constituent member. Therefore, the smart speaker 2C can transmit the regional infection information to the mobile terminal 3A of the possibly-infected person. Further, every time the smart speaker 2C generates regional infection information, the smart speaker 2C needs only transmit the regional infection information to the mobile terminal 3A concerned.

In step S1104, the controller 303A of the mobile terminal 3A generates coordinate data by associating the regional infection information transmitted in step S2104 with positional information. At this point, the controller 303A needs only read out, from the movement information DB 11 and the search information DB 12, movement information and search information over the past period (e.g. one hour) since reception of the regional infection information and incorporate the movement information and the search information into the coordinate data.

In step S1105, the communicator 304 of the mobile terminal 3A transmits the coordinate data generated in step S1104 to the server 1B. After this, the communicator 304 of the mobile terminal 3A periodically (e.g. every one hour) transmits coordinate data to the server 1B, and every time coordinate information is transmitted, step S3102 and subsequent steps are executed, so that mapping data is periodically updated.

In step S3101, the controller 204A of the server 1B accumulates, in the memory 1002, the coordinate data transmitted in step S1105.

In step S3102, the data analyzer 1001 of the server 1B generates mapping data from the coordinate data accumulated in the memory 1002, and stores the mapping data in the mapping DB 1005. Note here that the data analyzer 1001 generates mapping data at predetermined time intervals, and needs only generate mapping data using the coordinate data stored in the memory 1002 during a period of time from generation of the previous mapping data to generation of the current mapping data.

In step S3103, the controller 1003 of the server 1B transmits, to the infection control sensor 20 through the communicator 1004, a control command that brings the infection control sensor 20 into operation. At this point, the controller 1003 needs only generate, with reference to the "Place" shown in FIG. 24, a control command corresponding to the current number of possibly-infected persons. In the example shown in FIG. 24, the number of possibly-infected persons in the Star Square of the AA Shopping Center at 10 o'clock on Jan. 18, 2018 is "8". Further, suppose that "8" is equal to or larger than a predetermined threshold. In this case, the controller 1003 transmits, to the infection control sensor 20, a control command that brings into operation an infection control sensor 20 installed in the Star Square. In this case, the controller 1003 needs only transmit a control command that causes the infection control sensor 20 to operate at a set value of purification capacity corresponding to "8". For example, assuming that the set value is determined on such a rule that the set value is "Low" if the number of possibly-infected persons is 1 to 5, "Medium" if the number of possibly-infected persons is 5 to 10, or "High" if the number of possibly-infected persons is larger than 10, the controller 1003 needs only transmit, to the infection control sensor 20, a control command that causes the infection control sensor 20 to operate at the "Medium" set value. Note here that although the set value contained in the control command is determined according to the number of possibly-infected persons, this is merely an example and the set value may be determined according to the density of infected persons in a particular place.

In step S4101, the controller 2003 of the infection control sensor 20 causes the infection control sensor 20 to operate at the set value according to the control command thus transmitted.

In step S4102, the controller 2003 of the infection control sensor 20 transmits, to the server 1B through the communicator 2004, the measurement data detected by the humidity sensor and temperature sensor, respectively, of the detector 2001 and the current set value stored in the memory 2002.

In step S3104, the data analyzer 1001 of the server 1B reflects the measurement data in the mapping data. For example, suppose that at 10 o'clock on Jan. 18, 2018, measurement data representing a temperature of "24.5° C." and a humidity of "54%" and a set value "Medium" have been transmitted from the infection control sensor 20 installed in the Star Square of the AA Shopping Center. In this case, the data analyzer 1001 needs only store "Temperature: 24.5° C., Humidity: 54%, Set Value: Medium" in the "Environmental Information" Column of the "Star Square" at 10 o'clock on Jan. 18, 2018 shown in FIG. 24.

In step S1106, upon receiving from the user through the operator 306, an instruction to transmit a request, the controller 303A of the mobile terminal 3A transmits a request to the server 1B through the communicator 304. The mobile terminal 3A is installed with a providing application for providing the user with a service of the information providing system, and the request may be transmitted in a case where the user has entered an operation of actuating this providing application. Alternatively, the request may be transmitted in a case where the user has entered a viewing request for map information using this providing application. Alternatively, the request may be transmitted in a case where the providing application has detected that in an existing route search application in the mobile terminal 3A has acquired a route of movement to a destination from the server 1B in accordance with the user's instruction. In this case, a request to acquire mapping data on a particular place located around the route of movement acquired by the route search application may be transmitted. Alternatively, in a case where the providing application has detected that the user has activated a map application in the mobile terminal 3A, a request to acquire mapping data on a particular position within a certain range from a place located in the center of a map screen being viewed by the user may be transmitted.

In step S3105, the communicator 1004 of the server 1B transmits mapping data containing the latest number of possibly-infected person and environmental information from the mapping DB 1005 to the mobile terminal 3A. It should be noted that various aspects may be adopted as to on which particular place to transmit mapping data. For example, upon transmission of a request for a route of movement from the mobile terminal 3A, mapping data on a particular place around the route of movement may be transmitted. Further, mapping data on a particular place located within a certain surrounding range from the current position of the mobile terminal 3A may be transmitted. Alternatively, in a case where the user is viewing a map on the map application of the mobile terminal 3A, mapping data on a particular place located within a certain range from a place located in the center of the map screen may be transmitted. Alternatively, mapping data on all particular places stored in the mapping DB 1005 may be transmitted.

Note here that the server 1B may incorporate a result of detection of virus by the virus sensor 4 in addition to the temperature, the humidity, the set value, the risk of infection, and the infection risk value as the environmental information contained in the mapping data to be transmitted. For example, if a virus sensor 4 is installed in the AA Shopping Center and a result of detection of virus can be acquired from this virus sensor 4, the server 1B needs only incorporate a result of detection of virus in the AA Shopping Center into the mapping data.

Figure 26:
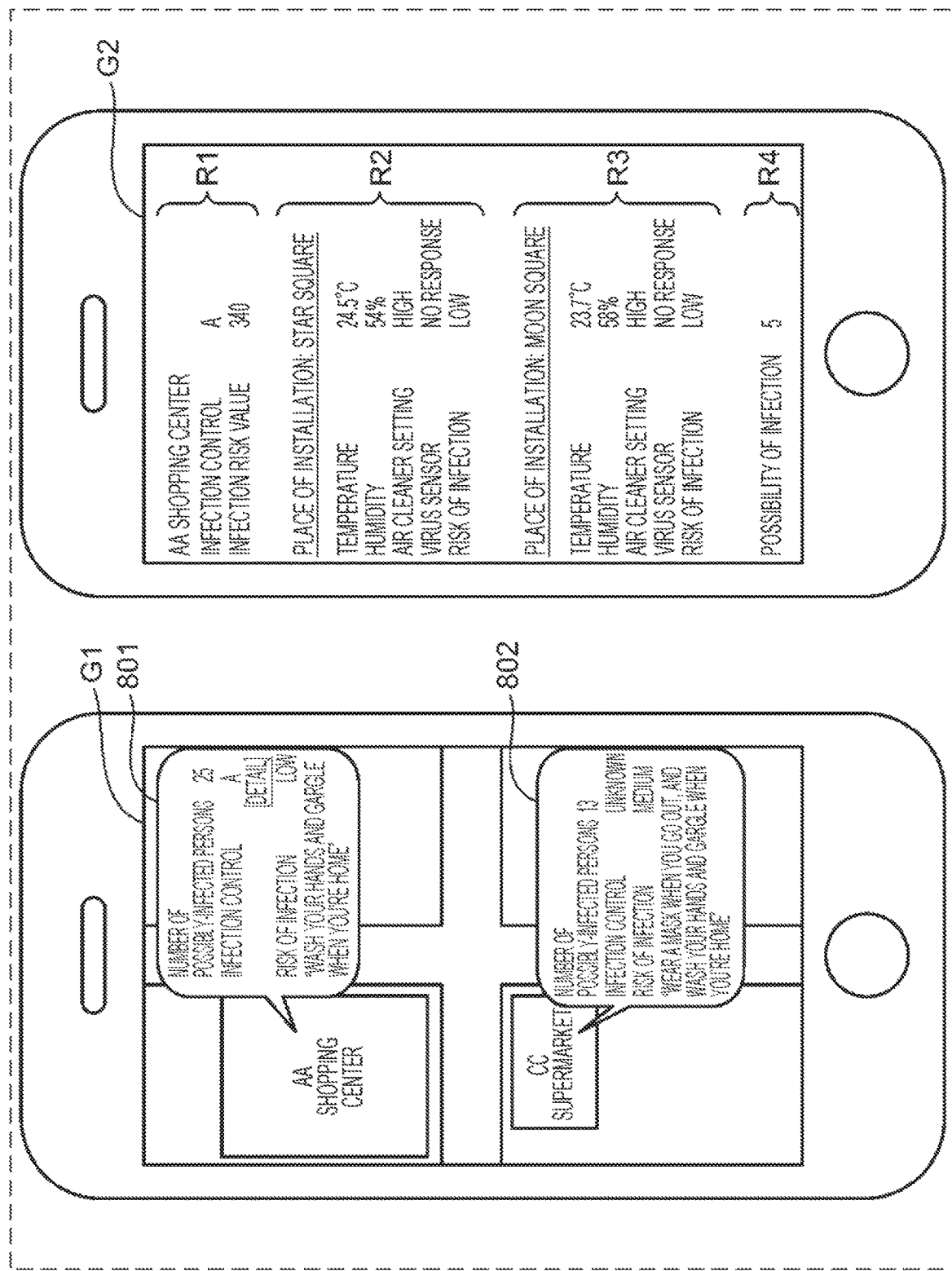
FIG. 26 is a diagram showing display screens that are displayed on a mobile terminal having received mapping data.

FIG. 26 is a diagram showing display screens G1 and G2 that are displayed on a mobile terminal 3A having received mapping data. The display screens G1 and G2 are ones generated by the controller 303A of the mobile terminal 3A using mapping data transmitted from the server 1B.

The display screen G1 displays, on a map image, display columns 801 and 802 each displaying information related to an infectious disease in a corresponding particular place. In this example, in which the AA Shopping Center and the CC Supermarket are identified as particular places, the display column 801, which corresponds to the AA Shopping Center, and the display column 802, which corresponds to the CC supermarket, are displayed. It should be noted that the display screen G1 is displayed by the user activating the providing application or activating the map application.

The display column 801 displays the number of possibly-infected persons, infection control, and a risk of infection in the AA Shopping Center. The number of possibly-infected persons represents the latest number of possibly-infected persons in the AA Shopping Center as stored in the mapping DB 1005.

The infection control represents the presence or absence of infection control in the AA Shopping Center. In this example, in which infection control is being exercised, the mark "A" and the "Detail" button are displayed. When the user enters an operation of selecting the "Detail" button, the controller 303A switches the display screen from the display screen G1 to the display screen G2.

The risk of infection represents a risk of infection calculated for the AA Shopping Center. In this example, the risk of infection is displayed as being "Low", and advice information for infection control corresponding to "Low" is displayed. In this example, the advice information "Wash your hands and gargle when you're home" is displayed. It should be noted that a message determined in advance in correspondence with a "High", "Low", or "Medium" risk of infection is adopted as the advice information.

The display column 802 displays contents which are similar to those of the display column 801. Since no infection control is being exercised in the CC Supermarket, the infection control is displayed as being "Unknown", and the "Detail" button is not displayed. Further, since the risk of infection in the CC Supermarket has been calculated to be medium, the risk of infection is displayed as being "Medium", and "Wear a mask when you go out, and wash your hands and gargle when you're home" is displayed as advice information for infection control corresponding to "Medium".

The display screen G2 is a screen that displays detailed information on infection control being exercised in a particular place and, in this example, displays detailed information on the AA Shopping Center. The display screen G2 includes four display columns R1 to R4. The display column R1 shows infection control being exercised all over the AA Shopping Center. In this example, since infection control is being exercised, the infection control is marked with "A". Whether infection control is being exercised is determined, for example, according to whether the infection control sensor 20 is operating. If the infection control sensor 20 is operating, "A" is displayed. If the infection control sensor 20. If the infection control sensor 20 is not operating, "F" is displayed. Further, the display column R1 displays an infection risk value of "340" in the AA Shopping Center.

The display column R2 shows detailed information on infection control being exercised in the Star Square of the AA Shopping Center. In this example, "Temperature: 24.5° C., Humidity: 54%, Air Cleaner Setting: High, Virus Sensor: No Response, and Risk of Infection: Low" are displayed. These pieces of information are information contained in the mapping data transmitted from the server 1B in step S3103 of FIG. 25. The air cleaner setting represents the set value of the infection control sensor 20.

The display column R3 shows detailed information on infection control being exercised in the Moon Square of the AA Shopping Center. In this example, information which is similar to that of the Star Square is displayed.

The display column R4 shows a possibility of infection calculated for the user concerned by a smart speaker 2C installed in a house of a user of the mobile terminal 3A concerned. Refer to FIG. 5. For example, suppose that this mobile terminal 3A belongs to "Taro", whose identifier is "No. 1". In this case, the display column R4 displays the possibility of infection of Taro as stored in the regional infection information DB 9. In a case where a plurality of possibilities of infection is stored in the regional infection information DB 9 regarding "Taro", the display column R4 may display an average value of the possibilities of infection contained in regional infection information, for example, over the past period (e.g. one day) reckoned from the present. Since the possibility of infection can be calculated only for a user having a smart speaker 2C installed in his/her house, a mobile terminal 3A of a user having no smart speaker 2C installed omits to display the display column R4.

The possibility of infection needs only be calculated, for example, by the mobile terminal 3A acquiring the possibility of infection of the user concerned from the smart speaker 2C of in the house upon activation of the providing application.

Figure 27:
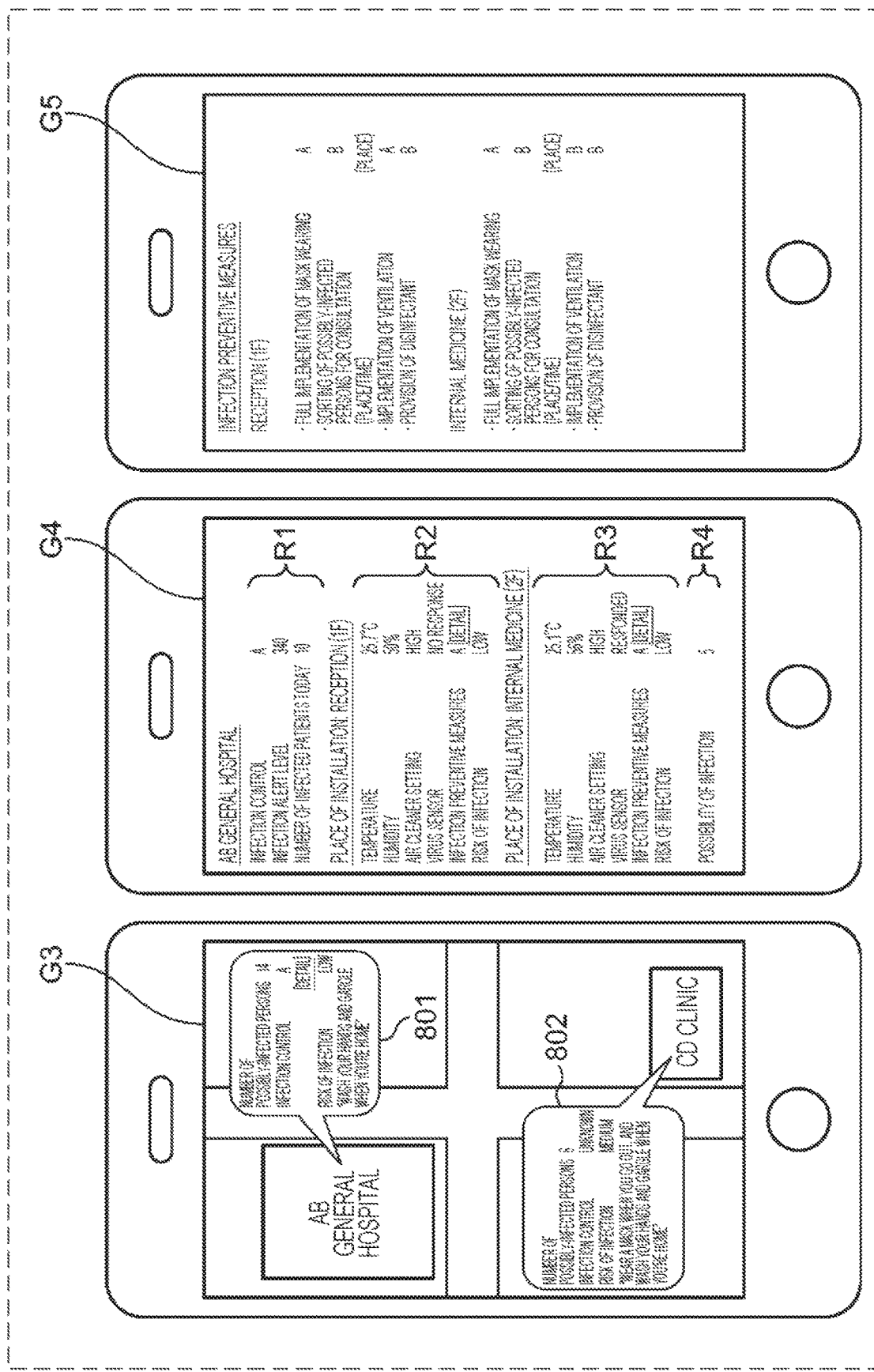
FIG. 27 is a diagram showing other examples of display screens that are displayed on a mobile terminal having received mapping data.

The mapping data may have added thereto environmental information that is used for the calculation of a risk of infection according to a particular place. FIG. 27 is a diagram showing other examples of display screens that are displayed on a mobile terminal 3A having received mapping data. In the example shown in FIG. 27, the particular place is a hospital (AB General Hospital). The display screen G3 corresponds to the display screen G1 of FIG. 26 and includes display columns 801 and 802 that display information related to an infectious disease. The display screen G4 corresponds to the display screen G2 of FIG. 26 and displays detailed information on infection control being exercised in the particular place. In the example shown in FIG. 27, the display column R1 has the item "Number of Infected Patients Today" added thereto. The "Number of Infected Patients Today" represents the number of persons confirmed infected among the patients who consulted doctors in the AB General Hospital on the day. Further, in the example shown in FIG. 27, the display columns R2 and R3 are each provided with an infection preventive measures column. Upon selection of this column, a display screen G5 representing "Infection Preventive Measures" is displayed. The display screen G5 displays items related to infection preventive measures, such as "Full Implementation of Mask Wearing", "Sorting of Possibly-infected Persons for Consultation", "Implementation of Ventilation", and "Provision of Disinfectant", and evaluations corresponding to the respective items. The evaluations indicate the countermeasure degrees of the infection preventive measures. In this example, the evaluations are made using letters such as "A" and "B" ("B" represents a lower degree of implementation than "A").

Thus, according to the present embodiment, a possibly-infected person and a possibility of the possibly-infected person being infected with the infectious disease are identified by the smart speaker 2C, and regional infection information containing the possibility of infection is transmitted to a mobile terminal 3A of the possibly-infected person. Further, upon receiving the regional infection information, the mobile terminal 3A transmits, to the server 1B, coordinate data associating positional information on the mobile terminal 3A with the regional infection information. This allows the server 1B to acquire positional information on the possibly-infected person from the mobile terminal 3A of the possibly-infected person, and to accurately and timely identify where and about how many possibly-infected persons are present. Moreover, mapping data associating the place thus identified with the number of possibly-infected persons thus identified is transmitted to the mobile terminal 3A, and display screens G1 and G2 based on the mapping data are displayed on the mobile terminal 3A. This allows the user of the mobile terminal 3A, for example, to recognize about how many possibly-infected persons are present in a place he/she is going to visit, and to take appropriate countermeasures against an infectious disease.

It should be noted that the following modifications of Embodiment 4 may be adopted.

(4-1) Although, in step S1106 of the flow chart of FIG. 25, a request is transmitted from a mobile terminal 3A that has transmitted coordinate data to the server 1B, i.e. a mobile terminal 3A of a possibly-infected person, this is not intended to limit the present disclosure. For example, a request may be transmitted from a mobile terminal 3A of a person who is different from the possibly-infected person. In this case, in step S3105, the server 1B needs only transmit mapping data to the mobile terminal 3A of the person concerned.

(4-2) Although, in step S4102 of the flow chart of FIG. 25, the server 1B receives measurement data from the infection control sensor 20, this is not intended to limit the present disclosure. For example, the server 1B may receive measurement data on a particular place from the countermeasure information DB 13. In this case, in a case where the virus sensor 4 accumulates measurement data in the countermeasure information DB 13, too, the server 1B needs only acquire the measurement data of the virus sensor 20 in addition to the measurement data of the infection control sensor 20 from the countermeasure information DB 13.

What is claimed is:

1. A method for providing information through an information providing system that provides information related to an infectious disease, the method comprising:
   acquiring a voice signal from one or more voice recognition devices connected to a computer of the information providing system via a network;
   analyzing the voice signal by the one or more voice recognition devices;
   obtaining, by the one or more voice recognition devices, regional infection information from the voice signal, wherein the regional infection information indicates one or more infection alert levels and one or more regions associated with the one or more infection alert levels;
   calculating, based on the regional infection information, an infection risk value representing a magnitude of a risk of infection in each of the one or more regions; and
   generating output information in accordance with the infection risk value for each of the one or more regions,
   acquiring the number of users in each of the one or more regions and an assumed duration of stay for which the users stay in each of the one or more regions, wherein the infection risk value of each of the one or more regions is calculated using a first correction coefficient of a region corresponding to the infection risk value, and the first correction coefficient is a coefficient that increases the infection risk value of the corresponding region as at least one selected from the group consisting of the number of users in the corresponding region and the assumed duration of stay for which the users stay in the corresponding region increases;
   wherein analyzing the voice signal by the one or more voice recognition devices comprising:
   recognizing the voice signal acquired by the one or more voice recognition devices;
   extracting first voice data containing a disease name word out of the voice signal;
   extracting second voice data from a voice signal obtained during a certain period of time before and after a time that the first voice data was obtained;
   identifying a place associated with the first voice data from the second voice data;
   identifying a date and time word and a person word from the second voice data;
   identifying an infection alert level based on the disease name word; and
   generating the regional infection information associating the identified place corresponding to one of the one or more regions, the date and time word, and the person word, with the identified infection alert level.

2. The method according to claim 1, wherein the infection risk value is calculated by calculating the number of reported cases for each of the one or more infection alert levels in each of the one or more regions, assigning, to the number of reported cases, a weight corresponding to the one or more infection alert levels, and evaluating the number of reported cases assigned the weight.

3. The method according to claim 1, wherein the one or more infection alert levels are estimated by the one or more voice recognition devices using a voice recognition content obtained by the one or more voice recognition devices analyzing the voice signal.

4. The method according to claim 1, further comprising acquiring, from a social network service server, information containing a regional infection word indicating an epidemic of the infectious disease in the one or more regions and a frequency of use of the regional infection word,
   wherein the infection risk value of each of the one or more regions is calculated using a second correction coefficient that increases the infection risk value of a region corresponding to the infection risk value as the frequency of use of the regional infection word in the region corresponding to the infection risk value becomes higher.

5. The method according to claim 1, further comprising acquiring patient count data representing the number of patients infected with the infectious disease in each of the one or more regions,
   wherein the infection risk value of each of the one or more regions is calculated using a third correction coefficient that increase the infection risk value of a region corresponding to the infection risk value as the number of patients in the region corresponding to the infection risk value increases.

6. The method according to claim 1, further comprising acquiring a measured value from a virus sensor installed in each of the one or more regions,
   wherein the infection risk value of a region corresponding to the infection risk value increases as the measured value of the virus sensor installed in the region corresponding to the infection risk value becomes larger.

7. The method according to claim 1, further comprising, for each of the one or more regions, transmitting the output information via the network to a device existing in a region corresponding to the output information, wherein
   the device is a voice output device, and
   the output information is a first control command that causes the voice output device to output a voice message serving as a notification of a risk of infection corresponding to the infection risk value.

8. The method according to claim 1, further comprising, for each of the one or more regions, transmitting the output information via the network to a device existing in a region corresponding to the output information, wherein
   the device is an air cleaner, and
   the output information is a second control command that brings the air cleaner into operation.

9. The method according to claim 1, wherein analyzing the voice signal by the one or more voice recognition devices comprising:
   extracting the first voice data containing the disease name word directly out of the voice signal.

10. A server of an information providing system that provides information related to an infectious disease, the server comprising:
    a communicator that acquires regional infection information from one or more voice recognition devices connected via a network,
    wherein the one or more voice recognition devices acquire a voice signal, analyze the voice signal, and obtain the regional infection information from the voice signal, wherein the regional infection information indicates one or more infection alert levels and one or more regions associated with the one or more infection alert levels, wherein the one or more voice recognition devices acquires the number of users in each of the one or more regions and an assumed duration of stay for which the users stay in each of the one or more regions, and wherein the infection risk value of each of the one or more regions is calculated using a first correction coefficient of a region corresponding to the infection risk value, and the first correction coefficient is a coefficient that increases the infection risk value of the corresponding region as at least one selected from the group consisting of the number of users in the corresponding region and the assumed duration of stay for which the users stay in the corresponding region increases; and a processor that calculates, based on the regional infection information, an infection risk value representing a magnitude of a risk of infection in each of the one or more regions and that generates output information in accordance with the infection risk value for each of the one or more regions, wherein the one or more voice recognition devices analyze the voice signal with the following processes:

recognizing the voice signal acquired by the one or more voice recognition devices;

extracting first voice data containing a disease name word out of the voice signal;

extracting second voice data from a voice signal obtained during a certain period of time before and after a time that the first voice data was obtained;

identifying a place associated with the first voice data from the second voice data;

identifying a date and time word and a person word from the second voice data;

identifying an infection alert level based on the disease name word; and generating the regional infection information associating the identified place corresponding to one of the one or more regions, the date and time word, and the person word, with the identified infection alert level.

11. The server according to claim 10, wherein the one or more voice recognition devices analyze the voice signal with the following processes:

extracting the first voice data containing the disease name word directly out of the voice signal.

* * * * *